US007323480B2

(12) United States Patent
Zhu et al.

(10) Patent No.: US 7,323,480 B2
(45) Date of Patent: Jan. 29, 2008

(54) SUBSTITUTED TRIAZOLES AS MODULATORS OF PPAR AND METHODS OF THEIR PREPARATION

(75) Inventors: Yan Zhu, Foster City, CA (US); Jingyuan Ma, Fremont, CA (US); Peng Cheng, Union City, CA (US); Zuchun Zhao, Pleasanton, CA (US); Francine M. Gregoire, Lafayette, CA (US); Vera A. Rakhmanova, Foster City, CA (US)

(73) Assignee: Metabolex, Inc., Hayward, CA (US)

( * ) Notice: Subject to any disclaimer, the term of this patent is extended or adjusted under 35 U.S.C. 154(b) by 0 days.

(21) Appl. No.: 11/137,678

(22) Filed: May 24, 2005

(65) Prior Publication Data

US 2006/0014809 A1    Jan. 19, 2006

Related U.S. Application Data

(60) Provisional application No. 60/574,426, filed on May 25, 2004.

(51) Int. Cl.
*A61K 31/4192* (2006.01)
*A61K 31/501* (2006.01)
*C07D 249/06* (2006.01)
*C07D 257/04* (2006.01)

(52) U.S. Cl. ............... 514/359; 514/252.05; 514/381; 544/366; 548/255; 548/252; 548/254

(58) Field of Classification Search ................ 514/359, 514/252.05; 548/255; 544/366
See application file for complete search history.

(56) References Cited

U.S. PATENT DOCUMENTS

| | | | |
|---|---|---|---|
| 2,711,424 A | 6/1955 | Suter et al. |
| 3,158,645 A | 11/1964 | Newcer et al. |
| 3,378,582 A | 4/1968 | Bolhofer |
| 3,444,299 A | 5/1969 | Woo et al. |
| 3,469,009 A | 9/1969 | Klingbail |
| 3,517,050 A | 6/1970 | Bolhofer |
| 3,517,051 A | 6/1970 | Bolhofer |
| 3,536,809 A | 10/1970 | Applezweig |
| 3,546,229 A | 12/1970 | Griot |
| 3,558,778 A | 1/1971 | Klingbail |
| 3,564,042 A | 2/1971 | Griot |
| 3,598,123 A | 8/1971 | Zaffaroni |
| 3,658,829 A | 4/1972 | Nakamura et al. |
| 3,674,836 A | 7/1972 | Creger |
| 3,707,549 A | 12/1972 | Mils |
| 3,816,446 A | 6/1974 | Bolhofer |
| 3,845,770 A | 11/1974 | Theeuwes et al. |
| 3,860,628 A | 1/1975 | Shuman |
| 3,876,791 A | 4/1975 | Hubbard et al. |
| 3,916,899 A | 11/1975 | Theeuwes et al. |
| 3,923,855 A | 12/1975 | Shuman |
| 3,953,490 A | 4/1976 | Shuman |
| 4,001,268 A | 1/1977 | Kovar et al. |
| 4,008,719 A | 2/1977 | Theeuwes et al. |
| 4,067,996 A | 1/1978 | Najer et al. |
| 4,072,754 A | 2/1978 | Schacht et al. |
| 4,125,729 A | 11/1978 | Trust et al. |
| 4,146,623 A | 3/1979 | Parker |
| 4,168,385 A | 9/1979 | Trust et al. |
| 4,250,191 A | 2/1981 | Edwards |
| 4,338,330 A | 7/1982 | Gillet et al. |
| 4,508,882 A | 4/1985 | Yoshida et al. |
| 4,528,311 A | 7/1985 | Beard et al. |
| 4,532,135 A | 7/1985 | Edwards |
| 4,714,762 A | 12/1987 | Hoefle et al. |
| 4,863,802 A | 9/1989 | Moore et al. |
| 4,891,396 A | 1/1990 | Aver et al. |
| 4,910,211 A | 3/1990 | Imamura et al. |
| 4,933,367 A | 6/1990 | Wolff et al. |
| 5,013,556 A | 5/1991 | Woodle et al. |
| 5,041,640 A | 8/1991 | Creger |
| 5,132,429 A | 7/1992 | Narita et al. |
| 5,284,599 A | 2/1994 | Iwaki et al. |
| 5,476,946 A | 12/1995 | Linker et al. |

(Continued)

FOREIGN PATENT DOCUMENTS

| | | |
|---|---|---|
| EP | 0 077 938 A2 | 5/1983 |
| EP | 0 105 494 A2 | 4/1984 |
| EP | 0 306 708 A1 | 3/1989 |
| EP | 1 162 196 A1 | 12/2001 |
| EP | 1371650 A1 | 12/2003 |
| GB | 1403309 | 8/1975 |
| JP | 49-51243 A | 5/1974 |
| JP | 49-51246 A | 5/1974 |
| JP | 53-015325 A2 | 2/1978 |
| JP | 53-71071 A | 6/1978 |

(Continued)

OTHER PUBLICATIONS

Aronow, W.S., et al., "Effect of halofenate on serum lipids", Clin. Pharmacol. Ther., 1973, vol. 14, No. 3, pp. 358-365.

(Continued)

*Primary Examiner*—Rebecca Anderson
*Assistant Examiner*—Yong Chu
(74) *Attorney, Agent, or Firm*—Townsend and Townsend and Crew LLP

(57) ABSTRACT

The present invention is directed to certain novel triazole compounds represented by Formula I and pharmaceutically acceptable salts, solvates, hydrates, and prodrugs thereof. The present invention is also directed to methods of making and using such compounds and pharmaceutical compositions containing such compounds to treat or control a number of diseases mediated by PPAR such as glucose metabolism, lipid metabolism and insulin secretion, specifically Type 2 diabetes, hyperinsulemia, hyperlipidemia, hyperuricemia, hypercholesteremia, atherosclerosis, one or more risk factors for cardiovascular disease, Syndrome X, hypertriglyceridemia, hyperglycemia, obesity, and eating disorders.

21 Claims, 5 Drawing Sheets

U.S. PATENT DOCUMENTS

| | | | |
|---|---|---|---|
| 5,496,826 | A | 3/1996 | Watson et al. |
| 5,500,332 | A | 3/1996 | Vishwakarma et al. |
| 5,516,914 | A | 5/1996 | Winter et al. |
| 5,518,625 | A | 5/1996 | Priegnitz et al. |
| 5,554,759 | A | 9/1996 | Vishwakarma |
| 5,700,819 | A | 12/1997 | Aotsuka et al. |
| 5,716,987 | A | 2/1998 | Wille |
| 5,766,834 | A | 6/1998 | Chen et al. |
| 5,859,501 | A | 1/1999 | Chi |
| 5,874,431 | A | 2/1999 | Stevens et al. |
| 5,883,124 | A | 3/1999 | Samid |
| 5,942,626 | A | 8/1999 | Winter et al. |
| 6,013,659 | A | 1/2000 | Goldfarb et al. |
| 6,034,246 | A | 3/2000 | Stevens et al. |
| 6,037,393 | A | 3/2000 | Okumura et al. |
| 6,184,235 | B1 | 2/2001 | Connor et al. |
| 6,201,000 | B1 | 3/2001 | Luther et al. |
| 6,248,768 | B1 | 6/2001 | Yamada et al. |
| 6,262,118 | B1 | 7/2001 | Luskey et al. |
| 6,417,212 | B1 | 7/2002 | Brooks et al. |
| 6,506,747 | B1 | 1/2003 | Betageri et al. |
| 6,610,696 | B2 | 8/2003 | Brooks et al. |
| 6,613,802 | B1 | 9/2003 | Luskey et al. |
| 6,624,194 | B1 | 9/2003 | Luskey et al. |
| 6,646,004 | B1 | 11/2003 | Luskey et al. |
| 6,670,395 | B1 | 12/2003 | Wille |
| 6,710,063 | B1 | 3/2004 | Chao et al. |
| 6,875,782 | B2 * | 4/2005 | Cheng et al. ............... 514/364 |
| 2003/0203947 | A1 | 10/2003 | Chao et al. |
| 2003/0207915 | A1 | 11/2003 | Cheng et al. |
| 2003/0207916 | A1 | 11/2003 | Cheng et al. |
| 2003/0207924 | A1 | 11/2003 | Cheng et al. |
| 2003/0220399 | A1 | 11/2003 | Luskey et al. |
| 2003/0225158 | A1 | 12/2003 | Auerbach et al. |
| 2004/0019090 | A1 | 1/2004 | Brooks et al. |
| 2004/0039053 | A1 | 2/2004 | Luskey et al. |
| 2004/0077659 | A1 | 4/2004 | Oliver |
| 2004/0204472 | A1 | 10/2004 | Briggs |
| 2005/0033084 | A1 | 2/2005 | Daugs |

FOREIGN PATENT DOCUMENTS

| | | |
|---|---|---|
| JP | 60-109578 A | 6/1986 |
| WO | WO 97/28149 A1 | 8/1997 |
| WO | WO 98/23252 A1 | 6/1998 |
| WO | WO 98/04955 A1 | 11/1998 |
| WO | WO 99/11627 A1 | 3/1999 |
| WO | WO 99/04815 A1 | 4/1999 |
| WO | WO 00/35886 A3 | 6/2000 |
| WO | WO 00/74666 A2 | 12/2000 |
| WO | WO 03/074051 A1 | 9/2003 |
| WO | WO 03/080545 A2 | 10/2003 |
| WO | WO 2005/115383 A2 | 12/2005 |
| WO | WO 96/26207 A1 | 8/2006 |

OTHER PUBLICATIONS

Aronow, W.S., et al., "Halofenate: An Effective Hypolipemia- and Hypouricemia- Inducing Drug", Current Therapeutic Research, 1973, vol. 15, No. 12, pp. 902-906.

Babler, J., et al., "Reduction of Acid Chlorides with Sodium Borohydride in N, N-Dimethylformamide: Nature of the Reaction Intermediate and a Method for it's Conversion to the Corresponding Aldehyde with Minimal Alcohol Formation," Tetrahedron Letters, 1981, vol. 22, pp. 11-14.

Bardin, C.W., eds., Current Therapy in Endocrinology and Metabolism, 6th Edition, Mosby—Year Book, Inc., St. Louis, MO, 1997, pp. 509-519.

Barrett-Conner, "Epidemiology, Obesity, and Non-Insulin-Dependent Diabetes Mellitus", Epidemol. Rev., 1989, vol. 11, pp. 172-181.

Bassett, D.R., et al., "Effects of halofenate and probenecid in serum lipids and uric acid in hyperlipidemic, hyperuricemic adults," Clin. Pharmacol. Ther. 1977, vol. 22, No. 3, pp. 340-351.

Bell, G., et al., "Glucokinase Mutations, Insulin secretion, and Diabetes Mellitus," Annu. Rev. Physiol., 1996, vol. 58, No. pp. 171-187.

Berkow, R., Chapter 94, "Disorders of Carbohydrate Metabolism," The Merck Manual of Diagnosis and Therapy 15th ed., *Merck Sharp & Dohme Research Laboratories*, 1987, pp. 1069-1072.

Bluestone, R., et al., "Halofenate *Its Selection and Trial as a Primary Uricosuric Agen"t*, Arthritis Rheum., 1975, vol. 18, pp. 859-862.

Brooks, D. A., et al., "Design and Synthesis of 2-Methyl-2-{4-[2-(5-methyl-2-aryloxazol-4-yl)ethoxy]phenoxy} propionic Acids: A New Class of Dual PPARalγ Agonists," J. Med. Chem., 2001, vol. 44, No. 13, 2061-2064.

Chaikin, Saul W., et al., "Reduction of Aldehydes, Ketones and Acid Chlorides by Sodium Borohydride," J. Amer. Chem. Soc., 1949 vol. 71, pp. 122-127.

Chiasson, J., et al., "The Efficacy of Acarbose in the Treatment of Patients with Non-Insulin-dependent Diabetes Mellitus," Annals of Intern. Med., 1994 vol. 121, No. 12, pp. 928-935.

Coniff, R., et al., "Acarbose: A Review of US Clinical Experience," Clinical Therapeutics, 1997, vol. 19, No. 1, pp. 16-26.

Coniff, R., et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus," The American Journal of Medicine, 1995, vol. 98, pp. 443-451.

Dorfler, H., et al., "Primärer Verteilungsraum und Plasmahalbwertszeit von intravenous verabreichtem Insulin," Med. Poliklinik Univ. Muchen, vol. 82, pp. 1297-1299.

Dressel, U., et al., "The peroxisome proliferator-activated receptor beta/delta agonist, GW501516, regulates the expression of genes involved in lipid catabolism and energy uncoupling in skeletal muscle cells," Mol. Endocrinol. 2003, vol. 17, No. 12, pp. 2477-2493.

Edelman, S. V., et al., "Non-Insulin-Dependent Diabetes Mellitus", Current Therapy in Endocrinology and Metabolism, 1997, pp. 430-438.

El-Sherief, et al., "Synthesis and Antimicrobial Activities of Some New Benzimidazoles, Part I," Bull. Fac. Sci. Assiut Univ. B, 1995, vol. 24, No. 1, pp. 111-123.

Fajans, S., et al., "Maturity Onset Diabetes of the Young (MODY)" Diabetes Medicine, 1996, vol. 13, pp. S90-S95.

Fanelli, G.M., Jr., "Renal Excretion and Uricosuric Properties of Halofenate A Hypolipidemic Uricosuric Agent in the Chimpanzee," J. Pharmacol. Exp. Ther. 1972, vol. 180, pp. 377-396.

Feldman, E.B., et al., "Effects of Halofenate on Glucose Tolerance in Patients with Hyperlipoproteinemia," Journal Clinical Pharmacology, 1978, vol. 18, pp. 241-248.

Feldman, E.B., et al., "Insulin Sensitivity in Hypertriglyceridemia: induction by combined triglyceride and uric lowering," Clinical Research, 1975, vol. 23, No. 1, pp. 43A.

Fell, H., et al., "Endocytosis of Sugars in Embryonic Skeletal Tissues in Organ Culture," J. Cell Sci., vol. 4, pp. 89-103.

Fingl, et al., "General Principles," The Pharmacological Basis of Therapeutics, 1975, Ch. 1, pp. 1-45.

Flier, J., "Insulin Receptors and Insulin Resistance," Ann Rev. Med., 1983, vol. 34, pp. 145-161.

Friedberg, S.J., "The Control of Insulin Resistant and Refractory Type II Diabetes Mellitus by Means of Halofenate-Sulfonylurea Combined Regimen," Clinical Research, 1986, vol. 34, pp. 682A.

Garcia, M. J., et al., "Morbidity and mortality in diabetics in the Framingham population. Sixteen year follow-up study," Diabetes Care, 1974, vol. 23, No. 2, pp. 105-111.

Gavin III, J.R., et al., "Report of the Expert Committee on the Diagnosis and Classification of Diabetes Mellitus," Diabetes Care, 1999, vol. 22, Supplement 1, pp. S5-S19.

Goetze, S., et al., "PPARγ-Ligands Inhibit Migration Mediated by Multiple Chemoattractants in Vascular Smooth Muscle Cells," Journal of Cardiovascular Pharmacology, 1999, vol. 33, pp. 798-806.

Gordon, D., et al., "High-density lipoprotein-the clinical implications of recent studies," New England Journal of Medicine, 1989, vol. 321, No. 19, pp. 1311-1316.

Greene, T.W., et al., Protective Groups In Organic Chemistry (1991) 2nd ed.

Guerre-Millo, M., et al. "Peroxisome proliferator-activated receptor alpha activators improve insulin sensitivity and reduce adiposity," J Biol Chem, 2000, vol. 275, 16638-16642.

Haffner, S., "Management of dyslipidemia in adults with diabetes," Diabetes Care, 1998 vol. 21, No. 1, pp. 160-178.

Harrison, et al., Compendium of Synthetic Organic Methods (1971-1996) vol. 1-8.

Howard, B., et al., "Lipoprotein Composition in Diabetes Mellitus," Atherosclerosis, 1978, vol. 30, pp. 153-162.

Hucker, H.B., et al., "Metabolism of a New Hypolipidemic Agent, 2-Acetamidoethyl (p-Chlorophenyl) (m-Trifluoromethylphenoxy)-Acetate (Halofenate) in the Rat, Dog, Rhesus Monkey and Man," The Journal of Pharmacology and Experimental Therapeutics, 1971, vol. 179, No. 2, pp. 359-371.

Hutchison, J.C., et al., "The Uricosuric Action of Halofenate (MK-185) in Patients with Hyperuricemia or Uncomplicated Primary Gout and Hyperlipidemia," Atherosclerosis, 1973, vol. 18, pp. 353-362.

Iwamoto, Y., et al., "Effect of Combination Therapy of Troglitazone and Sulphonylureas in Patients with Type 2 Diabetes Who Were Poorly Controlled by Sulphonylurea Therapy Alone," Diabetic Medicine, 1996, vol. 13, pp. 365-370.

Jain, A., et al., "Potentiation of Hypoglycemic Effect of Sulfonylureas by Halofenate," New England J. of Med., 1975, vol. 293, No. 25, pp. 1283-1286.

Jain, A., et al., "The effect of MK-185 on some aspects of uric acid metabolism," Clin. Pharmacol. Ther., 1970, vol. 11, pp. 551-557.

Jain, S., et al., Erythrocyte Membrane Lipid peroxidation and Glycosylated hemoglobin in Diabetes, Diabetes, 1989, vol. 38, pp. 1539-1543.

Joslin, E., "Arteriosclerosis and Diabetes," Annals of Clinical Medicine, 1927, vol. 5, No. 12, pp. 1061-1079.

Kaplan, R. M., et al., Cardiovascular Disease, Health and Human Behavior (1993) 206-242.

Keller, H., et al., "Peroxisome Proliferator-Activated Receptors, A Link Between Endocrinology and Nutrition," W. Trends Endoodn. Met., 1993, vol. 4, No. 9, pp. 291-296.

Keller, V.C., et al., "Die Behandung von Hyperlipidamie und Hyperurikamie mit 2-Acetamidoathyl-(4-chlorophenyl)-(3-trifluoromethylphenoxy)-acetat (Halofenat), einem Derivat des Clofibrat," Arzneim-Forsch. (Drug Res.) 1976, vol. 26, No. 12, pp. 2221-2224.

Kende, A. "Ethyl 4-Hydroxycrotonate," Organic Syntheses, 1985, vol. 64, pp. 104.

Knowler, et al., "Obesity in the Pima Indians: its magnitude and relationship with diabetes," Am. J. Clin. Nutr., 1991, vol. 53, pp. 1543-1551.

Kobayashi, M., et al., "Improvement of Glucose Tolerance in NIDDM by Clofibrate *Randomized Double-Blind Study*," Diabetes Care, 1988, vol. 11, No. 6, pp. 495-499.

Koh, E. H., et al., "Peroxisome proliferator-activated receptor (PPAR)-alpha activation prevents diabetes in OLETF rats: comparison with PPAR-gamma activation," Diabetes, 2003, vol. 52, pp. 2331-2337.

Kohl, E. A., et al., "Improved Control of Non-insulin-dependent Diabetes Mellitus by Combined Halofenate and Chlorpropamide Therapy," Diabetes Care, 1984 vol. 7, No. 1, pp. 19-24.

Kreisberg, R.A., "Hyperlipidemia," Current Therapy in Endocrinology and Metabolism 6th Edition, 1997, pp. 509-519.

Krut, L. H., et al., "Comparison of Clofibrate with Halofenate in Diabetics with Hyperlipidaemia," SA Med. J., 1977, pp. 348-352.

Kudzma, D.J., et al., "Potentiation of Hypoglycemic Effect of Chlorpropamide and Phenformin by Halofenate," Diabetes, 1977, vol. 26, No. 4, pp. 291-295.

Kuntznen, V.O., et al., "Wirkung von Halofenat auf Triglycerid-und Harnsaurespiegel sowie auf Gerinnungs- und Thrombozytenverhalten bei Patienten mit Hyperlipoproteinamie Typ IV und Hyperurikamie," Arzneim-Forsch. (Drug Res)., 1978, vol. 28, pp. 2349-2352.

Kwiterovich, P., "State-of-the-Art Update and Review: Clinical Trials of Lipid-Lowering Agents," The American Journal of Cardiology, 1998, vol. 82, No. 12A, pp. 3U-17U.

Laakso, M., et al., "Epidemiology of Macrovascular Disease in Diabetes," Diabetes Reviews, 1997, vol. 5, No. 4, pp. 294-315.

Langer, R. "New methods of Drug Delivery," Science, 1990, vol. 149, pp. 1527-1533.

Larock, Comprehensive Organic Transformations, VCH Publishers Inc., (1989).

Leibowitz, M.A., et al., Activation of PPARdelta alters lipid metabolism in db/db mice, Federation of European Biochemical Societies, 2000, vol. 473, pp. 333-336.

Leroith, D. et al. (eds.), Diabetes Mellitus, Lippincott-Raven Publishers, Philadelphia, PA U.S.A. (1966) (all references cited therein?).

Lin, J.H., et al., "Inhibition and Induction of Cytochrome P450 and the Clinical Implications," Clin Pharmacokinet, 1998, vol. 35, pp. 361-390.

Mahley, R. W., et al., Disorders of Lipid Metabolism, Williams Textbook of Endocrinology, 1998, pp. 1099-1153.

Maier, et al., "Metamorphosis of Palladium and Its Relation to Selectivity in the Rosenmund Reaction,"J. Amer. Chem. Soc., 1986, vol. 108, pp. 2608-2616.

Malher, R., Clinical Review 102, "Type 2 Diabetes Mellitus: Update on Diagnosis, Pathophysiology, and Treatment," J. Clin. Endocrinol. Metab., 1999, vol. 84, No. 4, pp. 1165-1171.

Mandel, L. R., "Studies on the Mechanism of Action of Halofenate," Lipids, 1976, vol. 12, No., pp. 34-43.

March, J., Advanced Organic Chemistry Chapter 4, 1992, pp. 94-164.

Marshall, James A., et al, "Acyclic Stereocontrol in Catalyzed Intramolecular Diels-Alder Cyclizations Leading to Octahydronaphthalenecarboxaldehydes," J. Amer. Chem. Soc., 1987, vol. 109, pp. 1186-1194.

McMahon, et al., "Some Effects of MK-185 on Lipid and Uric Acid Metabolism in Man," Univ. Mich. Med. Center J., 1970, vol. 36, No. 4, pp. 247-248.

Metabolex, Metabolic Diseases Drug Discovery & Development Summit, The Diabetes Biopharmaceutical Company, Strategic Research Institute, (May 6-7, 2002).

Miners, J.O., et al., "Cytochrome P4502C9: an enzyme of major importance in human drug metabolism," J Clin Pharmacol, 1998, vol. 45, pp. 525-538.

Mitsunobu, O. "The Use of Diethyl Azodicarboxylate and Triphenylphosphine in Synthesis and Transformation of Natural Products," Synthesis, 1981, pp. 1-28.

Morgan, J. P., et al., "Hypolipidemic, uricosuric, and thyroxine-displacing effects of MK-185 (halofenate)," Clin. Pharmacol. Therap., 1971, vol. 12, No. 3, pp. 517-524.

Neuman, J., et al., "A double-blind comparison of the hypolipidemic and hypouricemic action of halofenate and clofibrate in patients with hyperlipoprteinemia," The International Cardiovascular Society, pp. 532-537.

Oliver, W.R., et al., "A selective peroxisome proliferator-activated receptor delta agonist promotes reverse cholesterol transport," PNAS, 2001, vol. 98, No. 9, pp. 5306-5311.

Pelkonen, O., et al.,"Inhibition and induction of human cytochrome P450 (CYP) enzymes," Xenobiotica, 1998. vol. 28, No. 12, pp. 1203-1253.

Peters, A., et al., "A clinical approach for the diagnosis of diabetes mellitus: an analysis using glycosylated hemoglobin levels." Meta-analysis Research Group on the Diagnosis of Diabetes Using Glycated Hemoglobin Levels, JAMA, 1996, vol. 276, No. 15, 1246-1252.

Qu, et al., "Search for New Antiphytovirucides," Wujan Univ. Journal of National Science, 1998, vol. 3 No. 2, pp. 201-204.

Qu, et al., "Some New Antiphytoviral Compounds Containing Trifluoromethyl Group," Wuhan Univ. Journal of National Science, 1996, vol. 1, No. 2, pp. 283-284.

Ravenscroft, P.J., et al., "Studies of the uricosuric action of the hypolipidemic drug halofenate," Clin. Pharmacol. Ther., 1973, vol. 14, No. 4, pp. 547-551.

Reaven, G. M., "Insulin Resistance and Human Disease: A Short History," J. Basic & Clin. Phys. & Pharm., 1998, vol. 9, No. 2-4, pp. 387-406.

Reaven, G. M., "Pathophysiology of Insulin Resistance in Human Disease," Physiol. Rev. 1995, vol. 75, No. 3, pp. 473-486.

Remington's Pharmaceutical Sciences (1985) 17th ed.

Ryan, J. R., "The metabolic spectrum of halofenate," Int. J. Clin. Pharmacol., 1975, vol. 12, No. ½, pp. 239-243.

Safak, et al., "Synthesis of Some Benzimidazol Derivatives, and Their Effects on Serum Total Cholesterol and Trigliceride Levels in Rats" FABAD J. Farm. Sci., 1983, vol. 8, No. 1, pp. 19-29.

Schaeffer, S., "Trying to beat PPAR," BioCentury, *The Bernstein Report on BioBusiness*, 2004, pp. 1-3.

Schapel, G.J., et al., "Efficacy and Interactions of Oxandrolone, Halofenate and Clofibrate in a Factorial Study on Experimental Acute Nephrotic Hyperlipidemia," The Journal of Pharmacology and Experimental Therapeutics, 1975, vol. 194, No. 1, pp. 274-284.

Schlosstein, L.H., et al. "Studies with some novel uricosuric agents and their metabolites: correlation between clinical activity and drug-induced displacement of urate from its albumin-binding sites," J. Lab. Clin. Med., vol. 82, No. 3, pp. 412-418.

Sirtori, C., et al., "Clinical Evaluation of MK-185: A New Hypolipidemic Drug," Lipids, 1971, 7, No. 2, pp. 96-99.

Skyler, J.S., "Glucose Control in Type 2 Diabetes Mellitus," Annals of Internal Medicine, 1997, vol. 127, Np. 9, pp. 837-838.

Stein, O., et al., "Atheroprotective mechanisms of HDL," Atherosclerosis, 1999, vol. 144, pp. 285-303.

Steiner, A., et al., "A Comparative Review of the Adverse Effects of Treatments for Hyperlipidaemia," Drug Safety, 1991, vol. 6, No. 2, pp. 118-130.

Sznaidman, et al., Novel selective small molecule agonists for peroxisome proliferator-activated receptor delta (PPARdelta)-synthesis and biological activity, Bioorg. Med. Chem. Lett. (2003) 13:1517-1521.

Tanaka, et al., "Activation of peroxisome proliferator-activated receptor delta induces fatty acid beta-oxidation in skeletal muscle and attenuates metabolic syndrome," PNAS 2003, vol. 100, No. 26, pp. 15924-15929.

Taskinen, M.R., "Lipid disorders in NIDDM: implications for treatment," Journal of Internal Medicine, 1998, vol. 244, pp. 361-370.

Trust, R. I., et al., "(Aryloxy)[p-(aryloxy)phenyl]- and (Aryloxy)[p-arylthio)phenyl]acetic Acids and Esters as Hypolipidemic Agents," Journal of Medicinal Chemistry, 1979, vol. 22, No. 9, pp. 1068-1074.

Turner, N., et al., "Insulin resistance, impaired glucose tolerance and non-insulin-dependent diabetes, pathologic mechanisms and treatment: Current status and therapeutic possibilities," Prog Drug Res., 1998, pp. 33-94.

Varma, et al., "Synthesis of Substituted 2-Phenylbenzothiazoles & 5(6)-Nitro-1, 3-disubsituted-benzimidazoline-2-thiones as CNS Active Agents," Indian Journal of Chemistry, 1988, vol. 27B, No. 5, pp. 438-442.

Vedell, E.S., et al., "Differential Effects of Chronic Halofenate Administration on Drug Metabolism in Man," Fed. Proc., 1972, vol. 31, No. 2, pp. 538.

Wang, Y. X., et al., "Peroxisome-proliferator-activated receptor delta activates fat metabolism to prevent obesity," Cell, 2003, vol. 113, pp. 159-170.

Wermuth, C.G., "Molecular Variations Based on Isosteric Replacements," The Practice of Medicinal Chemistry, 1996, pp. 203-237.

Wilson, J., et al., (ed.) Disorders of Lipid Metabolism, Chapter 23, Textbook of Endocrinology, 9th Edition, 1998, W.B. Sanders Company, Philadelphia, PA. (all references cited therein).

Winterfeldt, E., "Applications of Diisobutylaluminium Hydride (DIBAH) and Triisolbutylaluminium (TIBA) as Reducing Agents in Organic Synthesis," Synthesis, 1975, pp. 617-630.

Wolfram, G. et al., "Primarer Verteilungrsaum und Plasmahalhwertszeit von intravenos verabreichtem Insulin," Verh. Dtsch. Ges. Inn. Med., 1973, vol. 79, No. 1, pp. 1297-1299.

Wood, Jeffery L., et al., "A Direct Conversion of Esters to Nitriles," Tetrahedron. Letters, 1979, pp. 4907-4910.

Wright, A.D., et al., "UKPDS 28: A Randomized Trial of Efficacy of Early Addition of Metformin in Sulfonylurea-Treated Type 2 Diabetes," Diabetes Care, 1998, vol. 21, pp. 87-92.

Xiaoling, H., et al., "Search for New Antiphytovirucides," J. Wuhan Univ. (Nature Science Edition), 1995, vol. 41, No. 2, pp. 142-148.

* cited by examiner

800

850

810

860

820

870

830

880

840

890

SUBSTITUTED TRIAZOLES AS MODULATORS OF PPAR AND METHODS OF THEIR PREPARATION

CROSS-REFERENCES TO RELATED APPLICATIONS

This application claims the benefit of U.S. patent application No. 60/574,426, filed May 25, 2004, the content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Peroxisome Proliferator-Activated Receptors (PPARs) are implicated in a number of biological processes and disease states including Type 2 diabetes, hyperinsulemia, hyperlipidemia, hyperuricemia, hypercholesteremia, atherosclerosis, one or more risk factors for cardiovascular disease, Syndrome X, hypertriglyceridemia, hyperglycemia, obesity, eating disorders, and suppressing appetite.

Diabetes, Hyperinsulemia, Hypertriglyceridemia, Hyperglycemia, Atherosclerosis, and Cardiovascular Disease Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996), and all references cited therein. According to the American Diabetes Association, diabetes mellitus is estimated to affect approximately 6% of the world population. Uncontrolled hyperglycemia is associated with increased and premature mortality due to an increased risk for microvascular and macrovascular diseases, including nephropathy, neuropathy, retinopathy, hypertension, cerebrovascular disease, coronary heart disease, and other cardiovascular diseases. Therefore, control of glucose homeostasis is a critically important approach for the treatment of diabetes.

There are two major forms of diabetes: Type 1 diabetes (formerly referred to as insulin-dependent diabetes or IDDM); and Type 2 diabetes (formerly referred to as non-insulin dependent diabetes or NIDDM).

Type 1 diabetes is the result of an absolute deficiency of insulin, the hormone which regulates glucose utilization. This insulin deficiency is usually characterized by β-cell destruction within the Islets of Langerhans in the pancreas, which usually leads to absolute insulin deficiency. Type 1 diabetes has two forms: Immune-Mediated Diabetes Mellitus, which results from a cellular mediated autoimmune destruction of the β-cells of the pancreas; and Idiopathic Diabetes Mellitus, which refers to forms of the disease that have no known etiologies.

Type 2 diabetes is a complex disease characterized by defects in glucose and lipid metabolism. Typically there are perturbations in many metabolic parameters including increases in fasting plasma glucose levels, free fatty acid levels and triglyceride levels (hypertriglyceridemia), as well as a decrease in the ratio of HDL/LDL. One of the principal underlying causes of diabetes is thought to be when muscle, fat and liver cells fail to respond to normal concentrations of insulin (insulin resistance). Insulin resistance may be due to reduced numbers of insulin receptors on these cells, or a dysfunction of signaling pathways within the cells, or both. Insulin resistance is characteristically accompanied by a relative, rather than absolute, insulin deficiency. Type 2 diabetes can range from predominant insulin resistance with relative insulin deficiency to predominant insulin deficiency with some insulin resistance.

The beta cells in insulin resistant individuals initially compensate for this insulin resistance by secreting abnormally high amounts of insulin (hyperinsulemia). Over time, these cells become unable to produce enough insulin to maintain normal glucose levels, indicating progression to Type 2 diabetes. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Type 2 diabetes is brought on by a combination of genetic and acquired risk factors—including a high-fat diet, lack of exercise, and aging. Worldwide, Type 2 diabetes has become an epidemic, driven by increases in obesity and a sedentary lifestyle, widespread adoption of western dietary habits, and the general aging of the population in many countries. In 1985, an estimated 30 million people worldwide had diabetes—by 2000, this figure had increased 5-fold, to an estimated 154 million people. The number of people with diabetes is expected to double between now and 2025, to about 300 million.

Therapies aimed at reducing peripheral insulin resistance are available. The most relevant to this invention are drugs of the thiazolidinedione (TZD) class namely troglitazone, pioglitazone, and rosiglitazone. In the US these have been marketed under the names Rezulin™, Avandia™ and Actos™, respectively. The principal effect of these drugs is to improve glucose homeostasis. Notably in diabetics treated with TZDs there are increases in peripheral glucose disposal rates indicative of increased insulin sensitivity in both muscle and fat.

Premature development of atherosclerosis and increased rate of cardiovascular and peripheral vascular diseases are characteristic features of patients with diabetes, with hyperlipidemia being an important precipitating factor for these diseases.

Hyperlipidemia

Hyperlipidemia is a condition generally characterized by an abnormal increase in serum lipids in the bloodstream and, as noted above, is an important risk factor in developing atherosclerosis and coronary heart disease. For a review of disorders of lipid metabolism, see, e.g., Wilson, J. et al., (ed.), *Disorders of Lipid Metabolism*, Chapter 23, Textbook of Endocrinology, 9th Edition, (W.B. Sanders Company, Philadelphia, Pa. U.S.A. 1998; this reference and all references cited therein are herein incorporated by reference). Serum lipoproteins are the carriers for lipids in the circulation. They are classified according to their density: chylomicrons; very low-density lipoproteins (VLDL); intermediate density lipoproteins (IDL); low density lipoproteins (LDL); and high density lipoproteins (HDL). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia.

Hypercholesterolemia

Hypercholesterolemia, a form of hyperlipidemia, is characterized by excessive high levels of blood cholesterol. The blood cholesterol pool is generally dependant on dietary uptake of cholesterol from the intestine and biosynthesis of cholesterol throughout the body, especially the liver. The majority of the cholesterol in plasma is carried on apolipoprotein B-containing lipoproteins, such as the very-low-density lipoproteins (VLDL), low-density lipoproteins (LDL), intermediate density lipoproteins (IDL) and high density lipoproteins (HDL). Hypercholesterolemia is characterized by elevated LDL cholesterol levels. The risk of coronary artery disease in man increases when LDL and VLDL levels increase. Conversely, high HDL levels are protective against coronary artery disease (see Gordon, D. and Rifkind, B. *N. Engl. J. Med.* 1989 321: 1311-15; and Stein, O and Stein, Y. *Atherosclerosis* 1999 144: 285-303). Therefore, although it is desirable to lower elevated levels of LDL, it is also desirable to increase HDL levels.

Initial treatment for hypercholesterolemia is to place the patients on a low fat/low cholesterol diet coupled with adequate physical exercise, followed by drug therapy when LDL-lowering goals are not met by diet and exercise alone. HMG-CoA reductase inhibitors (statins) are useful for treating conditions associated with high LDL levels. Other important anti-lipidemia drugs include fibrates such as gemfibril and clofibrate, bile acid sequestrant such as cholestyramine and colestipol, probucol, and nicotinic acid analogs.

Elevated cholesterol levels are in turn associated with a number of disease states, including coronary artery disease, angina pectoris, carotid artery disease, strokes, cerebral arteriosclerosis, and xanthoma.

Dyslipidemia

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. *Ann. Chim. Med.* (1927) 5: 1061-1079). Epidemiological studies since then have confirmed the association and have shown a several-fold increase in coronary deaths among diabetic subjects when compared with nondiabetic subjects (see, e.g., Garcia, M. J. et al., Diabetes (1974) 23: 105-11; and Laakso, M. and Lehto, S. *Diabetes Reviews* (1997) 5(4): 294-315). Several lipoprotein abnormalities have been described among diabetic subjects (Howard B., et al., *Atherosclerosis* (1978) 30: 153-162).

Obesity

Obesity has reached epidemic proportions globally with more than 1 billion adults overweight—at least 300 million of them clinical obese—and is a major contributor to the global burden of chronic diseases including cardiovascular disease problems, conditions associated with insulin resistance such as Type 2 diabetes and certain types of cancers. The likelihood of developing Type 2 diabetes and hypertension rises steeply with increasing body fatness. Weight reduction leads to correction of a number of obesity—associated endocrine and metabolic disorders.

Effective weight management for individuals and groups at risk of developing obesity involves a range of long term strategies. These include prevention, weight maintenance, management of co-morbidities and weight loss. Existing treatment strategies include caloric restriction programs, surgery (gastric stapling) and drug intervention. The currently available anti-obesity drugs can be divided into two classes: central acting and peripheral acting. Three marketed drugs are Xenical (Orlistat), Merida (Sibutramine) and Adipex-P (Phentermine). Xenical is a non-systemic acting GI lipase inhibitor which is indicated for short and long term obesity management. Merida reduces food intake by reuptake inhibition of primarily norepinephrine and serotonin. Adipex-P is a phenteramine with sympathomimetic activities and suppresses appetite. It is indicated only for short term use. A more drastic solution to permanent weight loss is surgery and a gastric by-pass which limits absorption of calories through massive reduction in stomach size.

Carrying extra body weight and body fat go hand and hand with the development of diabetes. People who are overweight (BMI greater than 25) are at a much greater risk of developing type 2 diabetes than normal weight individuals. Almost 90% of people with type 2 diabetes are overweight.

Syndrome X, Hyperuricemia, Eating Disorders, and Suppressing Appetite

Syndrome X (including metabolic syndrome) is loosely defined as a collection of abnormalities including hyperinsulinemia, hyperuricemia, obesity, elevated levels of triglycerides, fibrinogen, small dense LDL particles, and plasminogen activator inhibitor 1 (PAI-1), and decreased levels of HDL-c. These abnormalities are associated with eating disorders, particularly an overactive appetite.

PPAR

PPARs are members of the nuclear receptor superfamily of transcription factors, a large and diverse group of proteins that mediate ligand-dependent transcriptional activation and repression. They play a role in controlling expression of proteins that regulate lipid metabolism. Furthermore, the PPARs are activated by fatty acids and fatty acid metabolites. Three PPAR subtypes have been isolated: PPARα, PPARβ (also referred to as δ or NUC1), and PPARγ. Each receptor shows a different pattern of gene expression by binding to DNA sequence elements, termed PPAR response elements (PPRE). In addition, each receptor show a difference in activation by structurally diverse compounds. To date, PPREs have been identified in the enhancers of a number of genes encoding proteins that regulate lipid metabolism suggesting that PPARs play a pivotal role in the dipogenic signaling cascade and lipid homeostasis (Keller, H. and Wahli, W. *Trends Endoodn. Met.* (1993) 4:291-296.

PPARα is found in the liver, heart, kidney, muscle, brown adipose tissue and gut and is involved in stimulating β-oxidation of fatty acids. PPARα is also involved in the control of cholesterol levels in rodents and in humans. Fibrates are weak PPARα agonists that are effective in the treatment of lipid disorders. In humans, they have been shown to lower plasma triglycerides and LDL cholesterol. In addition, PPARα agonists have also been reported to prevent diabetes and to improve insulin sensitivity and reduce adiposity in obese and diabetic rodents (see Koh, E. H. et al. *Diabetes* (2003) 52:2331-2337; and Guerre-Millo, M. et al. *J. Biol. Chem.* (2000) 275: 16638-16642).

PPARβ is ubiquitously expressed. Activation of PPARβ increases HDL levels in rodents and monkeys (see Oliver, W. R. et al. PNAS (2001) 98:5306-5311; and Leibowitz, M. D. et al. *FEBS Letters* (2000) 473:333-336). Moreover, PPARβ has been recently shown to be a key regulator of lipid catabolism and energy uncoupling in skeletal muscle cells (Dressel, U. et al. *Mol Endocrinol.* (2003) 17: 2477-2493). In rodents, activation of PPARβ induces fatty β-oxidation in skeletal muscle and adipose tissue, leading to protection against diet-induced obesity and diabetes (see Wang, Y. X. et al. *Cell* (2003) 113:159-170; and Tanaka et al. PNAS (2003) 100:15924-15929). In human macrophages, PPARP activation also increases the reverse cholesterol transporter ATP-binding cassette A1 and induces apolipoprotein A1-specific cholesterol efflux (see Oliver, W. R. et al. *PNAS* (2001) 98:5306-5311).

PPAR-γ is expressed most abundantly in adipose tissue and is thought to regulate adipocyte differentiation. Drugs of the thiazolidinedione (TZD) class namely troglitazone, pioglitazone, and rosiglitazone are potent and selective activators of PPAR-γ. In human, they increase insulin action, reduce serum glucose and have small but significant effects on reducing serum triglyceride levels in patients with type 2 diabetes.

Certain compounds that activate or otherwise interact with one or more of the PPARs have been implicated in the regulation of triglyceride and cholesterol levels in animal models. (See e.g., U.S. Pat. No. 5,859,501, and PCT publications WO 97/28149 and 99/04815.

Taken together, these data clearly indicate that PPARs agonists are useful in treating hypertriglyceridemia, hypercholesterolemia, obesity and type 2 diabetes.

Anti-lipidemia, anti-obesity and anti-diabetes agents are still considered to have non-uniform effectiveness, in part because of poor patient compliance due to unacceptable side effects. For Anti-lipidemia and anti-obesity agents, these side effects include diarrhea and gastrointestinal discomfort. For anti-diabetic agents, they include weight gain, edema and hepatotoxicity. Furthermore, each type of drug does not work equally well in all patients.

What is needed in the art are new compounds and methods useful for modulating peroxisome proliferators activated receptor, insulin resistance, fibrinogen levels, leptin levels, LDLc shifting LDL particle size from small dense to normal dense LDL. What is also needed in the art are new compounds and methods useful for treating Type 2 diabetes, hyperinsulemia, hyperlipidemia, hyperuricemia, hypercholesteremia, atherosclerosis, one or more risk factors for cardiovascular disease, Syndrome X, hypertriglyceridemia, hyperglycemia, obesity, eating disorders, and suppressing appetite. The present invention fulfills this and other needs by providing such compounds, compositions and methods for modulating peroxisome proliferators activated receptor, insulin resistance, fibrinogen levels, leptin levels, LDLc shifting LDL particle size from small dense to normal dense LDL. The present invention also provides compounds, compositions, and methods useful for treating Type 2 diabetes, hyperinsulemia, hyperlipidemia, hyperuricemia, hypercholesteremia, atherosclerosis, one or more risk factors for cardiovascular disease, Syndrome X, hypertriglyceridemia, hyperglycemia, obesity, eating disorders, and suppressing appetite.

BRIEF SUMMARY OF THE INVENTION

In one aspect, the present invention provides compounds having the formula:

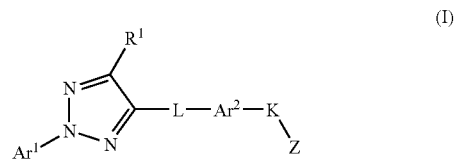

(I)

wherein $Ar^1$ represents a monocyclic or bicyclic aromatic ring system selected from the group consisting of phenyl, naphthyl, imidazolyl, benzimidazoyl, pyrrolyl, indolyl, thienyl, benzothienyl, furanyl, benzofuranyl, and benzodioxole. Each of these rings can be optionally substituted with from one to four $R^7$ substituents.

In the above formula, the symbol $Ar^2$ represents a 6-membered monocyclic aromatic ring. A variety of $Ar^2$ aryl groups provide compounds having the desired activity. In particular, $Ar^2$ aryl groups can be benzene, pyridine, pyrazine, pyrimidine, pyridazine, triazine. Each of these rings can be optionally substituted with from one to four $R^8$ substituents.

Within $Ar^1$ and $Ar^2$, variables $R^7$ and $R^8$ represent from one to four substituents on their respective rings, wherein each substituent present can be the same or different from any other substituent. More particularly, $R^7$ substituents are independently selected from the group consisting of halogen, $(C_1-C_8)$alkyl, halo$(C_1-C_8)$alkyl, $-OR^2$, $(C_2-C_8)$alkenyl, $(C_2-C_8)$alkynyl, $(C_3-C_7)$cycloalkyl, $(C_3-C_7)$cycloalkyl$(C_1-C_4)$alkyl, aryl, aryl$(C_1-C_4)$alkyl, $(C_2-C_8)$alkenyl, aryl$(C_2-C_8)$alkynyl, heterocyclyl, heterocyclyl$(C_1-C_4)$alkyl, $-COR^2$, $-CO_2R^2$, $-NR^2R^3$, $-NO_2$, $-CN$, $-S(O)_{r1}R^2$, $-X^1OR^2$, $-X^1COR^2$, $-X^1CO_2R^2$, $-X^1NR^2R^3$, $-X^1NO_2$, $-X^1CN$, and $-X^2S(O)_{r1}R^2$. More particularly, $R^8$ substituents are independently selected from the group consisting of halogen, $(C_1-C_8)$alkyl, halo$(C_1-C_8)$alkyl, $-OR^2$, $(C_2-C_8)$alkenyl, $(C_2-C_8)$alkynyl, $(C_3-C_7)$cycloalkyl, $(C_3-C_7)$cycloalkyl$(C_1-C_4)$alkyl, aryl, aryl$(C_1-C_4)$alkyl, aryl$(C_2-C_8)$alkenyl, aryl$(C_2-C_8)$alkynyl, heterocyclyl, heterocyclyl$(C_1-C_4)$alkyl, $-COR^2$, $-CO_2R^2$, $-NR^2R^3$, $-NO_2$, $-CN$, $-S(O)_{r1}R^2$, $-X^2OR^2$, $-X^2COR^2$, $-X^2CO_2R^2$, $-X^2NR^2R^3$, $-X^2NO_2$, $-X^2CN$, and $-X^2S(O)_{r1}R^2$. Within these designations, each $R^2$ and $R^3$ is a member independently selected from the group consisting of H, $(C_1-C_8)$alkyl, halo$(C_1-C_8)$alkyl, $-X^3OR^9$, aryl, aryl$(C_1-C_4)$alkyl, and heteroaryl, or optionally, if both present on the same substituent, may be joined together to form a three- to eight-membered ring system. $R^9$ is a member selected from the group consisting of H, $(C_1-C_8)$alkyl, halo$(C_1-C_8)$alkyl, aryl, aryl$(C_1-C_4)$alkyl, and heteroaryl. Each $X^1$, $X^2$, and $X^3$ is a member independently selected from the group consisting of $(C_1-C_4)$alkylene, $(C_2-C_4)$alkenylene, and $(C_2-C_4)$alkynylene. The subscript r1 is an integer of from 0 to 2.

Returning to formula I, L represents a covalent bond or a linking group having from one to six main chain atoms and having the formula —$Y^1_{m1}Y^2_{m2}Y^3_{m3}$— wherein L can be attached to any available ring member of $Ar^2$.

Similarly, K represents either a covalent bond or a linking group having from one to six main chain atoms and having the formula —$Y^4_{m4}Y^5_{m5}Y^6_{m6}$— wherein K can be attached to any available ring member of $Ar^2$. Each $Y^1$, $Y^2$, $Y^3$, $Y^4$, $Y^5$, and $Y^6$ represents a member independently selected from the group consisting of $(CR^4R^5)_p$, C=O, C=$ONR^2$, C=$NOR^2$, $NR^2$C=O, $NR^2$, O, $S(O)_{r2}$, $NR^2SO_2$, and $SO_2NR^2$; wherein $R^2$ and $R^3$ are as defined above. Each $R^4$ and $R^5$ are members independently selected from the group consisting of H, halogen, ($C_1$-$C_8$)alkyl, halo($C_1$-$C_8$)alkyl, $OR^2$, aryl, heteroaryl, and aryl($C_1$-$C_4$)alkyl, or optionally, if both present on the same substituent, may be joined together to form a three- to eight-membered ring system, or if present on adjacent carbon atoms are combined to form a double bond or triple bond between the atoms to which they are attached. Each subscript m1-m6 is an integer of from 0 to 1, the subscript r2 is an integer of from 0 to 2; and the subscript p is an integer of from 1 to 2. More preferably the subscript m1 and m6 is 0, the subscript r2 is 0; and the subscripts m2-m4 are 1. More preferably the subscript p is 1.

Returning to formula I, Z is selected from the group consisting of $CH_2OR^6$, $CO_2R^6$, CN, tetrazol-5-yl, $CONHSO_2R^2$ and CHO; wherein $R^6$ is a member selected from the group consisting of H, ($C_1$-$C_8$)alkyl, halo($C_1$-$C_8$)alkyl, —$X^4OR^2$, —$X^4NR^2R^3$, ($C_2$-$C_8$)alkenyl, ($C_3$-$C_7$)cycloalkyl, heterocyclyl, aryl($C_1$-$C_4$)alkyl, and aryl($C_2$-$C_8$)alkenyl. $X^4$ is a member independently selected from the group consisting of ($C_1$-$C_4$)alkylene, ($C_2$-$C_4$)alkenylene, and ($C_2$-$C_4$)alkynylene. $R^2$ and $R^3$ are as defined above.

The symbol $R^1$ represents a member selected from the group consisting of H, halogen, ($C_1$-$C_8$)alkyl, halo($C_1$-$C_8$)alkyl, ($C_3$-$C_7$)cycloalkyl, ($C_3$-$C_7$)cycloalkyl($C_1$-$C_4$)alkyl, aryl, aryl($C_1$-$C_4$)alkyl, heterocyclyl, and heterocyclyl($C_1$-$C_4$)alkyl.

In addition to compounds having formula I above, the present invention further includes all salts thereof, and particularly, pharmaceutically acceptable salts thereof. Still further, the invention includes compounds that are single isomers of the above formula (e.g., single enantiomers of compounds having a single chiral center), as well as solvate, hydrate, and prodrug forms thereof.

In other aspects, the present invention provides compositions containing one or more compounds of Formula I, as well as methods for the use of such compounds and compositions, either alone or in combination with other pharmaceutical agents as provided in detail below. In particular, the present invention provides methods of using the compounds and/or compositions for the treatment of Type 2 diabetes, hyperinsulemia, hyperlipidemia, hyperuricemia, hypercholesteremia, atherosclerosis, one or more risk factors for cardiovascular disease, Syndrome X, hypertriglyceridemia, hyperglycemia, obesity, eating disorders, and suppressing appetite. In addition, the present invention provides methods of using the compounds and/or compositions for the modulation of peroxisome proliferators activated receptor, insulin resistance, fibrinogen levels, leptin levels, LDLc shifting LDL particle size from small dense to normal dense LDL. Additionally, the present invention provides methods of using the compounds and/or compositions for the treatment of diseases modulated by any of the isoforms of peroxisome proliferation activated receptor (PPAR).

DETAILED DESCRIPTION OF THE INVENTION

Abbreviations and Definitions

Figure 1A:
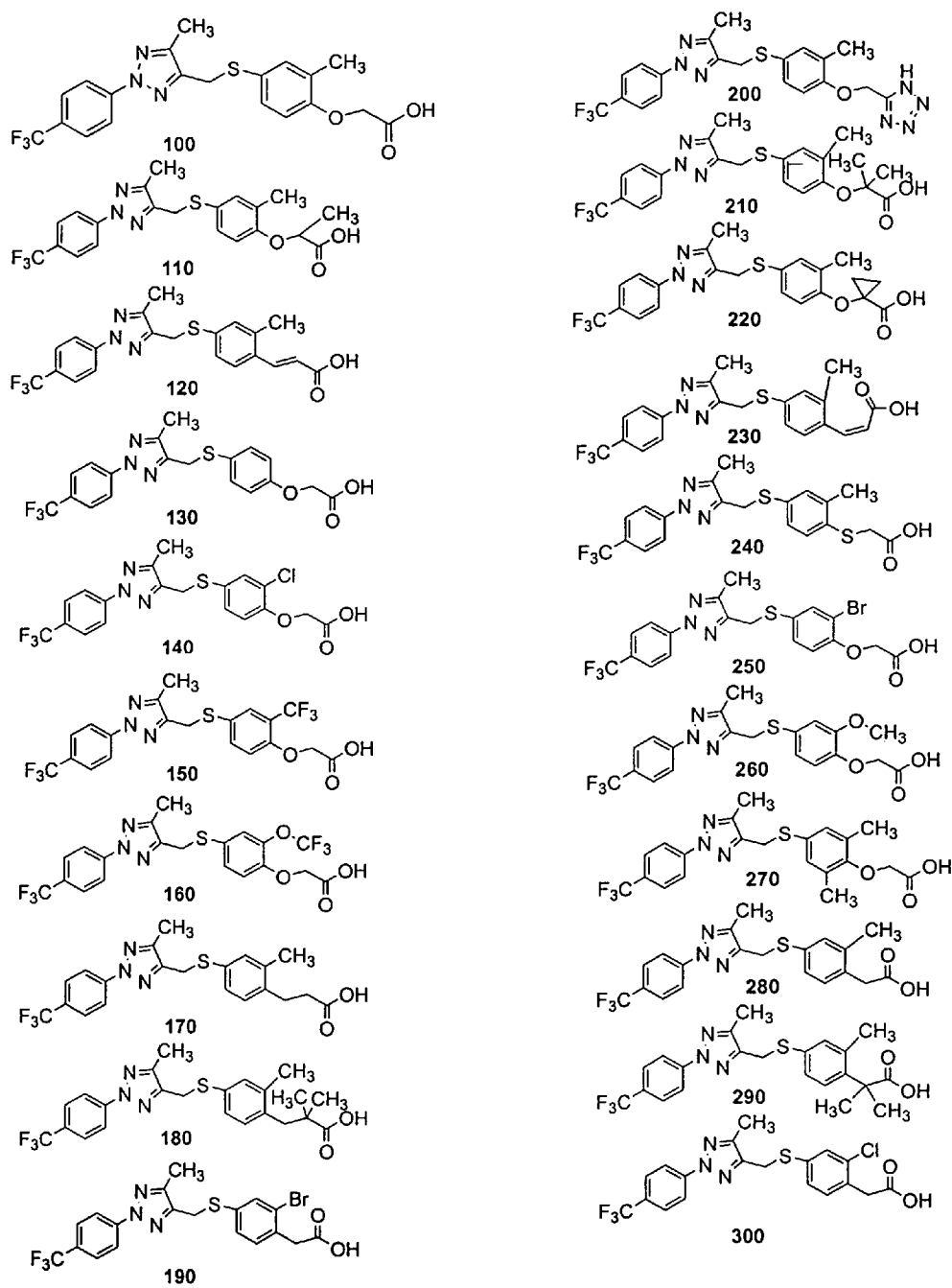
FIG. 1A-E illustrate a variety of preferred compounds of the invention.

The abbreviations used herein are conventional, unless otherwise defined:

AcOH: acetic acid; BPO: benzoyl peroxide; $CBr_4$: tetrabromomethane; $Cs_2CO_3$: cesium carbonate; $CH_2Cl_2$: dichloromethane; $CuCl_2$: copper chloride; DIBAL: diisobutylaluminum hydride; DMSO: dimethyl sulfoxide; EtOAc: ethyl acetate; $H_2$: hydrogen; $H_2O$: water; HBr: hydrogen bromide; HCl: hydrogen chloride; KCN: potassium cyanide; $LiAlH_4$: lithium aluminum hydride; LiOH: lithium hydroxide; MeCN: acetonitrile; MeOH: methanol; $N_2$: nitrogen; $Na_2CO_3$: sodium carbonate; $NaHCO_3$: sodium bicarbonate; $NaNO_2$: sodium nitrite; NaOH: sodium hydroxide; $Na_2S_2O_3$: sodium bisulfate; $Na_2SO_4$: sodium sulfate; NBS: N-bromosuccinamide; $NH_4Cl$: ammonium chloride; $NH_4OAc$: ammonium acetate; NMR: nuclear magnetic resonance; Pd/C: palladium on carbon; $PPh_3$: triphenyl phosphine; $SOCl_2$: thionyl chloride; THF: tetrahydrofuran; TLC: thin layer chromatography.

Unless otherwise stated, the following terms used in the specification and claims have the meanings given below:

"Alkyl" refers to a linear saturated monovalent hydrocarbon radical or a branched saturated monovalent hydrocarbon radical having the number of carbon atoms indicated in the prefix. For example, ($C_1$-$C_8$)alkyl is meant to include methyl, ethyl, n-propyl, 2-propyl, n-butyl, 2-butyl, tert-butyl, pentyl, and the like. For each of the definitions herein (e.g., alkyl, alkenyl, alkoxy, araalkyloxy), when a prefix is not included to indicate the number of main chain carbon atoms in an alkyl portion, the radical or portion thereof will have six or fewer main chain carbon atoms.

"Alkylene" refers to a linear saturated divalent hydrocarbon radical or a branched saturated divalent hydrocarbon radical having the number of carbon atoms indicated in the prefix. For example, ($C_1$-$C_6$)alkylene is meant to include methylene, ethylene, propylene, 2-methylpropylene, pentylene, and the like.

"Alkenyl" refers to a linear monovalent hydrocarbon radical or a branched monovalent hydrocarbon radical having the number of carbon atoms indicated in the prefix and containing at least one double bond, but no more than three double bonds. For example, ($C_2$-$C_6$)alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, ($C_2$-$C_6$)alkynyl is meant to include ethynyl, propynyl, and the like.

"Alkoxy", "aryloxy" or "araalkyloxy" refers to a radical —OR wherein R is an alkyl, aryl or arylalkyl, respectively, as defined herein, e.g., methoxy, phenoxy, benzyloxy, and the like.

"Aryl" refers to a monovalent monocyclic or bicyclic aromatic hydrocarbon radical of 6 to 10 ring atoms which is substituted independently with one to four substituents, preferably one, two, or three substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$—CONR$^x$R$^y$ (where n is an integer from 0 to 5, R' and R" are independently hydrogen or alkyl, and R$^x$ and R$^y$ are independently selected from hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the substituted forms thereof.

"Araalkyl" or "Aryl($C_1$-$C_x$)alkyl" refers to the radical —R$^x$R$^y$ where R$^x$ is an alkylene group (having eight or fewer main chain carbon atoms) and R$^y$ is an aryl group as defined above. Thus, "araalkyl" refers to groups such as, for example, benzyl, phenylethyl, 3-(4-nitrophenyl)-2-methylbutyl, and the like. Similarly, "Araalkenyl" means a radical —R$^x$R$^y$ where Rx is an alkenylene group (an alkylene group having one or two double bonds) and R$^y$ is an aryl group as defined above, e.g., styryl, 3-phenyl-2-propenyl, and the like.

"Cycloalkyl" refers to a monovalent cyclic hydrocarbon radical of three to seven ring carbons. The cycloalkyl group may have one double bond and may also be optionally substituted independently with one, two, or three substituents selected from alkyl, optionally substituted phenyl, or —C(O)R$^z$ (where R$^z$ is hydrogen, alkyl, haloalkyl, amino, mono-alkylamino, di-alkylamino, hydroxy, alkoxy, or optionally substituted phenyl). More specifically, the term cycloalkyl includes, for example, cyclopropyl, cyclohexyl, cyclohexenyl, phenylcyclohexyl, 4-carboxycyclohexyl, 2-carboxamidocyclohexenyl, 2-dimethylaminocarbonyl-cyclohexyl, and the like.

"Cycloalkyl-alkyl" means a radical —R$^x$R$^y$ wherein R$^x$ is an alkylene group and R$^y$ is a cycloalkyl group as defined herein, e.g., cyclopropylmethyl, cyclohexenylpropyl, 3-cyclohexyl-2-methylpropyl, and the like. The prefix indicating the number of carbon atoms (e.g., $C_4$-$C_{10}$) refers to the total number of carbon atoms from both the cycloalkyl portion and the alkyl portion.

"Haloalkyl" refers to an alkyl group which is substituted with one or more same or different halo atoms, e.g., —$CH_2Cl$, —$CH_2F$, —$CH_2Br$, —$CFClBr$, —$CH_2CH_2Cl$, —$CH_2CH_2F$, —$CF_3$, —$CH_2CF_3$, —$CH_2CCl_3$, and the like, and further includes those alkyl groups such as perfluoroalkyl in which all hydrogen atoms are replaced by fluorine atoms. The prefix "halo" and the term "halogen" when used to describe a substituent, refer to —F, —Cl, —Br and —I.

"Haloalkoxy" refers to an alkoxy group which is substituted with one or more same or different halo atoms, e.g., —$CH_3OCHCl$, —$CH_3OCHF$, —$CH_3OCHBr$, —$CH_3OCHCH_2Cl$, —$CH_3CH_2OCHF$, —$CH_3OCHCF_3$, and the like.

"Heteroalkyl" means an alkyl radical as defined herein with one, two or three substituents independently selected from cyano, —OR$^w$, —NR$^x$R$^y$, and —S(O)$_n$R$^z$ (where n is an integer from 0 to 2), with the understanding that the point of attachment of the heteroalkyl radical is through a carbon atom of the heteroalkyl radical. R$^w$ is hydrogen, alkyl, cycloalkyl, cycloalkyl-alkyl, aryl, araalkyl, alkoxycarbonyl, aryloxycarbonyl, carboxamido, or mono- or di-alkylcarbamoyl. R$^x$ is hydrogen, alkyl, cycloalkyl, cycloalkyl-alkyl, aryl or araalkyl. Ry is hydrogen, alkyl, cycloalkyl, cycloalkyl-alkyl, aryl, araalkyl, alkoxycarbonyl, aryloxycarbonyl, carboxamido, mono- or di-alkylcarbamoyl or alkylsulfonyl. R$^z$ is hydrogen (provided that n is 0), alkyl, cycloalkyl, cycloalkyl-alkyl, aryl, araalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^w$, R$^x$, R$^y$, and R$^z$ can be further substituted by amino, fluorine, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —OR$^w$, —NR$^x$R$^y$, or —S(O)$_n$R$^z$ portions.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or —CR'R")$_n$—CONR$^x$R$^y$ (where n is an integer from 0 to 5, R' and R" are independently hydrogen or alkyl, and R$^x$ and R$^y$ are, independently of each other, hydrogen, alkyl, cycloalkyl, cycloalkyl-alkyl, phenyl or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heterocyclyl" or "cycloheteroalkyl" means a saturated or unsaturated non-aromatic cyclic radical of 3 to 8 ring atoms in which one to four ring atoms are heteroatoms selected from O, NR (where R is independently hydrogen or alkyl) or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, aryl, arylalkyl, heteroaryl, heteroarylalkyl, cycloalkyl, cycloalkyl-alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —(CR'R")$_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —(CR'R")$^n$—CONR$^x$R$^y$ (where n is an integer from 0 to 5, R' and R" are independently hydrogen or alkyl, R$^x$ and R$^y$ are, independently of each other, hydrogen, alkyl, cycloalkyl, cycloalkylalkyl, phenyl or phenylalkyl). More specifically the term heterocyclyl includes, but is not limited to, pyridyl, tetrahydropyranyl, piperidino, N-methylpiperidin-3-yl, piperazino, N-methylpyrrolidin-3-yl, 3-pyrrolidino, 2-pyrrolidon-1-yl, furyl, quinolyl, morpholino, thienyl, benzothienyl, thiomorpholino, thiomorpholino-1-oxide, thiomorpholino-1,1-dioxide, pyrrolidinyl, and the derivatives thereof. The prefix indicating the number of carbon atoms (e.g., $C_3$-$C_{10}$) refers to the total number of carbon atoms in the portion of the cycloheteroalkyl or heterocyclyl group exclusive of the number of heteroatoms.

"Heterocyclylalkyl" or "Cycloheteroalkyl-alkyl" means a radical —R$^x$R$^y$ where R$^x$ is an alkylene group and R$^y$ is a heterocyclyl group as defined herein, e.g., tetrahydropyran-2-ylmethyl, 4-(4-substituted-phenyl)piperazin-1-ylmethyl, 3-piperidinylethyl, and the like.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or di-substituted with an alkyl group and situations where the heterocyclo group is not substituted with the alkyl group.

"Optionally substituted" means a ring which is optionally substituted independently with substituents.

For each of the definitions above, the term "di-alkylamino" refers to an amino moiety bearing two alkyl groups that can be the same, or different.

As used herein, the term "carboxylic acid equivalent" refers to those moieties that are used as equivalents for a carboxylic acid moiety. Such groups are generally known to one of skill in the art (see, for example, The Practice of Medicinal Chemistry; Wermuth, C. G., ed., Academic Press, New York, 1996, page 203). Suitable isosteres or equivalents include —C(O)NHSO$_2$R wherein R can be alkyl, haloalkyl, heteroalkyl, araalkyl, aryl, heteroaryl, heterocyclyl, alkoxy, haloalkoxy, aryloxy, alkylamino, haloalkylamino, dialkylamino, dihaloalkylamino, arylamino, diarylamino, araalkylamino, diaraalkylamino or other groups to provide an overall acidic character to the moiety; sulfonic acids; sulfinic acids; phosphonic acids; phosphinic acids; activated sulfonamides (e.g., —SO$_2$NHX wherein X is an electron withdrawing group relative to an alkyl group, such as an acyl group or aryl group; activated carboxamides (e.g., —C(O)NHCN); hydroxamic acids (—C(O)NHOH); acidic heterocycles or substituted heterocycles (e.g., tetrazoles, triazoles, hydroxypyrazoles, hydroxyoxazoles, hydroxythiadiazoles); and acidic alcohols (e.g., —C(CF$_3$)$_2$OH or —CH(CF$_3$)OH). The term "carboxylic acid equivalent" also refers to those moieties that may be converted into a carboxylic acid moiety in vivo. Such groups are generally known to one of skill in the art. While it is recognized that these groups initially may be non-acidic, suitable in vivo equivalents include aldehydes (CHO) and alcohols CH$_2$OH and esters CH$_2$OR wherein R can be alkyl, alkenyl, cycloalkyl, haloalkyl, heteroalkyl, araalkyl, aryl, heteroaryl, heterocyclyl, arylalkyl, arylalkenyl, alkoxy, haloalkoxy, aryloxy, alkylamino, haloalkylamino, dialkylamino, dihaloalkylamino, arylamino, diarylamino, araalkylamino, diaraalkylamino, or other groups that can be easily cleaved to provide a hydroxyl group that can be oxidized in vivo to provide a carboxylic acid.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992).

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like.

"Prodrugs" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, carbamates (e.g., N,N-dimethylaminocarbonyl) of hydroxy functional groups in compounds of Formula I, and the like.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 2nd ed. 1991) and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes:
(1) preventing the disease, i.e., causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "patient" means all mammals, including humans. Examples of patients include, but are not limited to, humans, cows, dogs, cats, goats, sheep, pigs and rabbits.

The term "mammal" includes, without limitation, humans, domestic animals (e.g., dogs or cats), farm animals (cows, horses, or pigs), monkeys, rabbits, mice, and laboratory animals.

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M. *J. Basic & Clin. Phys. & Pharm.* (1998) 9: 387-406 and Flier, J. *Ann Rev. Med.* (1983) 34: 145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plasminogen activator inhibitor-1), has been referred to as "Syndrome X" (see, e.g., Reaven, G. M. *Physiol. Rev.* (1995) 75: 473-486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes.

The term "secondary diabetes" is diabetes resulting from other identifiable etiologies which include: genetic defects of β cell function (e.g., maturity onset-type diabetes of youth, referred to as "MODY," which is an early-onset form of Type 2 diabetes with autosomal inheritance; see, e.g., Fajans, S. et al. *Diabet. Med.* (1996) (9 Suppl 6): S90-5 and Bell, G. et al., *Annu. Rev. Physiol.* (1996) 58: 171-86; genetic defects in insulin action; diseases of the exocrine pancreas (e.g., hemochromatosis, pancreatitis, and cystic fibrosis); certain endocrine diseases in which excess hormones interfere with insulin action (e.g., growth hormone in acromegaly and cortisol in Cushing's syndrome); certain drugs that suppress insulin secretion (e.g., phenyloin) or inhibit insulin action (e.g., estrogens and glucocorticoids); and diabetes caused by infection (e.g., rubella, Coxsackie, and CMV); as well as other genetic syndromes.

The guidelines for diagnosis for Type 2 diabetes, impaired glucose tolerance, and gestational diabetes have been outlined by the American Diabetes Association (see, e.g., The Expert Committee on the Diagnosis and Classification of Diabetes Mellitus, Diabetes Care, (1999) Vol 2 (Suppl 1): S5-19).

The term "hyperinsulinemia" refers to the presence of an abnormally elevated level of insulin in the blood. Similarly, the term "hyperuricemia" refers to the presence of an abnormally elevated level of uric acid in the blood. The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "secretagogue" means a substance or compound that stimulates secretion. For example, an insulin secretagogue is a substance or compound that stimulates secretion of insulin.

The term "hemoglobin" or "Hb" refers to a respiratory pigment present in erythrocytes, which is largely responsible for oxygen transport. A hemoglobin molecule comprises four polypeptide subunits (two α chain systems and two β chain systems, respectively). Each subunit is formed by association of one globin protein and one heme molecule which is an iron-protoporphyrin complex. The major class of hemoglobin found in normal adult hemolysate is adult hemoglobin (referred to as "HbA"; also referred to $HbA_0$ for distinguishing it from glycated hemoglobin, which is referred to as "$HbA_1$," described infra) having $α_2β_2$ subunits. Trace components such as $HbA_2$ ($α_2δ_2$) can also be found in normal adult hemolysate.

Among classes of adult hemoglobin HbAs, there is a glycated hemoglobin (referred to as "$HbA_1$," or "glycosylated hemoglobin"), which may be further fractionated into $HbA_{1a1}$, $HbA_{1a2}$, $HbA_{1b}$, and $HbA_{1c}$ with an ion exchange resin fractionation. All of these subclasses have the same primary structure, which is stabilized by formation of an aldimine (Schiff base) by the amino group of N-terminal valine in the β subunit chain of normal hemoglobin HbA and glucose (or, glucose-6-phosphate or fructose) followed by formation of ketoamine by Amadori rearrangement.

The term "glycosylated hemoglobin" (also referred to as "$HbA_{1c}$,", "GHb", "hemoglobin-glycosylated", "diabetic control index" and "glycohemoglobin"; hereinafter referred to as "hemoglobin $A_{1c}$") refers to a stable product of the nonenzymatic glycosylation of the β-chain of hemoglobin by plasma glucose. Hemoglobin $A_{1c}$ comprises the main portion of glycated hemoglobins in the blood. The ratio of glycosylated hemoglobin is proportional to blood glucose level. Therefore, hemoglobin $A_{1c}$ rate of formation directly increases with increasing plasma glucose levels. Since glycosylation occurs at a constant rate during the 120-day lifespan of an erythrocyte, measurement of glycosylated hemoglobin levels reflect the average blood glucose level for an individual during the preceding two to three months. Therefore determination of the amount of glycosylated hemoglobin $HbA_{1c}$ can be a good index for carbohydrate metabolism control. Accordingly, blood glucose levels of the last two months can be estimated on the basis of the ratio of $HbA_{1c}$ to total hemoglobin Hb. The analysis of the hemoglobin $A_{1c}$ in blood is used as a measurement enabling long-term control of blood glucose level (see, e.g., Jain, S. et al., *Diabetes* (1989) 38: 1539-1543; Peters A. et al., *JAMA* (1996) 276: 1246-1252).

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See.e.g., Kaplan, R. M. et al., "Cardiovascular diseases" in HEALTH AND HUMAN BEHAVIOR, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels. Similarly, the term "antiuricemic" refers to the lowering of excessive uric acid concentrations in blood to desired levels.

The term "modulate" refers to the treating, prevention, suppression, enhancement or induction of a function or condition. For example, the compounds of the present invention can modulate hyperlipidemia by lowering cholesterol in a human, thereby suppressing hyperlipidemia.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small of the intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form the low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/ or elevated levels of lipoproteins (e.g., elevated levels of LDL, VLDL and depressed levels of HDL).

Exemplary Primary Hyperlipidemia include, but are not limited to, the following:

(1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;
(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;
(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;
(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;
(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and
(6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of Type 1 diabetes, Type 2 diabetes, Cushing's syndrome, hypothroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index (BMI) greater than 27.8 kg/m2 for men and 27.3 kg/m2 for women (BMI equals weight (kg)/height (m2). Obesity is linked to a variety of medical conditions including diabetes and hyperlipidemia. Obesity is also a known risk factor for the development of Type 2 diabetes (See, e.g., Barrett-Conner, E. *Epidemol. Rev.* (1989) 11: 172-181; and Knowler, et al. *Am. J. Clin. Nutr.* (1991) 53:1543-1551).

General

The present invention derives from the discovery that compounds of Formula I are useful in treating or controlling a number of diseases associated with glucose metabolism, lipid metabolism and insulin secretion. More particularly, the compounds of the invention are useful in treating Type 2 diabetes, hyperinsulemia, hyperlipidemia, hyperuricemia, hypercholesteremia, atherosclerosis, one or more risk factors for cardiovascular disease, Syndrome X, hypertriglyceridemia, hyperglycemia, obesity, eating disorders, and suppressing appetite. Without intending to be bound by theory, it is considered that the compounds of Formula I operate via modulation of receptor interactions associated with one or more isoforms of PPAR. As a result, the compounds will likely have utility in treating other diseases states or conditions associated with PPAR.

Compounds

In one aspect, the present invention provides compounds having the formula:

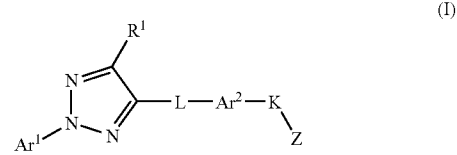

wherein $Ar^1$ represents a monocyclic or bicyclic aromatic ring system selected from the group consisting of phenyl, naphthyl, imidazolyl, benzimidazoyl, pyrrolyl, indolyl, thienyl, benzothienyl, furanyl, benzofuranyl, and benzodioxole.

$Ar^2$ represents 6-membered monocyclic aromatic ring selected from the group consisting of benzene, pyridine, pyrazine, pyrimidine, pyridazine, and triazine.

Returning to Formula I, $Ar^1$ and $Ar^2$ may have substituents on their respective rings, wherein each substituted present can be the same or different from any other substituent. More particularly, $Ar^1$ may have from 0 to 4 substituents, more preferably from 0 to 3 substituents, and still more preferably, 0, 1 or 2 $R^7$ substituents. $R^7$ substituents are independently selected from the group consisting of halogen, $(C_1-C_8)$alkyl, halo$(C_1-C_8)$alkyl, $-OR^2$, $(C_2-C_8)$alkenyl, $(C_2-C_8)$alkynyl, $(C_3-C_7)$cycloalkyl, $(C_3-C_7)$cycloalkyl$(C_1-C_4)$alkyl, aryl, aryl$(C_1-C_4)$alkyl, aryl$(C_2-C_8)$alkenyl, aryl$(C_2-C_8)$alkynyl, heterocyclyl, heterocyclyl$(C_1-C_4)$alkyl, $-COR^2$, $-CO_2R^2$, $-NR^2R^3$, $-NO_2$, $-CN$, $-S(O)_{r1}R^2$ $-X^1OR^2$, $-X^1CO_2R^2$, $-X^1NR^2R^3$, $-X^1NO_2$, $-X^1CN$, and $-X^2S(O)_{r1}R^2$.

$Ar^2$ may have from 0 to 4 substituents, more preferably from 0 to 3 substituents, and still more preferably, 0, 1 or 2 $R^8$ substituents. $R^8$ substituents are independently selected from the group consisting of halogen, $(C_1-C_8)$alkyl, halo$(C_1-C_8)$alkyl, $-OR^2$, $(C_2-C_8)$alkenyl, $(C_2-C_8)$alkynyl, $(C_3-C_7)$cycloalkyl, $(C_3-C_7)$cycloalkyl$(C_1-C_4)$alkyl, aryl, aryl$(C_1-C_4)$alkyl, aryl$(C_2-C_8)$alkenyl, aryl$(C_2-C_8)$alkynyl, heterocyclyl, heterocyclyl$(C_1-C_4)$alkyl, $-COR^2$, $-CO_2R^2$, $-NR^2R^3$, $-NO_2$, $-CN$, $-S(O)_{r1}R^2$ $-X^2OR^2$, $-X^2COR^2$, $-X^2CO_2R^2$, $-X^2NR^2R^3$, $-X^2NO_2$, $-X^2CN$, and $-X^2S(O)_{r1}R^2$.

L represents a member selected from the group consisting of a covalent bond and a linking group having from one to six main chain atoms and having the formula $-Y^1_{m1}Y^2_{m2}Y^3_{m3}-$ wherein L can be attached to any available ring member of $Ar^2$; and each $Y^1$, $Y^2$ and $Y^3$ is a member independently selected from the group consisting of $(CR^4R^5)_p$, C=O, C=ONR$^2$, C=NOR$^2$, NR$^2$C=O, NR$^2$, O, S(O)$_{r2}$, NR$^2$SO$_2$, and SO$_2$NR$^2$.

K represents a member selected from the group consisting of a covalent bond and a linking group having from one to six main chain atoms and having the formula $-Y^4_{m4}Y^5_{m5}Y^6_{m6}-$ wherein K can be attached to any available ring member of $Ar^2$ and each $Y^4$, $Y^5$ and $Y^6$ is a member independently selected from the group consisting of $(CR^4R^5)_pC=O$, $C=ONR^2$, $C=NOR^2$, $NR^2C=O$, $NR^2$, O, $S(O)_{r2}$, $NR^2SO_2$, and $SO_2NR^2$.

Z represents a carboxylic acid equivalent and is selected from the group consisting of $CH_2OR^6$, $CO_2R^6$, CN, tetrazol-5-yl, $CONHSO_2R^2$ and CHO.

$R^1$ represents a symbol selected from the group consisting of H, $(C_1-C_8)$alkyl, halo$(C_1-C_8)$alkyl, $(C_3-C_7)$cycloalkyl, $(C_3-C_7)$cycloalkyl$(C_1-C_4)$alkyl, aryl, aryl$(C_1-C_4)$alkyl, heterocyclyl, and heterocyclyl$(C_1-C_4)$alkyl.

Each $R_2$ and $R^3$ represents a member independently selected from the group consisting of H, $(C_1-C_8)$alkyl, halo$(C_1-C_8)$alkyl, $-X^3OR^9$, aryl, aryl$(C_1-C_4)$alkyl, heteroaryl, or optionally, if both present on the same substituent, may be joined together to form a three- to eight-membered ring system.

Each $R^4$ and $R^5$ represents members independently selected from the group consisting of H, $OR^2$, aryl, heteroaryl, and aryl$(C_1-C_4)$alkyl, or optionally, if both present on the same substituent, may be joined together to form a three- to eight-membered ring system, or if present on adjacent carbon atoms are combined to form a double bond or triple bond between the atoms to which they are attached.

$R^6$ is a member selected from the group consisting of H, $(C_1-C_8)$alkyl, halo$(C_1-C_8)$alkyl, $-X^4OR^2$, $-X^4NR^2R^3$, $(C_2-C_8)$alkenyl, $(C_3-C_7)$cycloalkyl, heterocyclyl, aryl$(C_1-C_4)$alkyl and aryl$(C_2-C_8)$alkenyl.

$R^9$ is a member selected from the group consisting of H, $(C_1-C_8)$alkyl, halo$(C_1-C_8)$alkyl, aryl, aryl$(C_1-C_4)$alkyl, and heteroaryl.

Each $X^1$, $X^2$, $X^3$, and $X^4$ is a member independently selected from the group consisting of $(C_1-C_4)$alkyl, $(C_2-C_4)$alkenyl, and $(C_2-C_4)$alkynyl.

The subscripts m1, m2, m3, m4, m5 and m6 are each integers of from 0 to 1; the subscripts r1 and r2 are integers of from 0 to 2; and the subscript p is an integer of from 1 to 2.

In addition to compounds having formula I above, the present invention further includes all salts thereof, and particularly, pharmaceutically acceptable salts thereof. Still further, the invention includes compounds that are single isomers of the above formula (e.g., single enantiomers of compounds having a single chiral center), as well as solvate, hydrate, and prodrug forms thereof.

A number of other groups of embodiments are preferred and are set forth below.

In a first group of embodiments, $Ar^1$ is benzodioxole or phenyl moiety optionally substituted with from one to three $R^7$ substituents independently selected from the group consisting of halogen, halo$(C_1-C_8)$alkyl, heterocyclyl, heterocyclyl$(C_1-C_4)$alkyl, and $-OR^2$.

The $Ar^1$ phenyl group is preferably substituted with from one to three $R^7$ substituents independently selected from halogen, $(C_1-C_4)$haloalkyl, heterocyclyl, heterocyclyl$(C_1-C_4)$alkyl, or $-OR^2$. Further preferred within this embodiment is where $Ar^1$ is

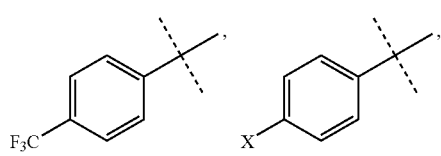

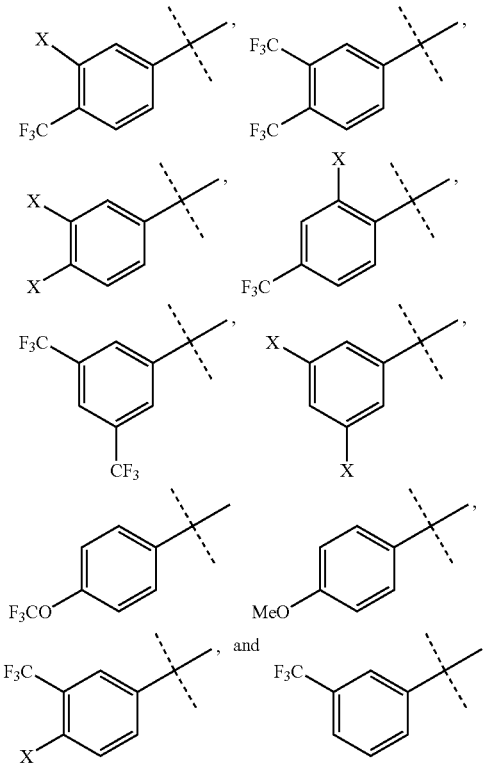

wherein X is a halogen; and still further preferred is where $Ar^1$ is

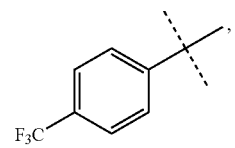

wherein the dashed line indicates the point of attachment to the remainder of the molecule.

Each $R^1$ is preferably, selected from the group consisting of $(C_1-C_8)$alkyl, halo$(C_1-C_8)$alkyl, aryl and heterocyclyl$(C_1-C_4)$alkyl. More preferably $R^1$ is selected from the group consisting of $CH_3$, $CH(CH_3)_2$, $CF_3$, $CF_3CH_2$, phenyl and

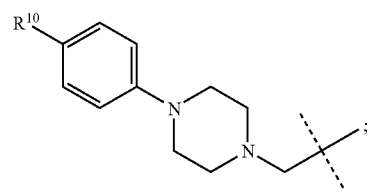

wherein $R^{10}$ is a halogen or $(C_1-C_8)$alkoxy; and the dashed line indicates the point of attachment to the remainder of the molecule. Within this embodiment, $R^{10}$ is preferably Cl, Oi-Pr or $OCH_3$. Most preferably $R^1$ is $CH_3$.

With regard to the linking groups L and K, preferred embodiments are compounds wherein $Y^1$, $Y^2$, $Y^3$, $Y_4$, $Y^5$, and $Y^6$ is a member independently selected from the group consisting of $(CR^4R^5)_p$, C=O, $NR^2$, O, and $S(O)_{r2}$; $R^2$ is H; each $R^4$ and $R^5$ is a member independently selected from the group consisting of H, $(C_1-C_8)$alkyl, halo$(C_1-C_8)$alkyl, or optionally, if both present on the same substituent, may be joined together to form a three- to eight-membered ring system or if present on adjacent carbon atoms are combined to form a double bond or triple bond between the atoms to which they are attached; and r2 is 0. Compounds wherein $Y^1$ is $(CR^4R^5)_p$, $Y^2$ is $CH_2$ or C=O and $Y^3$ is NH, O, or S are further preferred. Compounds within this embodiment wherein $Y^1$ is $CH_2$, $Y^2$ is $(CH_2)_2$ and $Y^3$ is O or S are still further preferred. In another embodiment, compounds wherein at least one of m1, m2, or m3 is 0 are preferred.

L preferably is a member selected from the group consisting of: $CH_2$, $(CH_2)_2$, $-CH_2S$, $CH(CH_3)S$, $C(CH_3)_2S$, $(CH_2)_2S$, $CH(CH_3)CH_2S$, $C(CH_3)_2CH_2S$, $(CH_2)_3S,CH_2O$, $-CH(CH_3)O$, $C(CH_3)_2O$, $(CH_2)_2O$, $CH(CH_3)CH_2O$, $C(CH_3)_2CH_2O$, $(CH_2)_3$ S and (C=O)NH.

In another embodiment, compounds, wherein $Y^4$ is $CR^4R^5$ or O, $Y^5$ is $CR^4R^5$ and m6 is 0 are preferred. Within this embodiment, compounds, wherein K is a member selected from the group consisting of: $-CH_2-$, $-CH(CH_3)-$, $-C(CH_3)_2-$, $-CH=CH_2^E-$, $-CH=CH_2^Z-$, $-CH\equiv CH-$, $-OCH_2-$, $-OCH(CH_3)-$ and $-OC(CH_3)_2-$ are still further preferred. In this embodiment, E represents the entgegen isomer and Z represents the zusamen isomer.

With regard to groups $R^4$ and $R^5$ each is preferably H, $CH_3$, $CF_3$, or joined together to form a three- to six-membered ring system selected from the group consisting of cyclopropyl, cyclobutyl, cyclopentyl and cyclohexyl. Compounds, wherein both $R^4$ and $R^5$ are H are even further preferred.

In other preferred embodiments, Z represents a carboxylic acid or its equivalent selected from the group consisting of $CH_2OR^6$, $CO_2R^6$, CN, tetrazol-5-yl, $CONHSO_2R^2$ and CHO. Preferred carboxylic acid equivalents include tetrazol-5-yl. Still more preferably, Z is a carboxylic acid. A further preferred group of embodiments are those in which Z is $CO_2R^6$.

In one embodiment, $Ar^2$ is preferably selected from the group consisting of: (i) pyridine, optionally substituted with from one to three $R^8$ substituents; (ii) pyrazine, optionally substituted with from one to two $R^8$ substituents; (iii) pyrimidine, optionally substituted with from one to two $R^8$ substituents; (iv) pyridazine, optionally substituted with from one to two $R^8$ substituents; and (v) triazine, optionally substituted with one $R^8$ substituent. In this embodiment each $R^8$ substituent is preferably a member independently selected from the group consisting of halogen, $(C_1-C_8)$alkyl, halo$(C_1-C_8)$alkyl, $(C_3-C_7)$cycloalkyl, aryl, aryl$(C_1-C_4)$alkyl, $-OR^2$, $-X^2OR^2$, heterocyclyl, heterocyclyl$(C_1-C_4)$ $COR^2$, $-CO_2R^2$, $-NR^2R^3$, $-NO_2$, $-X^2NR^2R^3$, $-CN$ and $-S(O)_{r1}R^2$. This embodiment when $Ar^1$ is benzodioxole or phenyl is especially preferred as is this embodiment when L and K include the preferred embodiments above. Within these embodiments, $Ar^2$ is preferably selected from the group having the formula:

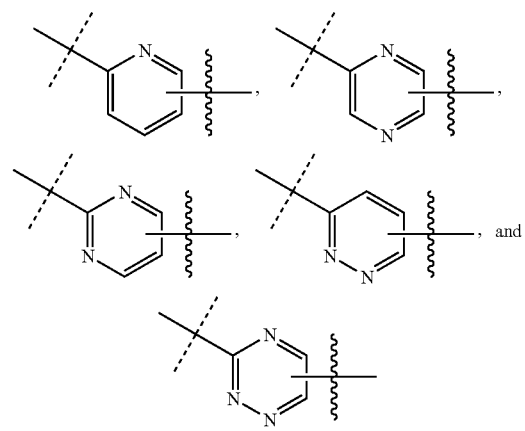

wherein the dashed line indicates the point of attachment to K and the wavy line indicates the point of attachment to L.

Each of the $Ar^2$ groups is preferably substituted with $R^8$ substituents as defined above. When multiple substituents are present, each is selected independently of the others.

Even further preferred are those embodiments in which $Ar^2$ is selected from

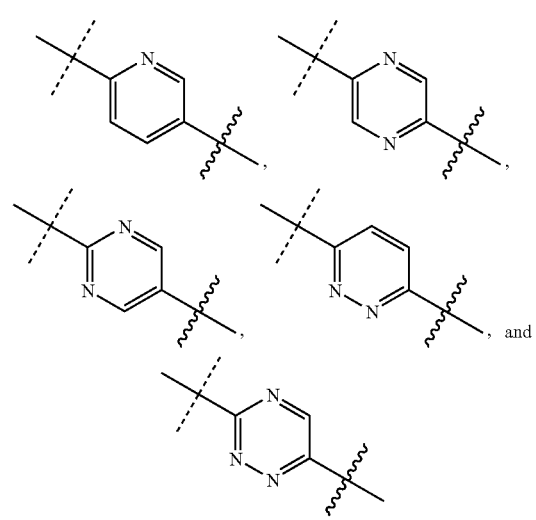

wherein the dashed line indicates the point of attachment to K and the wavy line indicates the point of attachment to L.

In most preferred embodiments, $Ar^2$ is benzene. In this embodiment each $R^8$ substituent is preferably a member independently selected from the group consisting of halogen, $(C_1-C_8)$alkyl, halo$(C_1-C_8)$alkyl, $(C_3-C_7)$cycloalkyl, aryl, aryl$(C_1-C_4)$alkyl, $-OR^2$, $-X^2OR^2$, heterocyclyl, heterocyclyl$(C_1-C_4)$alkyl, $-COR^2$, $-CO_2R^2$, $-NR^2R^3$, $-NO_2$, $-X^2NR^2R^3$, $-CN$ and $-S(O)_{r1}R^2$. This embodiment when $Ar^1$ is benzodioxole or phenyl is especially preferred as is this embodiment when L and K include the preferred embodiments above. Within these embodiments, $Ar^2$ is preferably selected from the group having the formula:

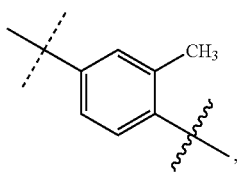

wherein the dashed line indicates the point of attachment to K and the wavy line indicates the point of attachment to L. The compound:

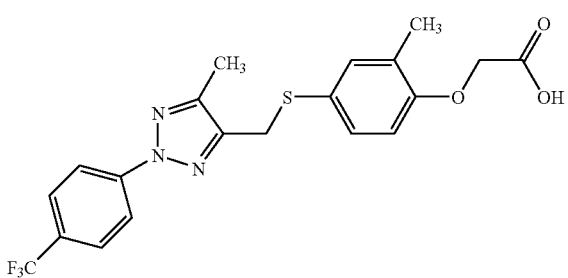

is especially preferred.

Figure 1B:
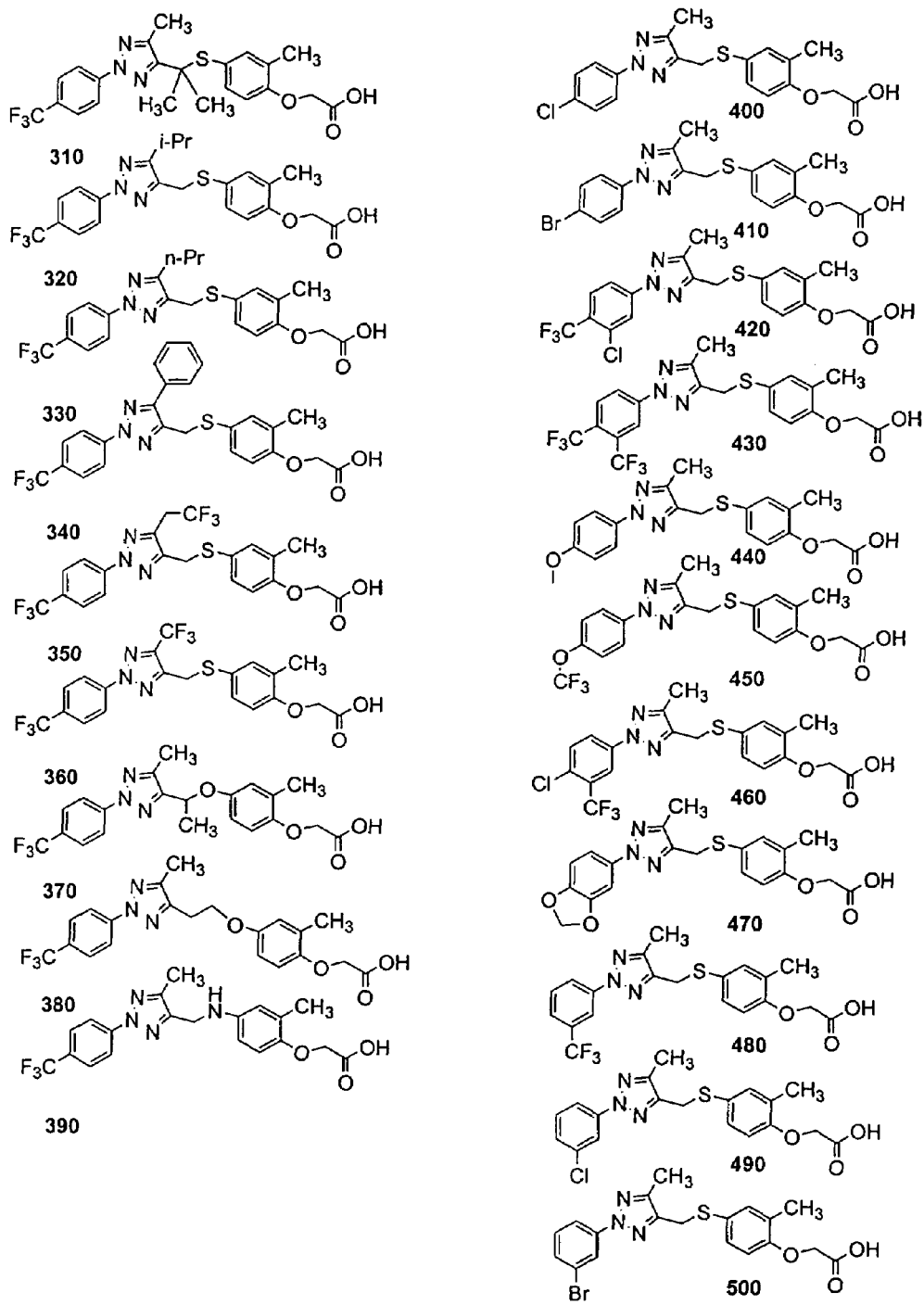
Figure 1C:
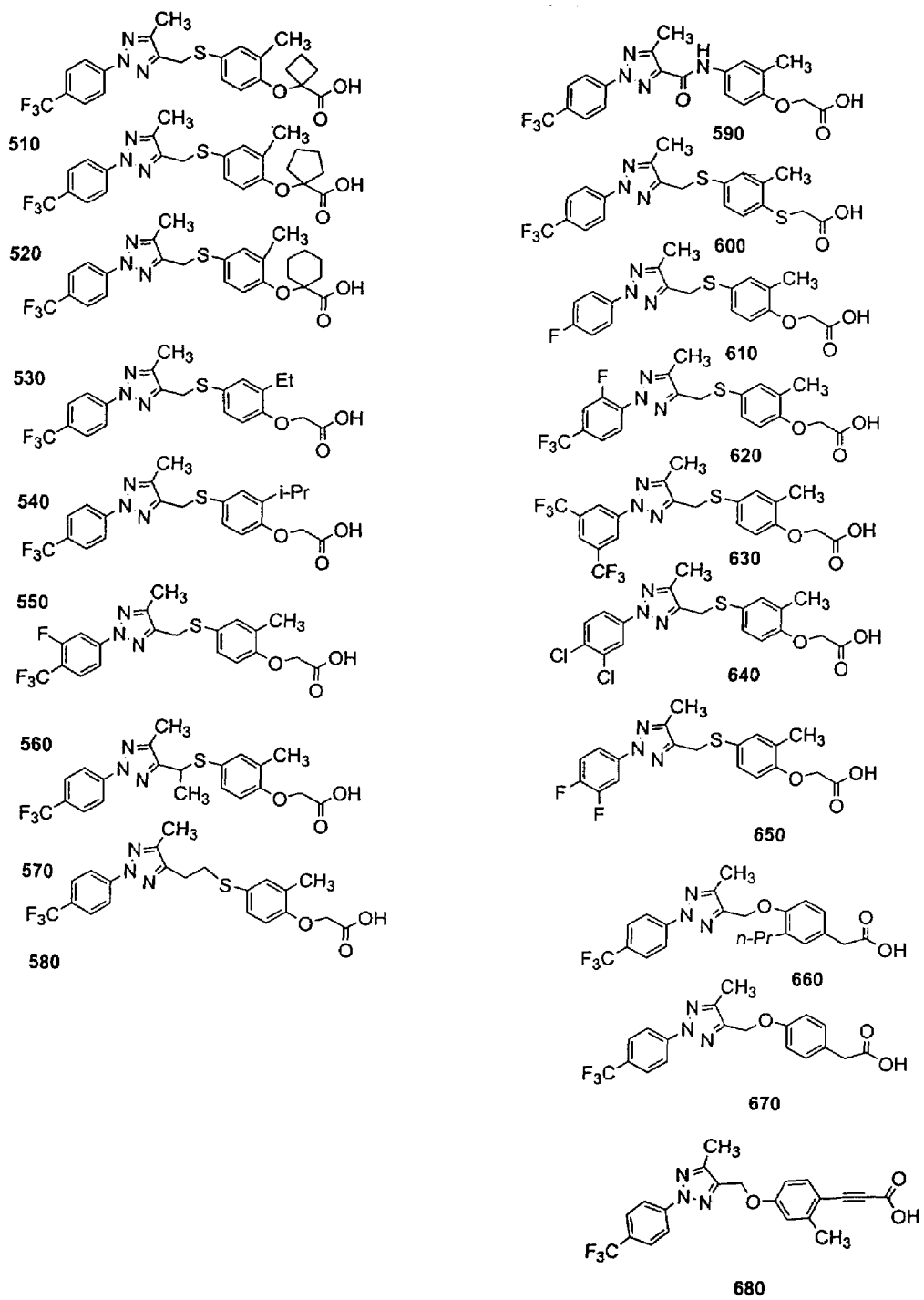
Figure 1D:
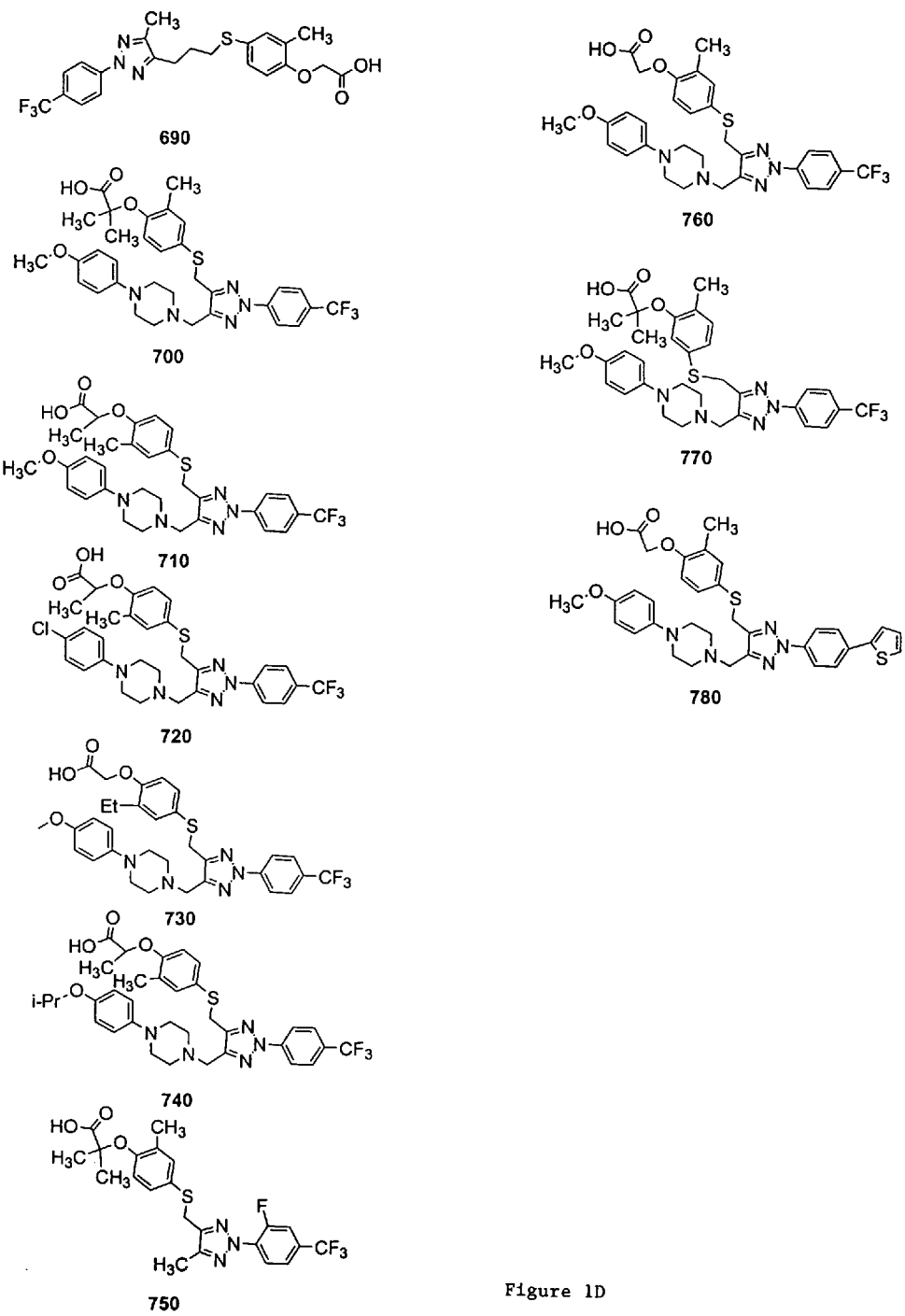
Figure 1E:
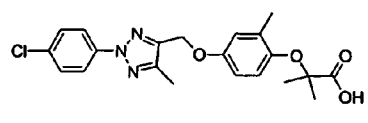
Figure 1E:
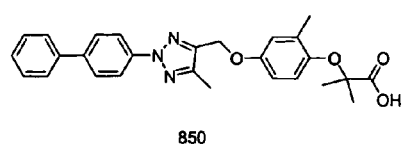
Figure 1E:
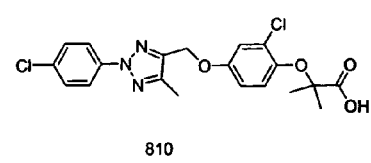
Figure 1E:
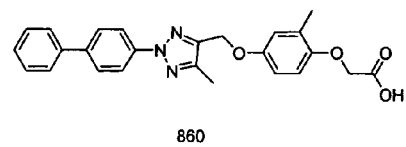
Figure 1E:
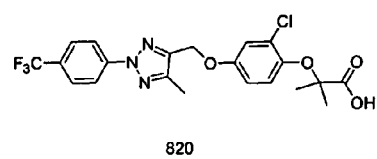
Figure 1E:
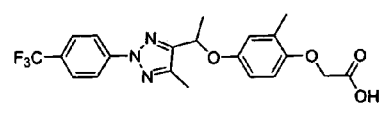
Figure 1E:
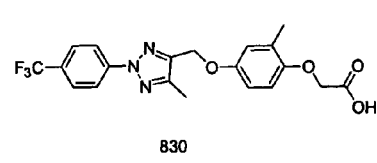
Figure 1E:
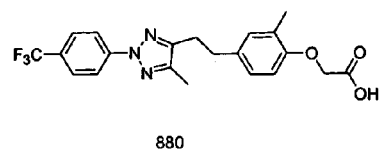
Figure 1E:
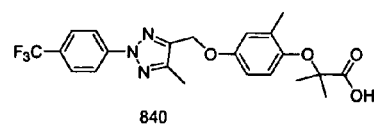
Figure 1E:
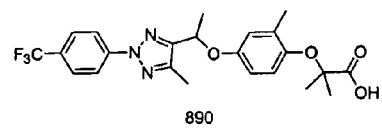

A variety of compounds have the desired activity. In particular, one group of preferred compounds are provided in FIG. 1.

Still other preferred groups of embodiments are provided in the Examples below. Examples of compounds of Formula 1 include:

{2-Methyl-4-[5-methyl-2-(4-trifluoromethyl-phenyl)-2H-[1,2,3]triazol-4-ylmethylsulfanyl]-phenoxy}-acetic acid;

2-{2-Methyl-4-[5-methyl-2-(4-trifluoromethyl-phenyl)-2H-[1,2,3]triazol-4-ylmethylsulfanyl]-phenoxy}-propionic acid;

3-{2-Methyl-4-[5-methyl-2-(4-trifluoromethyl-phenyl)-2H-[1,2,3]triazol-4-ylmethylsulfanyl]-phenyl}-acrylic acid;

{4-[5-Methyl-2-(4-trifluoromethyl-phenyl)-2H-[1,2,3]triazol-4-ylmethylsulfanyl]-phenoxy}-acetic acid;

{2-Chloro-4-[5-methyl-2-(4-trifluoromethyl-phenyl)-2H-[1,2,3]triazol-4-ylmethylsulfanyl]-phenoxy}-acetic acid;

{4-[5-Methyl-2-(4-trifluoromethyl-phenyl)-2H-[1,2,3]triazol-4-ylmethylsulfanyl]-2-trifluoromethyl-phenoxy}-acetic acid;

{4-[5-Methyl-2-(4-trifluoromethyl-phenyl)-2H-[1,2,3]triazol-4-ylmethylsulfanyl]-2-trifluoromethoxy-phenoxy}-acetic acid;

3-{2-Methyl-4-[5-methyl-2-(4-trifluoromethyl-phenyl)-2H-[1,2,3]triazol-4-ylmethylsulfanyl]-phenyl}-propionic acid;

2,2-Dimethyl-3-{2-methyl-4-[5-methyl-2-(4-trifluoromethyl-phenyl)-2H-[1,2,3]triazol-4-ylmethylsulfanyl]-phenyl}-propionic acid;

{2-Bromo-4-[5-methyl-2-(4-trifluoromethyl-phenyl)-2H-[1,2,3]triazol-4-ylmethylsulfanyl]-phenyl}-acetic acid;

5-{2-Methyl-4-[5-methyl-2-(4-trifluoromethyl-phenyl)-2H-[1,2,3]triazol-4-ylmethylsulfanyl]-phenoxymethyl}-1H-tetrazole;

2-Methyl-2-{2-methyl-4-[5-methyl-2-(4-trifluoromethyl-phenyl)-2H-[1,2,3]triazol-4-ylmethylsulfanyl]-phenoxy}-propionic acid;

1-{2-Methyl-4-[5-methyl-2-(4-trifluoromethyl-phenyl)-2H-[1,2,3]triazol-4-ylmethylsulfanyl]-phenoxy}-cyclopropanecarboxylic acid;

3-{2-Methyl-4-[5-methyl-2-(4-trifluoromethyl-phenyl)-2H-[1,2,3]triazol-4-ylmethylsulfanyl]-phenyl}-acrylic acid;

{2-Methyl-4-[5-methyl-2-(4-trifluoromethyl-phenyl)-2H-[1,2,3]triazol-4-ylmethylsulfanyl]-phenylsulfanyl}-acetic acid;

{2-Bromo-4-[5-methyl-2-(4-trifluoromethyl-phenyl)-2H-[1,2,3]triazol-4-ylmethylsulfanyl]-phenoxy}-acetic acid;

{2-Methoxy-4-[5-methyl-2-(4-trifluoromethyl-phenyl)-2H-[1,2,3]triazol-4-ylmethylsulfanyl]-phenoxy}-acetic acid;

{2,6-Dimethyl-4-[5-methyl-2-(4-trifluoromethyl-phenyl)-2H-[1,2,3]triazol-4-ylmethylsulfanyl]-phenoxy}-acetic acid;

{2-Methyl-4-[5-methyl-2-(4-trifluoromethyl-phenyl)-2H-[1,2,3]triazol-4-ylmethylsulfanyl]-phenyl}-acetic acid;

2-Methyl-2-{2-methyl-4-[5-methyl-2-(4-trifluoromethyl-phenyl)-2H-[1,2,3]triazol-4-ylmethylsulfanyl]-phenyl}-propionic acid;

{2-Chloro-4-[5-methyl-2-(4-trifluoromethyl-phenyl)-2H-[1,2,3]triazol-4-ylmethylsulfanyl]-phenyl}-acetic acid;

(2-Methyl-4-{1-methyl-1-[5-methyl-2-(4-trifluoromethyl-phenyl)-2H-[1,2,3]triazol-4-yl]-ethylsulfanyl}-phenoxy)-acetic acid;

{4-[5-Isopropyl-2-(4-trifluoromethyl-phenyl)-2H-[1,2,3]triazol-4-ylmethylsulfanyl]-2-methyl-phenoxy}-acetic acid;

{2-Methyl-4-[5-propyl-2-(4-trifluoromethyl-phenyl)-2H-[1,2,3]triazol-4-ylmethylsulfanyl]-phenoxy}-acetic acid;

{2-Methyl-4-[5-phenyl-2-(4-trifluoromethyl-phenyl)-2H-[1,2,3]triazol-4-ylmethylsulfanyl]-phenoxy}-acetic acid;

{2-Methyl-4-[5-(2,2,2-trifluoro-ethyl)-2-(4-trifluoromethyl-phenyl)-2H-[1,2,3]triazol-4-ylmethylsulfanyl]-phenoxy}-acetic acid;

{2-Methyl-4-[5-trifluoromethyl-2-(4-trifluoromethyl-phenyl)-2H-[1,2,3]triazol-4-ylmethylsulfanyl]-phenoxy}-acetic acid;

(2-Methyl-4-{1-[5-methyl-2-(4-trifluoromethyl-phenyl)-2H-[1,2,3]triazol-4-yl]-ethoxy}-phenoxy)-acetic acid;

(2-Methyl-4-{2-[5-methyl-2-(4-trifluoromethyl-phenyl)-2H-[1,2,3]triazol-4-yl]-ethoxy}-phenoxy)-acetic acid;

(2-Methyl-4-{[5-methyl-2-(4-trifluoromethyl-phenyl)-2H-[1,2,3]triazol-4-ylmethyl]-amino}-phenoxy)-acetic acid;

{4-[2-(4-Chloro-phenyl)-5-methyl-2H-[1,2,3]triazol-4-ylmethylsulfanyl]-2-methyl-phenoxy}-acetic acid;

{4-[2-(4-Bromo-phenyl)-5-methyl-2H-[1,2,3]triazol-4-ylmethylsulfanyl]-2-methyl-phenoxy}-acetic acid;

{4-[2-(3-Chloro-4-trifluoromethyl-phenyl)-5-methyl-2H-[1,2,3]triazol-4-ylmethylsulfanyl]-2-methyl-phenoxy}-acetic acid;

{4-[2-(3,4-Bis-trifluoromethyl-phenyl)-5-methyl-2H-[1,2,3]triazol-4-ylmethylsulfanyl]-2-methyl-phenoxy}-acetic acid;

{4-[2-(4-Methoxy-phenyl)-5-methyl-2H-[1,2,3]triazol-4-ylmethylsulfanyl]-2-methyl-phenoxy}-acetic acid;

{2-Methyl-4-[5-methyl-2-(4-trifluoromethoxy-phenyl)-2H-[1,2,3]triazol-4-ylmethylsulfanyl]-phenoxy}-acetic acid;

{4-[2-(4-Chloro-3-trifluoromethyl-phenyl)-5-methyl-2H-[1,2,3]triazol-4-ylmethylsulfanyl]-2-methyl-phenoxy}-acetic acid;

[4-(2-Benzo[1,3]dioxol-5-yl-5-methyl-2H-[1,2,3]triazol-4-ylmethylsulfanyl)-2-methyl-phenoxy]-acetic acid;

{2-Methyl-4-[5-methyl-2-(3-trifluoromethyl-phenyl)-2H-[1,2,3]triazol-4-ylmethylsulfanyl]-phenoxy}-acetic acid;

{4-[2-(3-Chloro-phenyl)-5-methyl-2H-[1,2,3]triazol-4-ylmethylsulfanyl]-2-methyl-phenoxy}-acetic acid;

{4-[2-(3-Bromo-phenyl)-5-methyl-2H-[1,2,3]triazol-4-ylmethylsulfanyl]-2-methyl-phenoxy}-acetic acid;

1-{2-Methyl-4-[5-methyl-2-(4-trifluoromethyl-phenyl)-2H-[1,2,3]triazol-4-ylmethylsulfanyl]-phenoxy}-cyclobutanecarboxylic acid;

1-{2-Methyl-4-[5-methyl-2-(4-trifluoromethyl-phenyl)-2H-[1,2,3]triazol-4-ylmethylsulfanyl]-phenoxy}-cyclopentanecarboxylic acid;

1-{2-Methyl-4-[5-methyl-2-(4-trifluoromethyl-phenyl)-2H-[1,2,3]triazol-4-ylmethylsulfanyl]-phenoxy}-cyclohexanecarboxylic acid;

{2-Ethyl-4-[5-methyl-2-(4-trifluoromethyl-phenyl)-2H-[1,2,3]triazol-4-ylmethylsulfanyl]-phenoxy}-acetic acid;

{2-Isopropyl-4-[5-methyl-2-(4-trifluoromethyl-phenyl)-2H-[1,2,3]triazol-4-ylmethylsulfanyl]-phenoxy}-acetic acid;

{4-[2-(3-Fluoro-4-trifluoromethyl-phenyl)-5-methyl-2H-[1,2,3]triazol-4-ylmethylsulfanyl]-2-methyl-phenoxy}-acetic acid;

(2-Methyl-4-{1-[5-methyl-2-(4-trifluoromethyl-phenyl)-2H-[1,2,3]triazol-4-yl]-ethylsulfanyl}-phenoxy)-acetic acid;

(2-Methyl-4-{2-[5-methyl-2-(4-trifluoromethyl-phenyl)-2H-[1,2,3]triazol-4-yl]-ethylsulfanyl}-phenoxy)-acetic acid;

(2-Methyl-4-{[5-methyl-2-(4-trifluoromethyl-phenyl)-2H-[1,2,3]triazole-4-carbonyl]-amino}-phenoxy)-acetic acid;

{2-Methyl-4-[5-methyl-2-(4-trifluoromethyl-phenyl)-2H-[1,2,3]triazol-4-ylmethylsulfanyl]-phenylsulfanyl}-acetic acid;

{4-[2-(4-Fluoro-phenyl)-5-methyl-2H-[1,2,3]triazol-4-ylmethylsulfanyl]-2-methyl-phenoxy}-acetic acid;

{4-[2-(2-Fluoro-4-trifluoromethyl-phenyl)-5-methyl-2H-[1,2,3]triazol-4-ylmethylsulfanyl]-2-methyl-phenoxy}-acetic acid;

{4-[2-(3,5-Bis-trifluoromethyl-phenyl)-5-methyl-2H-[1,2,3]triazol-4-ylmethylsulfanyl]-2-methyl-phenoxy}-acetic acid;

{4-[2-(3,4-Dichloro-phenyl)-5-methyl-2H-[1,2,3]triazol-4-ylmethylsulfanyl]-2-methyl-phenoxy}-acetic acid;

{4-[2-(3,4-Difluoro-phenyl)-5-methyl-2H-[1,2,3]triazol-4-ylmethylsulfanyl]-2-methyl-phenoxy}-acetic acid;

{4-[5-Methyl-2-(4-trifluoromethyl-phenyl)-2H-[1,2,3]triazol-4-ylmethoxy]-3-propyl-phenyl}-acetic acid;

{4-[5-Methyl-2-(4-trifluoromethyl-phenyl)-2H-[1,2,3]triazol-4-ylmethoxy]-phenyl}-acetic acid;

{2-Methyl-4-[5-methyl-2-(4-trifluoromethyl-phenyl)-2H-[1,2,3]triazol-4-ylmethoxy]-phenyl}-propinoic acid;

2-{4-[5-[4-(4-Methoxy-phenyl)-piperazin-1-ylmethyl]-2-(4-trifluoromethyl-phenyl)-2H-[1,2,3]triazol-4-ylmethylsulfanyl]-2-methyl-phenoxy}-propionic acid;

2-{4-[5-[4-(4-Chloro-phenyl)-piperazin-1-ylmethyl]-2-(4-trifluoromethyl-phenyl)-2H-[1,2,3]triazol-4-ylmethylsulfanyl]-2-methyl-phenoxy}-propionic acid;

{2-Ethyl-4-[5-[4-(4-methoxy-phenyl)-piperazin-1-ylmethyl]-2-(4-trifluoromethyl-phenyl)-2H-[1,2,3]triazol-4-ylmethylsulfanyl]-phenoxy}-acetic acid;

2-{4-[5-[4-(4-Isopropoxy-phenyl)-piperazin-1-ylmethyl]-2-(4-trifluoromethyl-phenyl)-2H-[1,2,3]triazol-4-ylmethylsulfanyl]-2-methyl-phenoxy}-propionic acid;

2-{4-[2-(2-Fluoro-4-trifluoromethyl-phenyl)-5-methyl-2H-[1,2,3]triazol-4-ylmethylsulfanyl]-2-methyl-phenoxy}-2-methyl-propionic acid;

{4-[5-[4-(4-Methoxy-phenyl)-piperazin-1-ylmethyl]-2-(4-trifluoromethyl-phenyl)-2H-[1,2,3]triazol-4-ylmethylsulfanyl]-2-methyl-phenoxy}-acetic acid;

2-{5-[5-[4-(4-Methoxy-phenyl)-piperazin-1-ylmethyl]-2-(4-trifluoromethyl-phenyl)-2H-[1,2,3]triazol-4-ylmethylsulfanyl]-2-methyl-phenoxy}-2-methyl-propionic acid;

{4-[5-[4-(4-Methoxy-phenyl)-piperazin-1-ylmethyl]-2-(4-thiophen-2-yl-phenyl)-2H-[1,2,3]triazol-4-ylmethylsulfanyl]-2-methyl-phenoxy}-acetic acid;

2-{4-[2-(4-Chloro-phenyl)-5-methyl-2H-[1,2,3]triazol-4-ylmethoxy]-2-methyl-phenoxy}-2-methyl-propionic acid;

2-{2-Chloro-4-[2-(4-chloro-phenyl)-5-methyl-2H-[1,2,3]triazol-4-ylmethoxy]-phenoxy}-2-methyl-propionic acid;

2-{2-Chloro-4-[5-methyl-2-(4-trifluoromethyl-phenyl)-2H-[1,2,3]triazol-4-ylmethoxy]-phenoxy}-2-methyl-propionic acid;

{2-Methyl-4-[5-methyl-2-(4-trifluoromethyl-phenyl)-2H-[1,2,3]triazol-4-ylmethoxy]-phenoxy}-acetic acid;

2-Methyl-2-{2-methyl-4-[5-methyl-2-(4-trifluoromethyl-phenyl)-2H-[1,2,3]triazol-4-ylmethoxy]-phenoxy}-propionic acid;

2-[4-(2-Biphenyl-4-yl-5-methyl-2H-[1,2,3]triazol-4-ylmethoxy)-2-methyl-phenoxy]-2-methyl-propionic acid;

[4-(2-Biphenyl-4-yl-5-methyl-2H-[1,2,3]triazol-4-ylmethoxy)-2-methyl-phenoxy]-acetic acid;

(2-Methyl-4-{1-[5-methyl-2-(4-trifluoromethyl-phenyl)-2H-[1,2,3]triazol-4-yl]-ethoxy}-phenoxy)-acetic acid;

(2-Methyl-4-{2-[5-methyl-2-(4-trifluoromethyl-phenyl)-2H-[1,2,3]triazol-4-yl]-ethyl}-phenoxy)-acetic acid; and 2-Methyl-2-(2-methyl-4-{1-[5-methyl-2-(4-trifluoromethyl-phenyl)-2H-[1,2,3]triazol-4-yl]-ethoxy}-phenoxy)-propionic acid.

Other examples of compounds include:

2-{2-Methyl-4-[5-methyl-2-(4-trifluoromethyl-phenyl)-2H-[1,2,3]triazol-4-ylmethylsulfanyl]-phenoxy}-propionic acid;

{4-[2-(3,5-Bis-trifluoromethyl-phenyl)-5-methyl-2H-[1,2,3]triazol-4-ylmethylsulfanyl]-2-methyl-phenoxy}-acetic acid;

{4-[2-(3,4-Dichloro-phenyl)-5-methyl-2H-[1,2,3]triazol-4-ylmethylsulfanyl]-2-methyl-phenoxy}-acetic acid;

[4-(2-Biphenyl-4-yl-5-methyl-2H-[1,2,3]triazol-4-ylmethylsulfanyl)-2-methyl-phenoxy]-acetic acid;

2-Methyl-2-{2-methyl-4-[5-methyl-2-(4-trifluoromethyl-phenyl)-2H-[1,2,3]triazol-4-ylmethoxy]-phenoxy}-propionic acid;

2-[4-(2-Biphenyl-4-yl-5-methyl-2H-[1,2,3]triazol-4-ylmethoxy)-2-methyl-phenoxy]-2-methyl-propionic acid;

2-Methyl-2-{2-methyl-4-[5-methyl-2-(4-trifluoromethyl-phenyl)-2H-[1,2,3]triazol-4-ylmethylsulfanyl]-phenoxy}-propionic acid;
2-Methyl-2-(2-methyl-4-{1-[5-methyl-2-(4-trifluoromethyl-phenyl)-2H-[1,2,3]triazol-4-yl]-ethoxy}-phenoxy)-propionic acid;
(2-Methyl-4-{2-[5-methyl-2-(4-trifluoromethyl-phenyl)-2H-[1,2,3]triazol-4yl]-ethyl}-phenoxy)-acetic acid;
(2-Methyl-4-{1-methyl-1-[5-methyl-2-(4-trifluoromethyl-phenyl)-2H-[1,2,3]triazol-4-yl]-ethylsulfanyl}-phenoxy)-acetic acid;
(2-Methyl-4-{1-[5-methyl-2-(4-trifluoromethyl-phenyl)-2H-[1,2,3]triazol-4yl]-ethoxy}-phenoxy)-acetic acid;
{4-[5-[4-(4-Methoxy-phenyl)-piperazin-1-ylmethyl]-2-(4-trifluoromethyl-phenyl)-2H-[1,2,3]triazol-4-ylmethylsulfanyl]-2-methyl-phenoxy}-acetic acid and
2-{4-[5-[4-(4-Methoxy-phenyl)-piperazin-1-ylmethyl]-2-(4-trifluoromethyl-phenyl)-2H-[1,2,3]triazol-4-ylmethylsulfanyl]-phenoxy}-2-methyl-propionic acid.

A particularly preferred compound of the invention is: {2-Methyl-4-[5-methyl-2-(4-trifluoromethyl-phenyl)-2H-[1,2,3]triazol-4-ylmethylsulfanyl]-phenoxy}-acetic acid.

All the preferred and most preferred compounds listed above are selective hPPARδ agonists.

Preparation of Compounds of the Invention

The compounds of the present invention can be prepared in a number of ways familiar to one skilled in the art of organic synthesis. The compounds outlined herein can be synthesized using methods generally outlined in Scheme 1, along with methods typically utilized by a synthetic chemist, and combinations or variations of those methods, which are generally known to one skilled in the art of synthetic chemistry. The synthetic route of compounds in the present invention is not limited to the methods outlined below. It is assumed one skilled in the art will be able to use the schemes outlined below to synthesized compounds claimed in this invention. Individual compounds may require manipulation of the condition in order to accommodate various functional groups. A variety of protecting groups generally known to one skilled in the art may be required. Purification, if necessary can be accomplished on a silica gel column eluted with the appropriate organic solvent system. Also, reverse phase HPLC or recrystallization may be employed.

The compounds of formula I can be prepared using methods generally outlined in Scheme 1.

Scheme 1

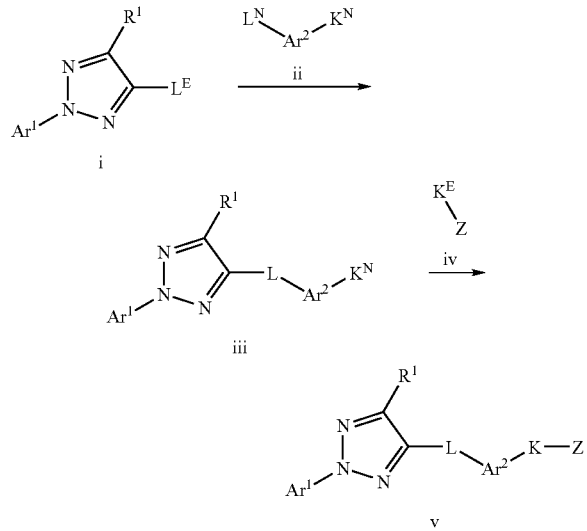

According to Scheme 1, electrophilic, aryl triazoles of formula i (either commercially available or prepared according to known methods or methods outlined below in Scheme 3) are condensed with suitably substituted, nucleophilic aryl compounds ii generally in the presence of solvent and a non-nucleophilic base to provide compound iii. Treatment of iii with a suitably substituted, electrophilic carboxylic acid equivalent iv, generally in the presence of solvent and a non-nucleophilic base, provides the target compound v. Examples of suitable non-nucleophilic bases include, but are not limited to, potassium carbonate, cesium bicarbonate, sodium hydride, and the like.

For example, as shown in Scheme 2 aryl triazole 5A or 5C (prepared as described below) is condensed with 4-mercaptophenol or p-catechol in the presence of cesium carbonate to provide compound 15A. Treatment of 15A with bromo-acetic acid ethyl ester in the presence of sodium hydride provides the target compound 16A. Treatment of ester 16 with lithium hydroxide converts the ester to carboxylic acid compound 100A.

Alternatively, as shown in Scheme 2 bromo-acetic acid ethyl ester is condensed with 4-mercaptophenol or p-catechol in the presence of cesium carbonate to provide compound 15B. Treatment of 15B with $ZnI_2$, DEAD/$PPh_3$ or diamide/$PBu_3$ provides the target compound 16B. Treatment of ester 16B with lithium hydroxide converts the ester to carboxylic acid compound.

Scheme 2

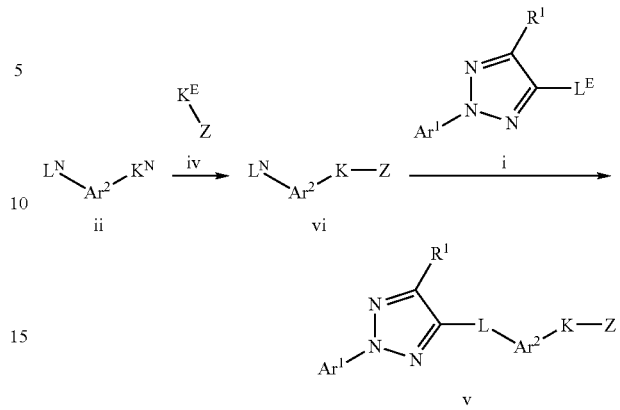

5A $R^1$ = $CH_3$; $R^3$, $R^4$ = H, X = Br
5C $R^1$ = $CH_3$; $R^3$, $R^4$ = H, X = Cl

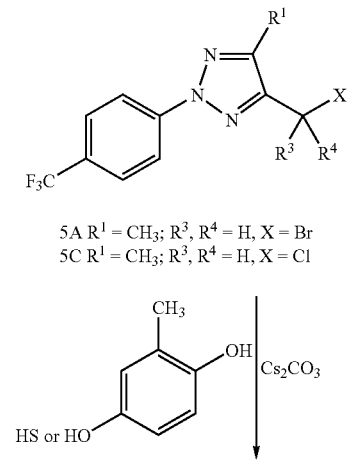

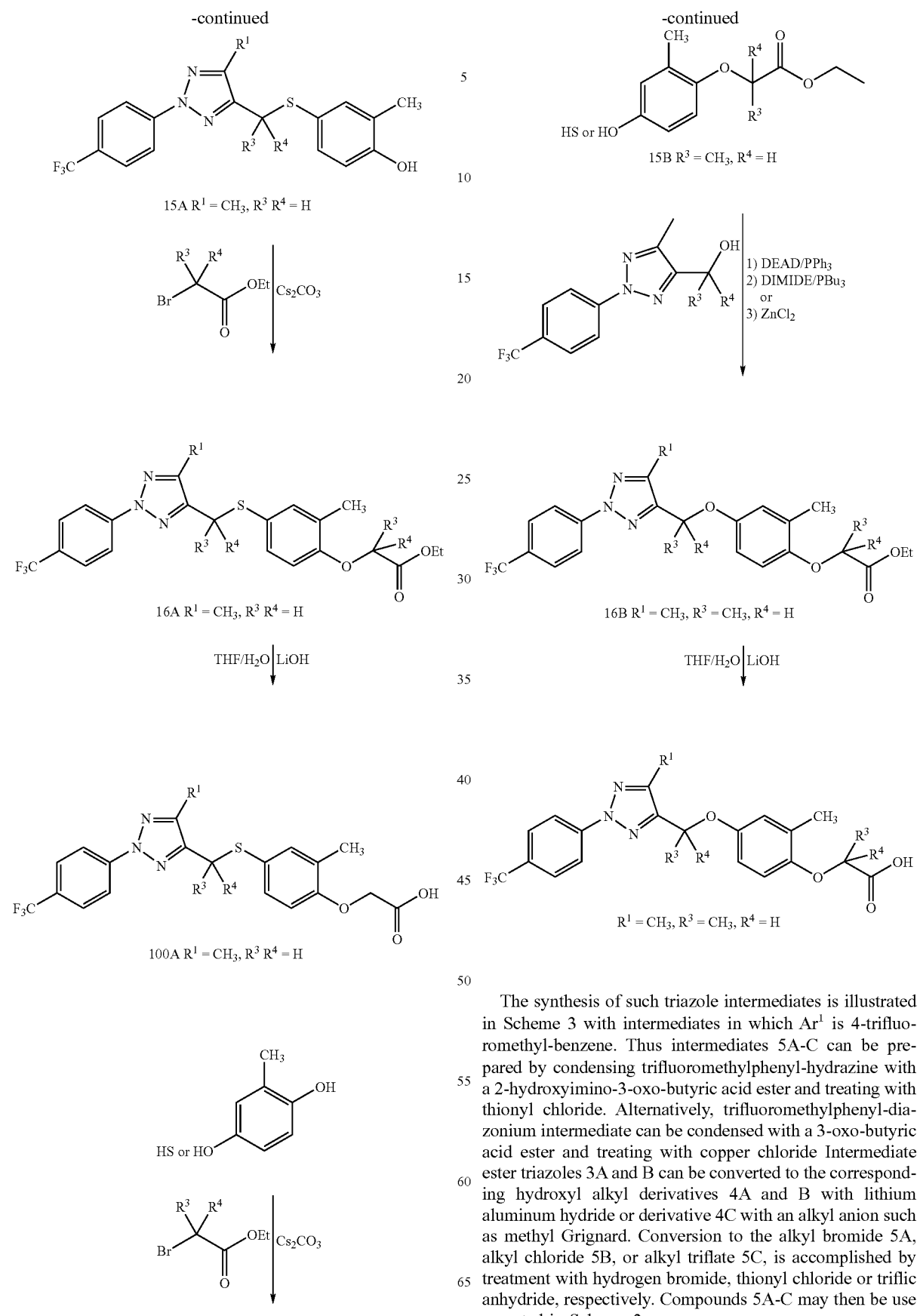

The synthesis of such triazole intermediates is illustrated in Scheme 3 with intermediates in which $Ar^1$ is 4-trifluoromethyl-benzene. Thus intermediates 5A-C can be prepared by condensing trifluoromethylphenyl-hydrazine with a 2-hydroxyimino-3-oxo-butyric acid ester and treating with thionyl chloride. Alternatively, trifluoromethylphenyl-diazonium intermediate can be condensed with a 3-oxo-butyric acid ester and treating with copper chloride Intermediate ester triazoles 3A and B can be converted to the corresponding hydroxyl alkyl derivatives 4A and B with lithium aluminum hydride or derivative 4C with an alkyl anion such as methyl Grignard. Conversion to the alkyl bromide 5A, alkyl chloride 5B, or alkyl triflate 5C, is accomplished by treatment with hydrogen bromide, thionyl chloride or triflic anhydride, respectively. Compounds 5A-C may then be use as noted in Scheme 2.

Scheme 3
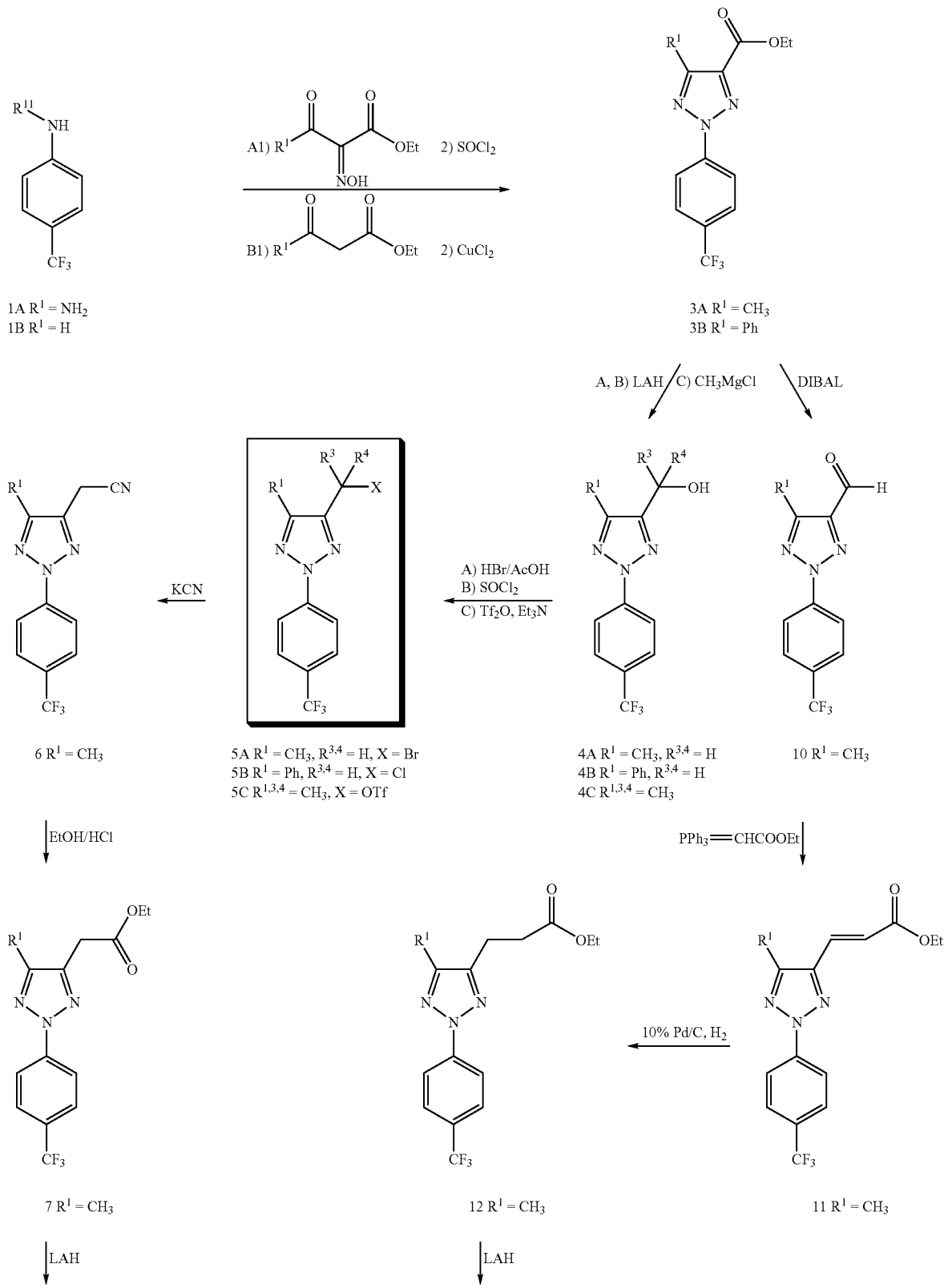

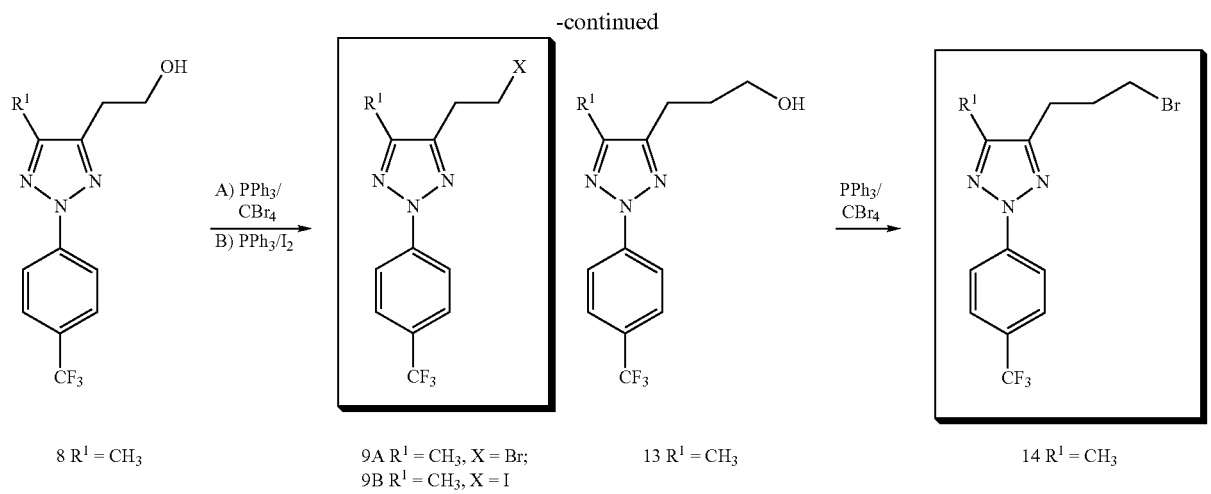

8 R¹ = CH₃

9A R¹ = CH₃, X = Br;
9B R¹ = CH₃, X = I

13 R¹ = CH₃

14 R¹ = CH₃

Alternatively in certain embodiments, compounds of formula 5 can be converted into intermediates 9A or 9B by successive treatment with potassium cyanide to form nitrile derivative 6, hydrochloric acid in ethanol to form ester derivative 7, lithium aluminum hydride to form hydroxylethyl derivative 8. Treatment with triphenyl phosphine and carbon tetrabromide forms intermediate 9A, while treatment with triphenyl phosphine and iodine forms intermediate 9B.

Alternatively in certain embodiments, compounds of formula 3 can be converted into intermediate 14 by successive treatment with diisobutyl aluminum hydride to form aldehyde derivative 10, carbethoxymethylene-triphenylphosphorane to form ester derivative 11, hydrogen and palladium on carbon to form ester derivative 12, lithium aluminum hydride to form hydroxylmethyl derivative 13, and triphenyl phosphine and carbon tetrabromide to form intermediate 14.

These latter routes are particularly useful form intermediates of formula i in Scheme 1 which have longer linking groups K. By using the methods outlined above, target compounds with linking groups of different lengths can be prepared as outlined in Schemes 4 and 5.

Scheme 4

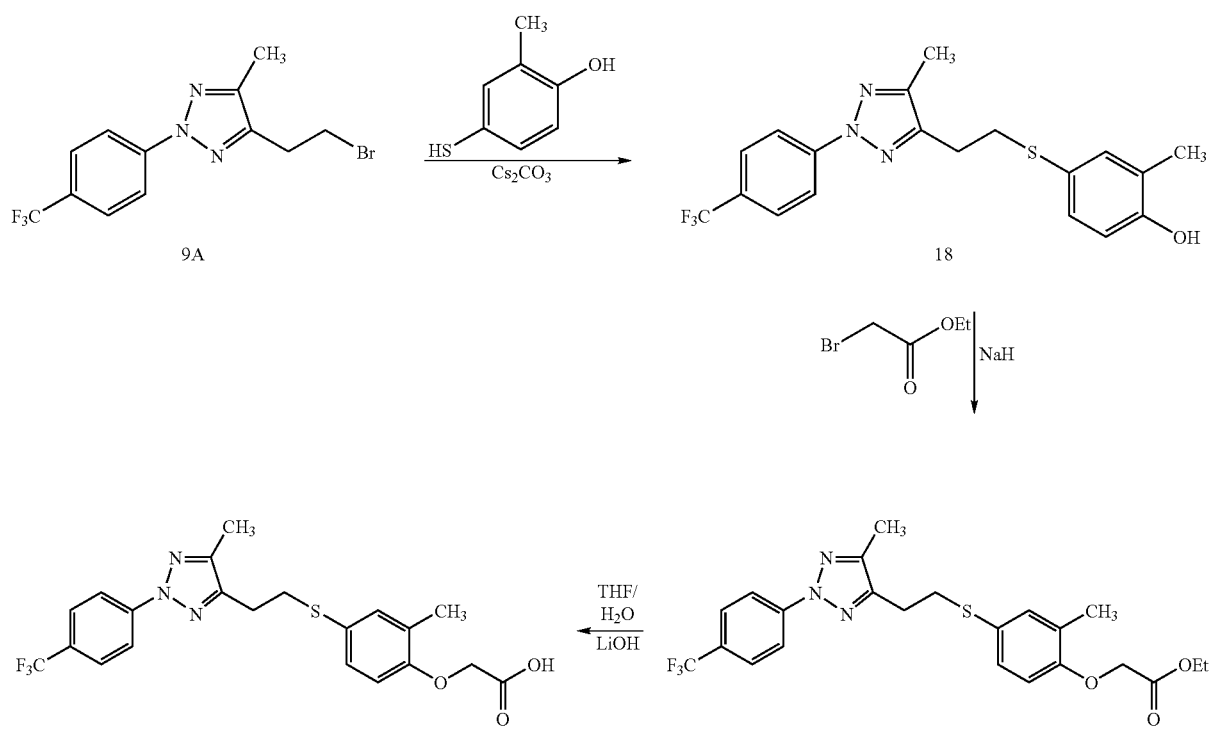

Thus in Scheme 4,2-bromoethyl-triazole 9A serves as the starting material. The acid chloride is treated with 4-mercaptophenol to provide substituted-triazole, 18. Treatment of 18 with the ethyl bromoacetate provides the target compound 19. Treatment of ester 19 with lithium hydroxide converts the ester to carboxylic acid compound 580.

Similarly in Scheme 5, compounds of formula I wherein $Y^1$ is $CH_2$, $Y^2$ is $CH_2CH_2$, and $Y^3$ is S can be prepared by treating 2-bromo propyl-triazole 14 with 4-mercaptophenol to provide substituted-triazole, 21. Treatment of 21 with the ethyl bromoacetate provides the target compound 22. Treatment of ester 22 with lithium hydroxide converts the ester to carboxylic acid compound 690.

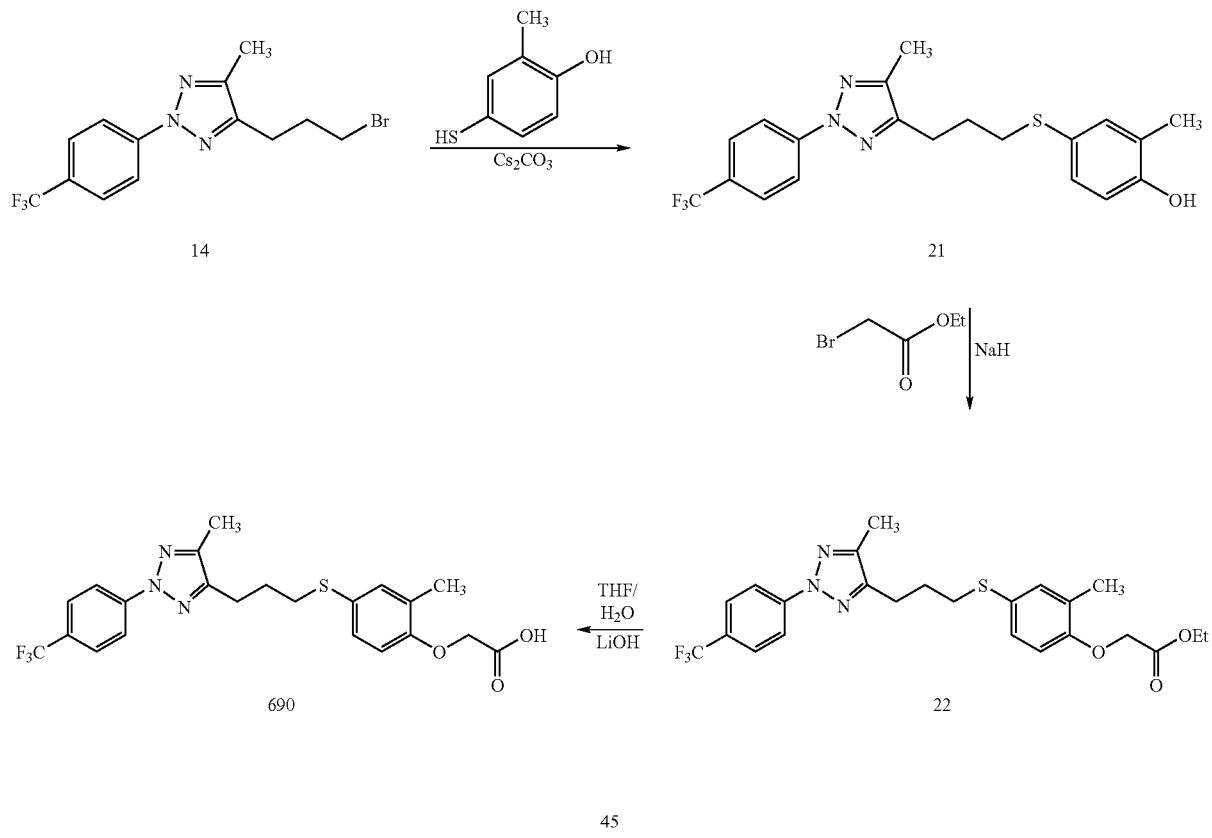

Scheme 5

Structural isomers, having the $Y^3$ attached at either the 2- or 3-position relative to the phenol hydroxyl group in compound 100 can be prepared from the corresponding 2-, or 3-mercaptophenols.

Still further, the general schemes outlined in Schemes 1-5 can be used to prepare compounds of Formula I in which $Ar^2$ is another ring system. To obtain these compounds, the phenols are replaced by the corresponding hydroxy-substituted ring system.

Likewise, the general schemes outlined in Schemes 1-5 can be used to prepare compounds of Formula I in which L or K is an alternatively functionalized linking group. To obtain these compounds, mercapto phenols may be replaced with halo phenols or halothiophenols and the resulting halogenated triazole intermediates can be coupled with propynoic esters to give unsaturated linking groups.

Scheme 6

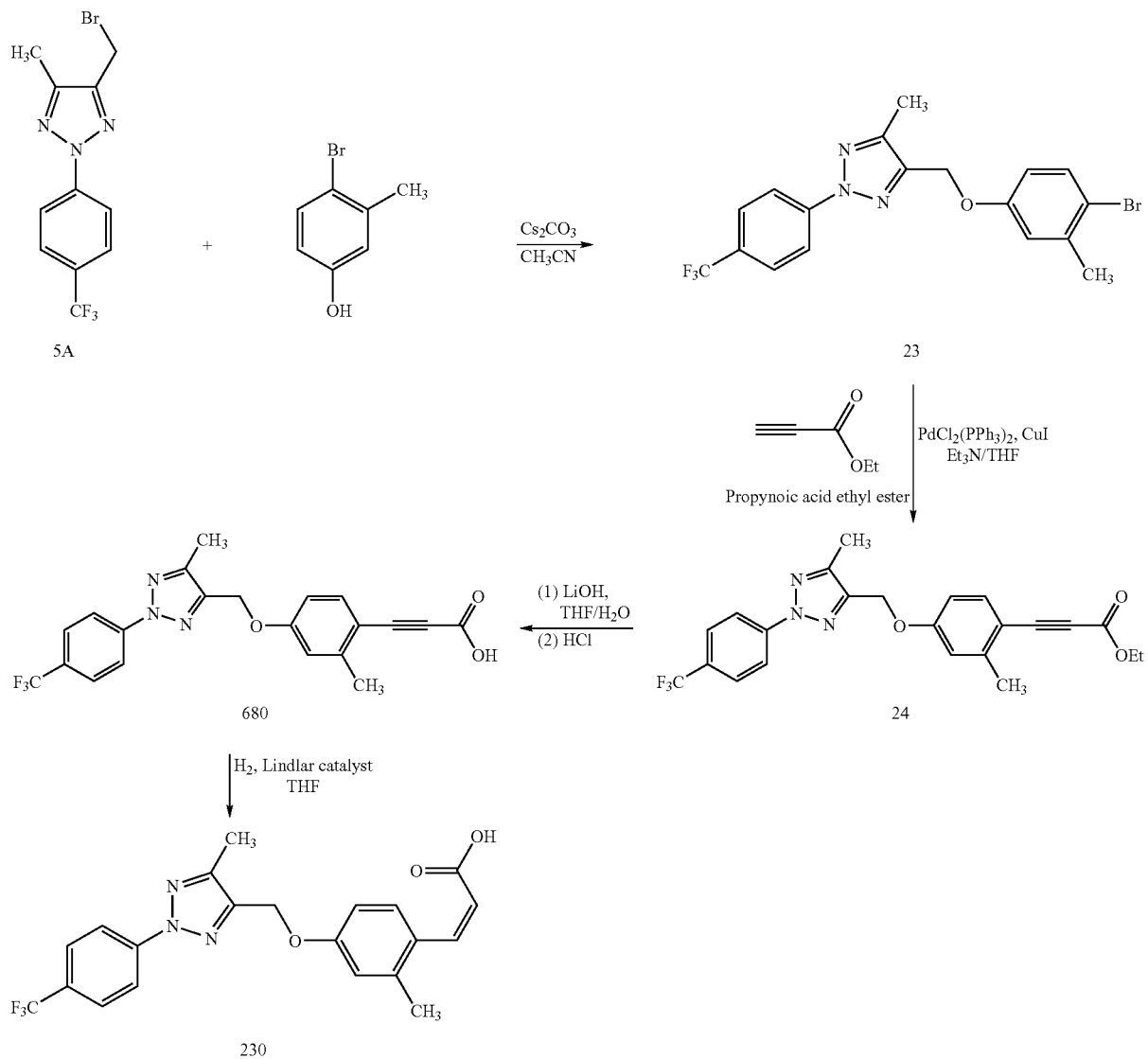

Thus in Scheme 6, aryl triazole 5A (prepared as described above) is condensed with 4-bromo phenol in the presence of cesium carbonate to provide compound 23. Treatment of 23 with propynoic acid ethyl ester in the presence of a Pd/C catalyst provides the target compound 24. Treatment of ester 24 with lithium hydroxide converts the ester to carboxylic acid compound 680. The acid compound can be hydrogenated to provide the Z-alkenoic acid triazole, 230.

Alternatively in certain embodiments, the an alkylene or E-alkenyl linker can be formed as is shown in Scheme 7. Aryl triazole 5A (prepared as described above) is condensed with 4-hydroxybenzaldehyde in the presence of cesium carbonate to provide compound 25A. Treatment of 25A with an appropriate Wittig reagent provides the target compound 26A. Treatment of ester 26A with lithium hydroxide converts the ester to the E-alkenoic acid triazole, 120. Similarly, Aryl triazole 26B can prepared by condensing with 4-benzaldehyde 25B with an appropriate Wittig reagent to provide the target compound 26B. Hydrogenation of ester 26B converts the alkenyl compounds to the alkylenyl triazoles.

Scheme 7

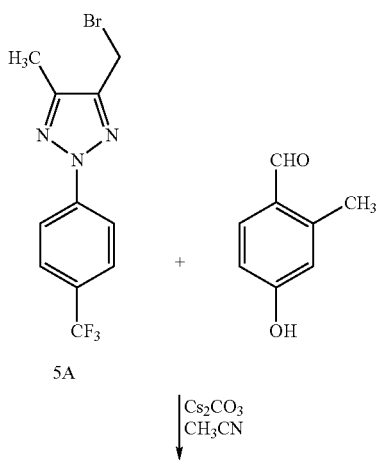

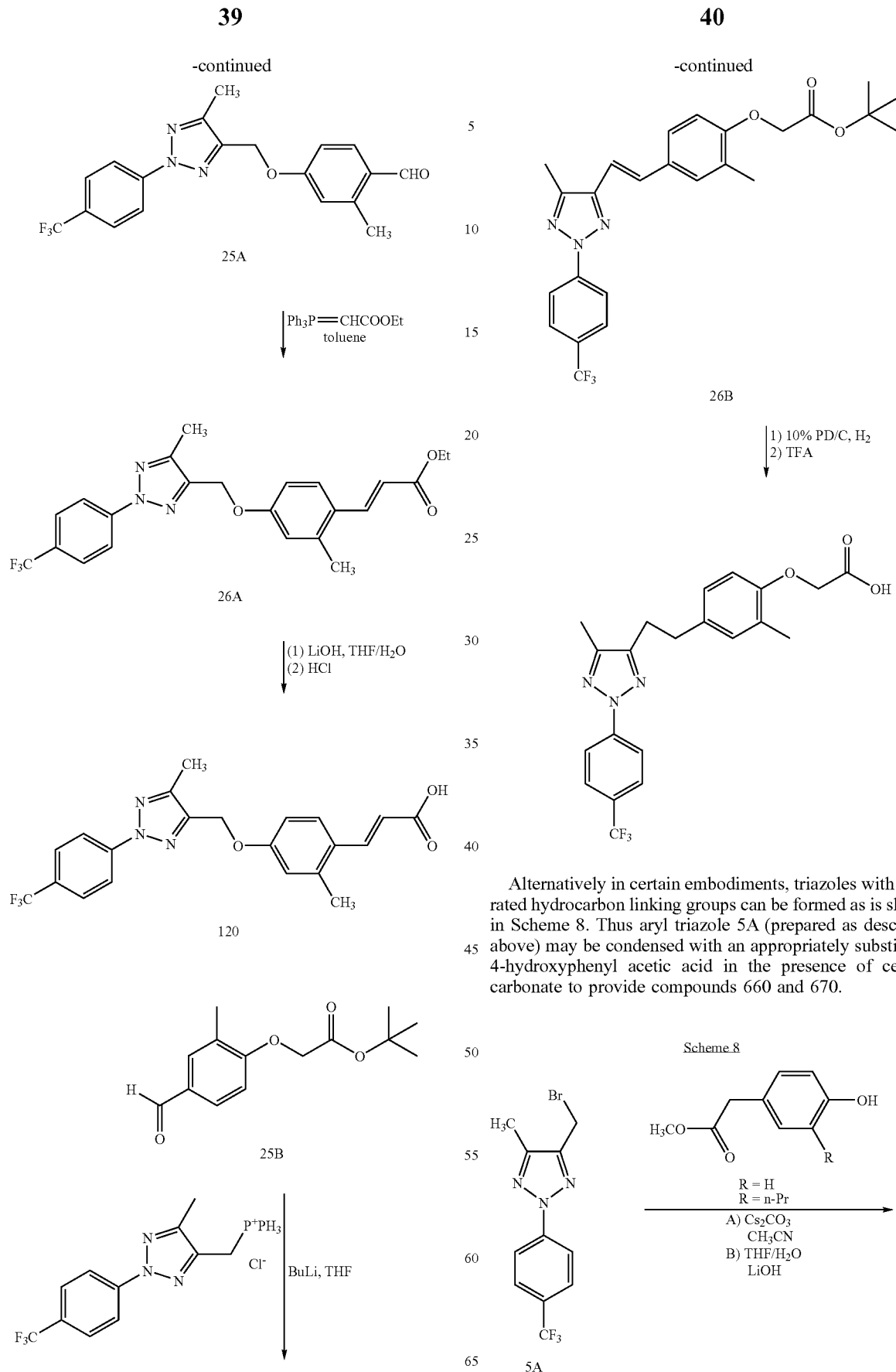
Alternatively in certain embodiments, triazoles with saturated hydrocarbon linking groups can be formed as is shown in Scheme 8. Thus aryl triazole 5A (prepared as described above) may be condensed with an appropriately substituted 4-hydroxyphenyl acetic acid in the presence of cesium carbonate to provide compounds 660 and 670.

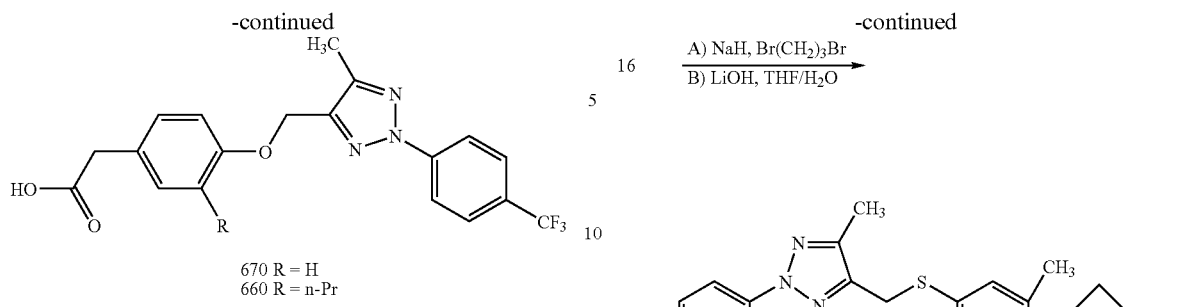

670 R = H
660 R = n-Pr

The carbon atoms on linkers L and K can also be differentially substituted as is shown in Scheme 9. Thus triazole ester 16 may be condensed with the appropriate alkyl halide in the presence of sodium hydride to provide compounds 210, 220, 510, 520, and 530.

Scheme 9

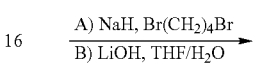

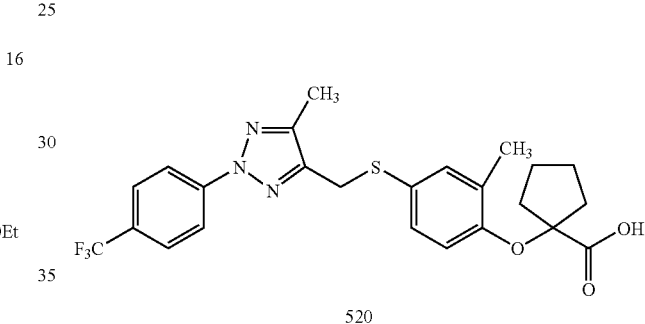

510

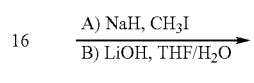

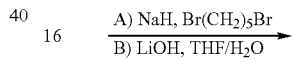

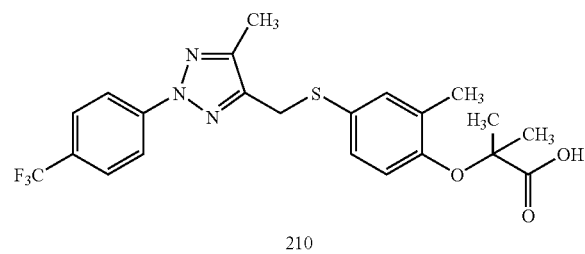

210

520

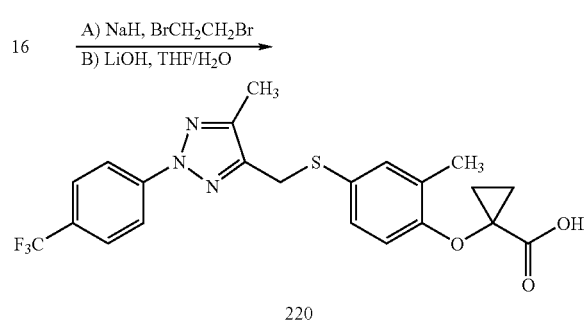

220

530

Likewise, $R^1$ can then be differentially substituted as is shown in Scheme 10. Thus triazole ester 3A may be modified as above with mercapto phenol and a halopropionate ester to provide hydroxy methyl triazole ester 29. Hydroxymethyl triazole can then be mesylated and condensed with the appropriate heterocyclic group, such as 4-methoxyphenyl piperazine to provide the target compound 31. Treatment of ester 31 with lithium hydroxide converts the ester to carboxylic acid compound 700.

Scheme 10

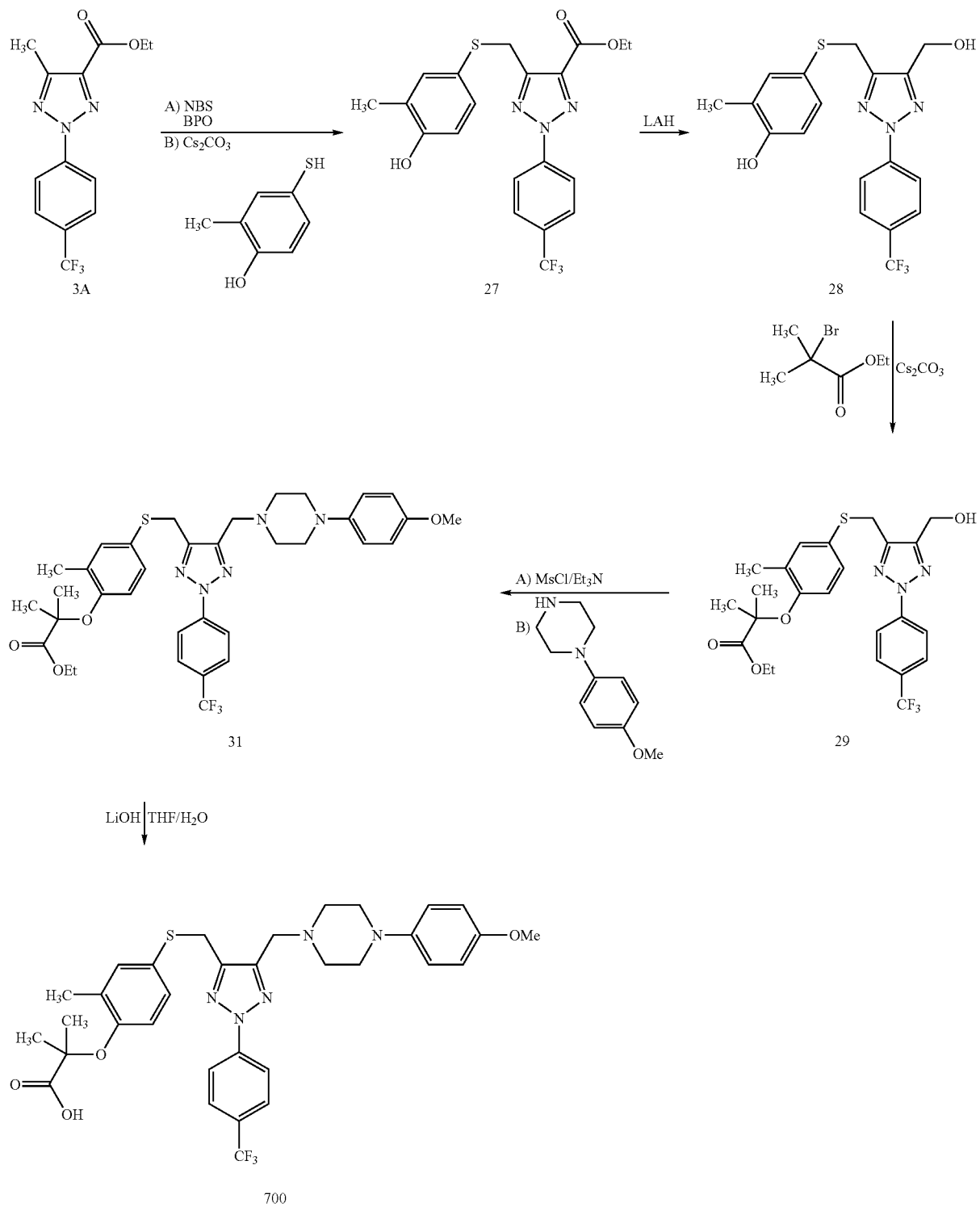

Likewise, related compounds with different Ar[1] and Ar[2] rings and different lengths and substitution of linkers L and K can be prepared in a similar manner beginning with appropriately substituted aryl compounds many of which are available from commercial sources or can be prepared according to literature methods. More specific details are provided in the examples below. In each of Schemes 1-10, reaction conditions (e.g., amounts of reactants, solvents, temperatures and workup conditions) can be selected using the Examples below as a guide.

Additionally, while the synthetic route is illustrated for the preparation of electrophilic triazole compounds, the invention is not so limited and synthetic routes are contemplated wherein the triazole intermediates used are nucleophilic (compounds 4, 8, and 13) and the $Ar^2$ containing intermediates are electrophilic.

Preparation of Alcohols, Ethers, Nitrites, Amides, and Aldehydes

The above general synthesis schemes are provided to illustrate the prepared of compounds of Formula I in which Z is a carboxylic acid or ester. Conversion of each of these groups into the corresponding alcohols, ethers, nitrites, amides, or aldehydes can be accomplished using methods generally known to one of skill in the art. Several methods for reduction (and oxidation) are provided below as illustrative of the processes used in preparing additional compounds of the invention.

Conversion of Carboxylic Acids into Alcohols, Ethers, Nitrites, Amides and Aldehydes.

The carboxylic acids of this invention can be converted into the corresponding alcohols, ethers, nitrites, amides and aldehydes by a number of methods, including the routes A-D shown in Scheme 11. The method to be used in a given case depends on the nature of R, and the substituents thereon. A variety of useful methods are described in Larock, COMPREHENSIVE ORGANIC TRANSFORMATIONS, VCH Publishers Inc, New York (1989). In particular, methods are described for converting acyl chlorides 32 to aldehydes 33 (p 620), esters 31 to aldehydes 33 (p 621), esters 31 to carbinols 35 (p 549), carboxylic acids 31 to carbinols 35 (p 548), esters 31 to amides 34 (p 987) and esters 31 to nitrites 36(p 988).

In method A, Scheme 11, a carboxylic acid 31 is first converted into the corresponding acid chloride 32. This transformation is effected by reacting the acid 31 with oxalyl chloride, phosphorus pentachloride, or, preferably, thionyl chloride. The reaction is conducted in an aprotic solvent such as dichloromethane, tetrahydrofuran or, preferably, 1,2-dichloroethane. The acid chloride 32 is then converted into the aldehyde 33 by chemical reduction, such as by the use of sodium borohydride in DMF at −70° C., as described in Tetrahedron Lett. 22:11 (1981), or, more preferably by hydrogenation using 5% palladium on barium sulfate as catalyst (see, for example, J. Amer. Chem. Soc., 108:2608 (1986). The reaction is conducted in an aprotic solvent such as toluene or, preferably, xylene. The aldehyde 33 is converted into the carbinol 35 by reduction, for example by reaction with 9 BBN, lithium aluminum tritertiarybutoxy hydride, or more preferably sodium borohydride, (see, J. Amer. Chem. Soc. 71:122 (1949)). The reaction is conducted in a protic solvent such as ethanol, or preferably, isopropanol.

Alternatively ester 31 can be converted directly into the aldehyde 3 by reduction, for example, by the use of sodium aluminum hydride or preferably, diisobutyl aluminum hydride (see e.g., Synthesis, 617 (1975)). The reaction is conducted in a non-polar solvent such as benzene or, preferably, toluene.

In method B, Scheme 11, ester 5 is converted into the amide 4 by transesterification with hydroxypyridine and the corresponding amine (see, J.C.S. C. 89 (1969)). The reaction is conducted in an ethereal solvent such as dioxane or, preferably, tetrahydrofuran.

In method C, Scheme 11, ester 5 is converted into the carbinol 4 by reduction with lithium aluminum hydride or, preferably, with lithium borohydride (see, J. Amer. Chem. Soc., 109:1186 (1987)). The reaction is conducted in an ethereal solvent such as dioxane or, preferably, tetrahydrofuran.

Alternatively, carboxylic acid 31 can be converted into the carbinol 35. This conversion is effected by reacting the carboxylic acid with a reducing agent such as lithium aluminum hydride or, preferably, with diborane, as described in ORGANIC SYNTHESES, 64:104 (1985). The reaction is conducted in an ethereal solvent such as dioxane or, preferably, tetrahydrofuran.

The carbinol 35 ($R^6$=H) can be converted into the ether 35 ($R^6$=$C_1$-$C_8$). This transformation is effected by an alkylation reaction, for example by reacting the carbinol 35 with an alkyl chloride ($C_1$-$C_8$)Cl. The reaction is conducted in an aprotic solvent such as dichloromethane or, preferably, tetrahydrofuran, in the presence of an organic base such as triethylamine or, preferably, pyridine.

In method D, Scheme 11, the ester 31 is converted into the nitrile 36. This conversion is effected by reacting the ester with a dehydrating agent such as dimethylaluminum nitride as described in Tett. Lett., 4907 (1979).

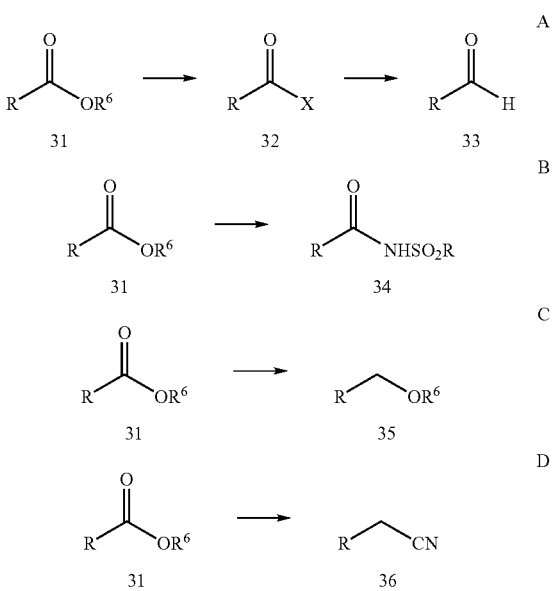

Furthermore, the tetrazole derivatives may be conveniently prepared by a general process wherein a compound like 36 is coupled to an alcohol using the Mitsunobu protocol (Synthesis 1, (1981).

Not all compounds of formula 1 may be compatible with some of the reaction conditions described in the Examples. Such restrictions are readily apparent to those skilled in the art of organic synthesis, and alternative methods must then be used.

Isomeric Compounds

Certain of the compounds of the present invention possess one or more chiral centers and each center may exist in the R or S configuration. The present invention includes all diastereomeric, enantiomeric and epimeric forms as well as the appropriate mixtures thereof. For many compounds of the present invention, a single chiral center is present (at the carbon atom bearing $R^2$), resulting in racemic mixtures of enantiomers. As noted above, the present invention further includes compounds, compositions and methods wherein a single isomer (or single enantiomer) is provided or used. Methods of preparing chiral compounds are provided in Examples. Alternatively, mixtures of enantiomers can be separated into their individual isomers via methods known in the art such as salt formation and crystallization with chiral bases, chiral chromatography (e.g., HPLC using commercially available columns for chiral resolution) and via methods such as simulated moving bed chromatography (see, for example, U.S. Pat. No. 5,518,625).

In certain preferred embodiments of the invention, the (−)-isomer of the compound of formula I is used, which is substantially free of its (+)-isomer. In this context, "substantially free" refers to a compound that is contaminated by less than about 20%, more preferably 10%, still more preferably 5%, even more preferably 2% and most preferably less than about 1% of the undesired isomer. In other preferred embodiments of the invention, the (+)-isomer of the compound of formula I is used, which is substantially free of its (−)-isomer.

Additionally, the compounds of the present invention may exist as geometric isomers. The present invention includes all cis, trans, syn, anti, entgegen (E), and zusammen (Z) isomers as well as the appropriate mixtures thereof.

In some situations, compounds may exist as tautomers. All tautomers are included within formula I and are provided by this invention.

Solvate Forms of the Compounds of the Invention

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Prodrug Forms of the Compounds of the Invention

In some embodiments, the compounds of the invention are present in a prodrug form. In particular, the invention also provides, for example, compounds of Formula I in which $CO_2H$ is esterified to form $-CO_2R^6$, wherein $R^6$ is a member selected from the group consisting of H, $(C_1-C_8)$alkyl, halo$(C_1-C_8)$alkyl, $-X^4OR^2$, $-X^4NR^2R^3$, $(C_2-C_8)$alkenyl, $(C_3-C_7)$cycloalkyl, heterocyclyl, aryl$(C_1-C_4)$alkyl and aryl$(C_2-C_8)$alkenyl.

$R^2$ and $R^3$ are members independently selected from the group consisting of H, $(C_1-C_8)$alkyl, halo$(C_1-C_8)$alkyl, $-X^3OR^9$, aryl, aryl$(C_1-C_4)$alkyl, heteroaryl, or optionally, if both present on the same substituent, may be joined together to form a three- to eight-membered ring system. Each $X^3$ and $X^4$ are members independently selected from the group consisting of $(C_1-C_4)$alkylene, $(C_2-C_4)$alkenylene, and $(C_2-C_4)$alkynylene.

Esters of the compounds of the present invention may be prepared as described herein or according to conventional methods.

Pharmaceutical Compositions and Methods of Treating Diseases and Conditions

In accordance with the present invention, a therapeutically effective amount of a compound of Formula I can be used for the preparation of a pharmaceutical composition useful for treating diabetes, treating hyperlipidemia, treating hyperuricemia, treating obesity, lowering triglyceride levels, lowering cholesterol levels, raising the plasma level of high density lipoprotein, and for treating, preventing or reducing the risk of developing atherosclerosis.

The compositions of the invention can include compounds of Formula I, pharmaceutically acceptable salts thereof, or a hydrolysable precursor thereof. In general, the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of Type 2 diabetes.

The compounds of Formula I that are used in the methods of the present invention can be incorporated into a variety of formulations for therapeutic administration. More particularly, the compounds of Formula I can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a local rather than systemic manner, in a depot or sustained release formulation. In addition, the compounds can be administered in a liposome.

The compounds of Formula I can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. Compounds of Formula I can be administered alone, in combination with each other, or they can be used in combination with other known compounds (see *Combination Therapy* below).

Suitable formulations for use in the present invention are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds of Formula I can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide (DMSO) also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al. 1975 In: *The Pharmacological Basis of Therapeutics*, Ch. 1).

The amount of active compound that can be combined with a carrier material to produce a single dosage form will vary depending upon the disease treated, the mammalian species, and the particular mode of administration. However, as a general guide, suitable unit doses for the compounds of the present invention can, for example, preferably contain between 100 mg to about 3000 mg of the active compound. A preferred unit dose is between 500 mg to about 1500 mg. A more preferred unit dose is between 500 to about 1000 mg. Such unit doses can be administered more than once a day, for example 2, 3, 4, 5 or 6 times a day, but preferably 1 or 2 times per day, so that the total daily dosage for a 70 kg adult is in the range of 0.1 to about 250 mg per kg weight of subject per administration. A preferred dosage is 5 to about 250 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

A typical dosage can be one 10 to about 1500 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to interrupt, adjust, or terminate therapy in conjunction with individual patient response.

Combination Therapy

As noted above, the compounds of the present invention will, in some instances, be used in combination with other therapeutic agents to bring about a desired effect. Selection of additional agents will, in large part, depend on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R. *J. Clin. Endocrinol. Metab.* (1999) 84: 1165-71; United Kingdom Prospective Diabetes Study Group: UKPDS 28, *Diabetes Care* (1998) 21: 87-92; Bardin, C. W., (ed.), CURRENT THERAPY IN ENDOCRINOLOGY AND METABOLISM, 6th Edition (Mosby—Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al., *Diabet. Med.* (1996) 13 365-370; Kwiterovich, P. Am. *J. Cardiol* (1998) 82(12A): 3U-17U). These studies indicate that diabetes and hyperlipidemia modulation can be further improved by the addition of a second agent to the therapeutic regimen. Combination therapy includes administration of a single pharmaceutical dosage formulation which contains a compound having the general structure of Formula I and one or more additional active agents, as well as administration of a compound of Formula I and each active agent in its own separate pharmaceutical dosage formulation. For example, a compound of Formula I and an HMG-CoA reductase inhibitor can be administered to the human subject together in a single oral dosage composition, such as a tablet or capsule, or each agent can be administered in separate oral dosage formulations. Where separate dosage formulations are used, a compound of Formula I and one or more additional active agents can be administered at essentially the same time (i.e., concurrently), or at separately staggered times (i.e., sequentially). Combination therapy is understood to include all these regimens.

An example of combination therapy that modulates (prevents the onset of the symptoms or complications associated) atherosclerosis, wherein a compound of Formula I is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the compounds of Formula I can be administered in combination with more than one additional active agent, for example, a combination of a compound of Formula I with an HMG-CoA reductase inhibitor (e.g., lovastatin, simvastatin and pravastatin) and aspirin, or a compound of Formula I with an HMG-CoA reductase inhibitor and a β blocker.

Another example of combination therapy can be seen in treating obesity or obesity-related disorders, wherein the compounds of Formula I can be effectively used in combination with, for example, phenylpropanolamine, phenteramine, diethylpropion, mazindol; fenfluramine, dexfenfluramine, phentiramine, β-3 adrenoceptor agonist agents; sibutramine, gastrointestinal lipase inhibitors (such as orlistat), and leptins. Other agents used in treating obesity or obesity-related disorders wherein the compounds of Formula I can be effectively used in combination with, for example, neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Still another example of combination therapy can be seen in modulating diabetes (or treating diabetes and its related symptoms, complications, and disorders), wherein the compounds of Formula I can be effectively used in combination with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose), pramlintide (a synthetic analog of the human hormone amylin), other insulin secretogues (such as repaglinide, gliquidone, and nateglinide), insulin, as well as the active agents discussed above for treating atherosclerosis.

A further example of combination therapy can be seen in modulating hyperlipidemia (treating hyperlipidemia and its related complications), wherein the compounds of Formula I can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E, or vitamin C.

Additionally, an effective amount of a compound of Formula I and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozil; vitamin $B_6$ and the pharmaceutically acceptable salts thereof; vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, α-3 adrenergic receptor agonists; sulfonylureas, biguanides, α-glucosidase inhibitors, other insulin secretogogues, and insulin can be used together for the preparation of a pharmaceutical composition useful for the above-described treatments.

Kits

In addition, the present invention provides for kits with unit doses of the compounds of Formula I, either in oral or injectable doses. In addition to the containers containing the unit doses will be an informational package insert describing the use and attendant benefits of the drugs in alleviating symptoms and/or complications associated with Type 2 diabetes as well as in alleviating hyperlipidemia and hyperuricemia, or for alleviating conditions dependent on PPAR. Preferred compounds and unit doses are those described herein above.

For the compositions, methods and kits provided above, one of skill in the art will understand that preferred compounds for use in each are those compounds that are preferred above and particularly those compounds provided in formula I in FIGS. 1A-1D. Still further preferred compounds for the compositions, methods and kits are those compounds provided in the Examples below.

EXAMPLES

Experimental Section

General Methods

Intermediates

Synthesis of Intermediate Compound 3A

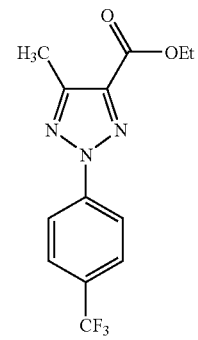

A solution of 4-trifluoromethyl-aniline hydrogen chloride in AcOH, $H_2O$, and concentrated HCl was cooled ≦5° C. and $NaNO_2$ (1.2 eq) in $H_2O$ was added slowly to the mixture. The resultant mixture was slowly added to a mixture of ethyl acetoacetate (1 eq) and in EtOH and NaOAc in 1N $Na_2CO_3$ at 0° C. The resulting mixture was stirred for 2 hrs and diluted with $H_2O$, and then extracted with EtOAc. The organic phases were combined and washed with $H_2O$, brine, dried over $Na_2SO_4$, and evaporated to give a crude product, which was used in the next reaction without purification.

To the crude product of the above reaction in ethanol was added $CuCl_2.2H_2O$ (2.2 eq.) and $NH_4OAc$ (10 eq). The reaction mixture was refluxed for 12 hrs and then cooled to room temperature. The reaction mixture was poured into a mixture of ice and concentrated HCl. The reaction mixture was then filtered and washed with 2N HCl. The resulting solid was purified by recrystallization from ethanol to afford desired product. $^1$H NMR (400 MHz, $CDCl_3$) δ 8.25 (2H, m), 7.76 (2H, m), 4.48 (2H, q, J=7.2), 2.63 (3H, s), 1.46(3H, t, J=7.2).

Synthesis of Intermediate Compound 3B

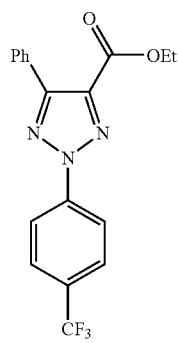

A solution of 4-trifluoromethyl-aniline hydrogen chloride in AcOH, H$_2$O, and concentrated HCl was cooled ≦5° C. and NaNO$_2$ (1.2 eq) in H$_2$O was added slowly to the mixture. The resultant mixture was slowly added to a mixture of 3-oxo-3-phenyl-propionic acid ethyl ester (1 eq) and in EtOH and NaOAc in 1N Na$_2$CO$_3$ at 0° C. The resulting mixture was stirred for 2 hrs and diluted with H$_2$O, and then extracted with EtOAc. The organic phases were combined and washed with H$_2$O, brine, dried over Na$_2$SO$_4$, and evaporated to give a crude product, which was used in the next reaction without purification.

To the crude product of the above reaction in ethanol was added CuCl$_2$2H$_2$O (2.2 eq) and NH$_4$OAc (10 eq). The reaction mixture was refluxed for 12 hrs and then cooled to room temperature. The reaction mixture was poured into a mixture of ice and concentrated HCl. The reaction mixture was then filtered and washed with 2N HCl. The resulting solid was purified by recrystallization from ethanol to afford desired product 3B.

Synthesis of Intermediate Compound 4A

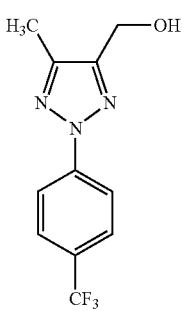

To a solution of compound 3A (3.5 g, 11.7 mmol) in anhydrous THF (50 mL) was added LiAlH$_4$ (0.89 g, 23.4 mmol) at 0° C. The reaction mixture was kept at 0° C. for 2 hrs and then quenched with 10% NaOH. The reaction mixture was filtered and washed with EtOAc. The filtrate was concentrated to give 2.6 g of compound 4A. $^1$H NMR (400 MHz, CDCl$_3$) δ 8.12 (2H, d, J=8.0), 7.71 (2H, d, J=8.0), 4.82 (2H, s), 2.43 (3H, s).

Synthesis of Intermediate Compound 4B

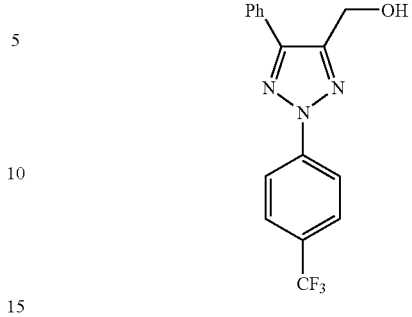

To compound 3B in anhydrous THF (50 mL) was added LiAlH$_4$ (2 eq) at 0° C. The mixture was kept at 0° C. for 2 hrs and quenched with 10% NaOH, filtered, washed with EtOAc, and concentrated to give compound 4B.

Synthesis of Intermediate Compound 5A

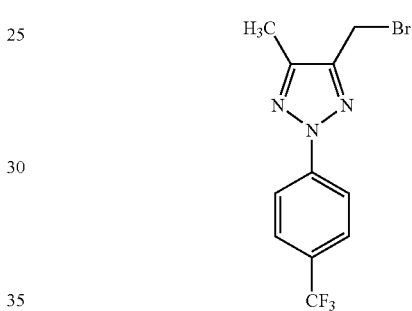

A mixture of compound 4A (1.6 g,), 48% HBr (10 mL) and AcOH (10 mL) was heated at 100° C. for 2 hrs. The reaction mixture was then cooled to room temperature, filtered, washed with water, and air dried to give 1.1 g of compound 5A. $^1$H NMR (400 MHz, CDCl$_3$) δ 8.14~8.11 (2H, m), 7.74~7.7 (2H, m), 4.57 (2H, s), 2.43(3H, s).

Synthesis of Intermediate Compound 5B

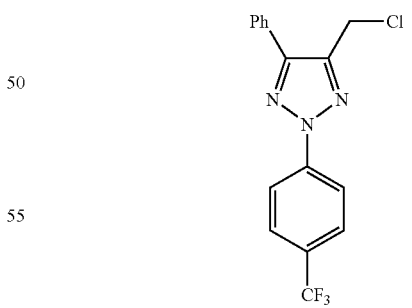

To a solution of compound 4B in CH$_2$Cl$_2$ was added SOCl$_2$ (3 eq) at room temperature. The mixture was refluxed for 5 hrs, the mixture was cooled to room temperature and evaporated, the residue was purified by chromatography to afford desired product. $^1$H NMR (400 MHz, CDCl$_3$) δ 8.22 (2H, d, J=8.8 Hz), 7.9~7.87(2H, m), 7.74(2H, d, J=8.8 Hz), 7.52~7.4(3H, m), 4.98 (2H, s).

Synthesis of Intermediate Compound 5C

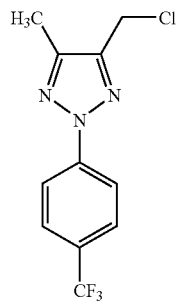

To a solution of compound 4A in CH$_2$Cl$_2$ was added SOCl$_2$ (3 eq) at room temperature. The mixture was refluxed for 5 hrs, the mixture was cooled to room temperature and evaporated, the residue was purified by chromatography to afford desired product. $^1$H NMR (400 MHz, CDCl$_3$) δ 8.12 (2H, d, J=8.4 Hz), 7.72 (2H, d, J=8.4 Hz), 4.72 (2H, s), 2.46 (3H, s).

The following compounds were made according to the procedure above:

Compound 5D

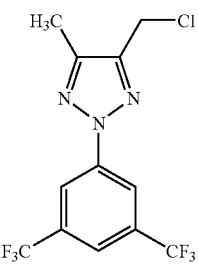

$^1$H NMR (400 MHz, CDCl$_3$) δ 8.49 (2H, s), 7.81 (1H, s), 4.72 (2H, s), 2.47 (3H, s).

Compound 5E

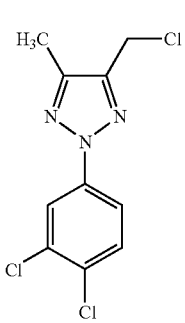

$^1$H NMR (400 MHz, CDCl$_3$) δ 8.15 (1H, d, J=2.8 Hz), 7.86 (1H, dd, J=8.8, 2.4 Hz), 7.52 (1H, d, J=8.4 Hz), 4.7 (2H, s), 2.44 (3H, s).

Compound 5F

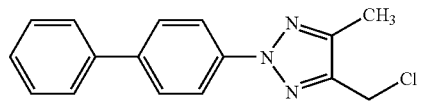

$^1$H NMR (400 MHz, CDCl$_3$) δ 8.09~8.04 (2H, m), 7.7~7.67(2H, m), 7.64~7.61(2H, m), 7.49~7.43(2H, m), 7.39~7.35(1H, m), 4.74 (2H, s), 2.46(3H, s).

Compound 5G

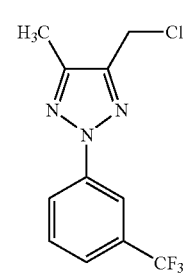

$^1$H NMR (400 MHz, CDCl$_3$) δ 8.30 (1H, s), 8.21 (1H, m), 7.59 (2H, m), 4.72 (2H, s), 2.46 (3H, s).

Compound 5H

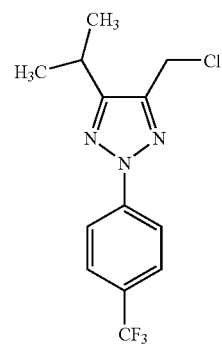

$^1$H NMR (400 MHz, CDCl$_3$) δ 8.15 (2H, m), 7.72 (2H, m), 4.74 (2H, s), 3.20 (1H m), 1.40 (6H, d, J=7.2 Hz).

Compound 5I

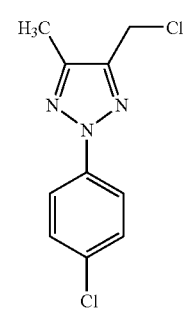

$^1$H NMR (400 MHz, CDCl$_3$) δ 7.93 (2H, m), 7.42 (2H, m), 4.79 (2H, s), 2.41 (3H, s).

Compound 5J

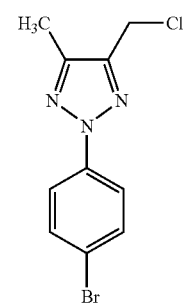

$^1$H NMR (400 MHz, CDCl$_3$) δ 7.84 (2H, d, J=9.2 Hz), 7.50 (2H, d, J=9.2 Hz), 4.79 (2H, s), 2.41 (3H, s).

Synthesis of Intermediate Compound 6

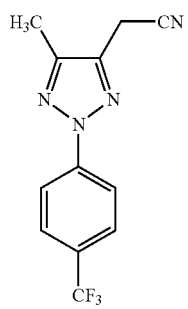

The mixture of compound 5A and KCN (2 eq) in ethanol was refluxed for 6 hours. The volatiles were evaporated and the residue was partitioned between EtOAc and water. The organic layer was washed with brine, dried over $Na_2SO_4$, concentrated, and purified by flash chromatography to give desired product 6. $^1$H NMR (400 MHz, $CDCl_3$) δ 8.13~8.1 (2H, m), 7.74~7.71 (2H,m), 3.85 (2H, s), 2.44(3H, s).

Synthesis of Intermediate Compound 7A

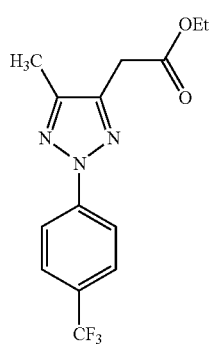

To a saturated ethanolic solution of HCl was added compound 6 and the mixture was refluxed for 3 hrs. The solvent was evaporated and the residue was partitioned between EtOAc and a pH 7 buffer solution. The organic phase was separated, washed with brine, dried over $Na_2SO_4$, and evaporated. The residue was purified by chromatography on silica gel to give the desired ester 7A.

Synthesis of Intermediate Compound 7B

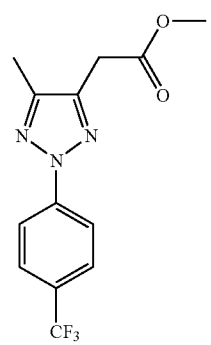

To a saturated methanolic solution of HCl was added compound 6 and the mixture was refluxed for 3 hrs. The solvent was evaporated and the residue was partitioned between EtOAc and a pH 7 buffer solution. The organic phase was separated, washed with brine, dried over $Na_2SO_4$, and evaporated. The residue was purified by chromatography on silica gel to give the desired ester 7B. $^1$H NMR (400 MHz, $CDCl_3$) δ 8.1~8.08(2H, m), 7.69~7.766 (2H,m), 3.78 (2H, s), 3.73(3H,s), 2.35(3H, s).

Synthesis of Intermediate Compound 8

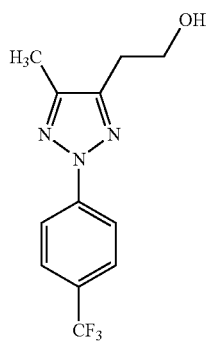

To a solution of compound 7A or B in anhydrous THF was added $LiAlH_4$ (2 eq.) at 0° C. The mixture was kept at 0° C. for 2 hrs and then quenched with 10% NaOH. The reaction mixture was then filtered and washed with EtOAc. The filtrate was concentrated to give compound 8. $^1$H NMR (400 MHz, $CDCl_3$) δ 7.98(2H, d, J=8.4 Hz), 7.59 (2H, d, J=8.4 Hz), 3.89 (2H, t, J=6 Hz), 3.83(2H, t, J=6 Hz), 3.0~2.6(1H, br), 2.25(3H, s).

Synthesis of Compound 9A

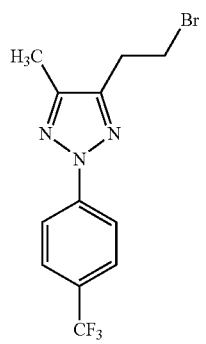

To a solution of compound 8 and $CBr_4$ was added $PPh_3$ at room temperature. The reaction mixture was stirred at room temperature for 5 hrs. The volatiles were evaporated and the resulting residue was purified by chromatography on silica gel to give compound 9A.

Synthesis of Compound 9B

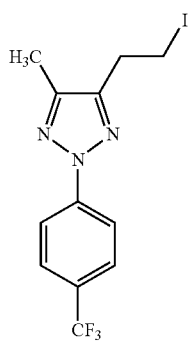

To a solution of compound 8 (0.19 mg, 0.7 mmol), imidazole (95 mg, 1.4 mmol), and PPh$_3$ (367 mg, 1.4 mmol) in CH$_2$Cl$_2$, was added I$_2$ (215 mg, 1.4 mmol) at 0° C. The mixture was stirred overnight at room temperature, diluted with EtOAc, and washed with aqueous Na$_2$S$_2$O$_3$, brine, dried over Na$_2$SO$_4$, and evaporated. The residue was purified by chromatography on silica gel to give 0.22 g compound 9B. $^1$H NMR (400 MHz, CDCl$_3$) δ 8.03(2H, dd, J=9.2, 0.8 Hz), 7.63 (2H, dd, J=9.2, 0.8 Hz), 3.41~3.37 (2H, m), 3.24~3.2(2H, m), 2.3(3H, s).

Synthesis of Intermediate Compound 10A

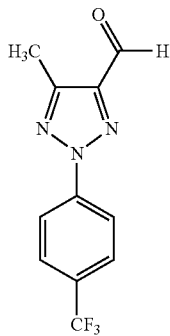

To a solution of compound 3A in anhydrous CH$_2$Cl$_2$ was added DIBAL (1.1 eq) at −78° C. under N$_2$. The mixture was stirred at −78° C. for 4 hrs. The reaction mixture was quenched with saturated NH$_4$Cl and then filtered through a plug of Celite. The filtrate was partitioned between EtOAc and water. The organic phase was washed with brine, dried over NaSO$_4$, evaporated, and the residue was purified by chromatography on silica gel to give compound 10A.

Synthesis of Intermediate Compound 10B

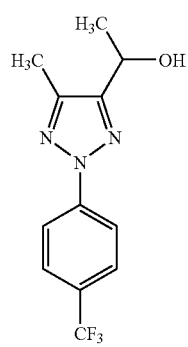

To a solution of compound 10A in anhydrous THF was added MeMgBr (2 eq) at 0° C. under N$_2$ and The mixture was allowed to warm to room temperature. The reaction mixture was quenched with saturated NH$_4$Cl and diluted with EtOAc. The organic phase was washed with brine, dried over NaSO$_4$, evaporated, and the residue was purified by chromatography on silica gel to give compound 10B. $^1$H NMR (400 MHz, CDCl$_3$) δ 8.12(2H, 8.4 Hz), 7.71 (2H, d, J=9.2 Hz), 5.14~5.08(1H, m), 2.45(3H, s), 2.09(1H, d, J=6 Hz), 1.64(3H, d, J=6.8 Hz).

Synthesis of Intermediate Compound 10C

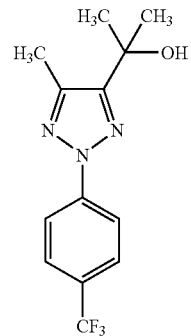

To a solution of compound 3A in anhydrous THF was added MeMgBr (4 eq) at 0° C. under N$_2$ and The mixture was allowed to warm to room temperature. The reaction mixture was quenched with saturated NH$_4$Cl and diluted with EtOAc. The organic phase was washed with brine, dried over NaSO$_4$, evaporated, and the residue was purified by chromatography on silica gel to give compound 10C. $^1$H NMR (400 MHz, CDCl$_3$) δ 8.11(2H, 8.8 Hz), 7.7(2H, d, J=8.8 Hz), 2.51(3H, s), 2.29 91H, br), 1.68(6H, s).

Synthesis of Intermediate Compound 11

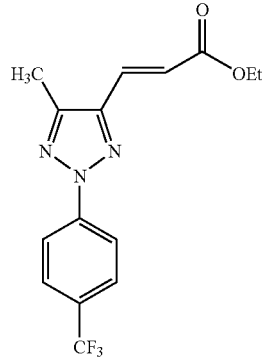

A mixture of aldehyde 10A and (carbethoxymethylene)-triphenylphosphorane (1.1 eq) in toluene was stirred at 100° C. for 3 hrs. The solvent was evaporated and the residue was purified by chromatography on silica gel to give compound 11.

Synthesis of Intermediate Compound 12

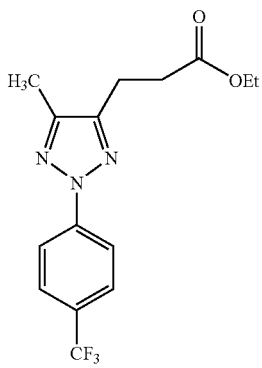

A solution of 11 in MeOH was stirred with Pd/C 10% under $H_2$ at room temperature overnight. The reaction was filtered through a plug of Celite. The filtrate was concentrated under reduced pressure to give the desired compound 12.

Synthesis of Intermediate Compound 13

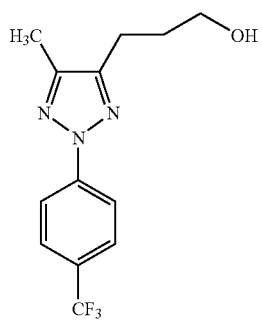

To a solution of compound 12 in anhydrous THF was added $LiAlH_4$ (2 eq) at 0° C. The reaction mixture was kept at 0° C. for 2 hrs and then quenched with 10% NaOH. The reaction mixture was then filtered and washed with EtOAc. The filtrate was concentrated to give compound 13.

Synthesis of Intermediate Compound 14

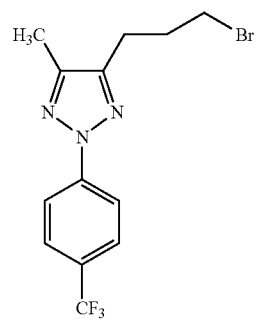

To a mixture of compound 13 and $CBr_4$ was added $PPh_3$ at room temperature. The mixture was stirred at room temperature for 5 hrs. The volatiles were evaporated and the residue was purified by chromatography on silica gel to give compound 14.

Synthesis of Intermediate Compound 27

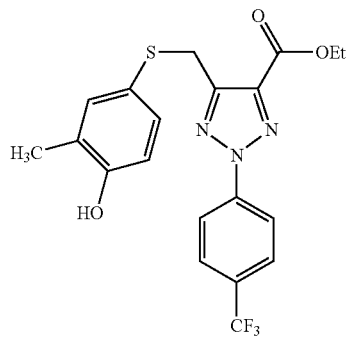

To a solution of 3A (2.83 g, 10 mmol) in carbon tetrachloride (100 mL) was added N-bromo succinimide (2.14 g, 12 mmol) and benzoyl peroxide (0.24 g, 1 mmol) at room temperature and the mixture was refluxed for 5 hours. After cooling to 0° C., the mixture was filtered through Celite and the solvent was evaporated to yield crude product. The crude product was dissolved in MeCN (30 mL) and 4-mercapto-2-methylphenol (1.38 g, 10 mmol) and cesium carbonate (3.26 g, 10 mmol) was added to the solution. The mixture was allowed to stir at room temperature for 3 hours. The mixture was filtered through Celite and washed with EtOAc, evaporated and the residue was purified by chromatography to give 2.1 g of a white solid.

Synthesis of Intermediate Compound 28

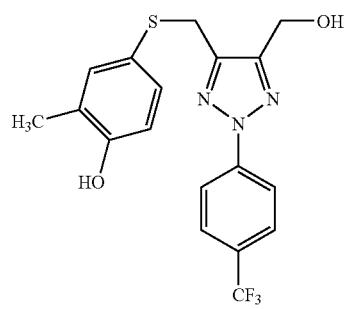

To a solution of compound 27 (2.1 g, 5 mmol) in anhydrous THF (100 mL) was added $LiAlH_4$ (0.38 g, 10 mmol) at 0° C. The mixture was kept at 0° C. for 2 hrs and the reaction was quenched with EtOH. The solvent was evaporated and the residue was diluted with EtOAc, washed with 2N HCl, brine, and dried over $Na_2SO_4$. The solvent was evaporated to yield 1.6 g of a white solid.

Synthesis of Intermediate Compound 29A

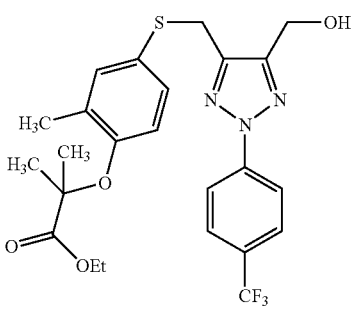

To a solution of compound 28 (0.75 g, 1 mmol) in toluene (10 mL) was added cesium carbonate (1.3 g, 4 mmol) and 2-bromo-2-methyl-propionic acid ethyl ester (0.8 g, 4 mmol) and the mixture was heated to 97° C. for 4 hours. The mixture was cooled to room temperature, filtered through Celite, and washed with EtOAc. The solvent was evaporated and the residue was purified by chromatography to yield 0.45 g of the desired product. $^1$H NMR (400 MHz, CDCl$_3$) δ 8.07(2H, d, J=8.8 Hz), 7.7(2H, d, J=8.8 Hz), 7.2~7.18(1H, m), 7.06~7.03(1H, m), 6.52(1H, d, J=8.4 Hz), 4.74(2H, d, J=6.4 Hz), 4.19(2H, q, J=7.2 Hz), 4.17(2H, s), 2.19(1H, t, J=6.4 Hz), 2.15(3H, s), 1.55(6H, s), 1.2(3H, t, J=7.2 Hz.)

The following compounds were made according to the procedure above:

Compound 29B

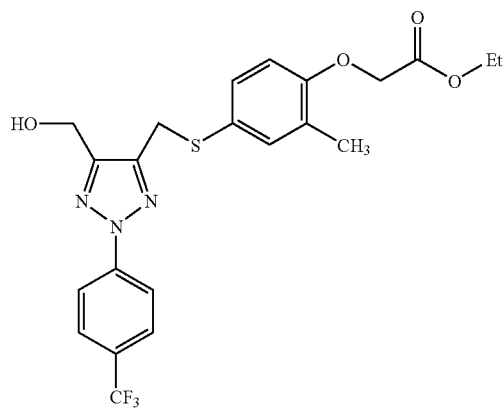

$^1$H NMR (400 MHz, CDCl$_3$) 8.07(2H, d, J=8.4 Hz), 7.71(2H, d, J=8.8 Hz), 7.21(1H, s), 7.14(1H, d, J=8.4 Hz), 6.58(1H, d, J=8.4 Hz), 4.74(2H, s), 4.6(2H, s), 4.23(2H, q, J=6.8 Hz), 4.17(2H, s), 2.22(3H, s), 1.27(3H, t, J=6.8 Hz).

Compound 29C

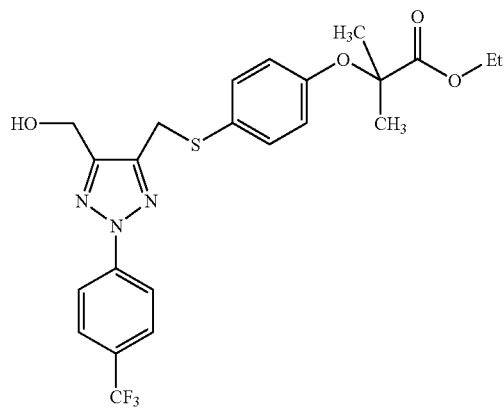

$^1$H NMR (400 MHz, CDCl$_3$) δ 8.06(2H, d, J=8.8 Hz), 7.7(2H, d, J=8.8 Hz), 7.26~7.24(2H, m), 6.75~6.71(2H, m), 4.74(2H, d, J=6.4 Hz), 4.182(2H, q, J=7.2 Hz), 4.18(2H, s), 4.15(1H, t, J=6.4 Hz), 1.55(6H,s), 1.2(3H, t, J=7.2 Hz).

Example 1A

{2-Methyl-4-[5-methyl-2-(4-trifluoromethyl-phenyl)-2H-[1,2,3]triazol-4-ylmethylsulfanyl]-phenoxy}-acetic acid (Compound 100)

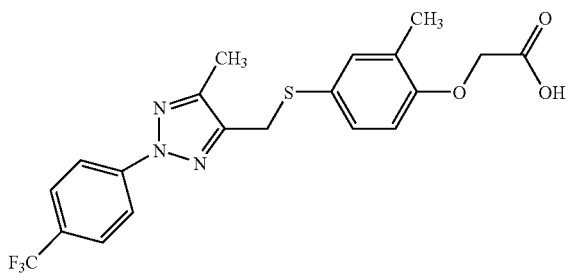

To a mixture of compound 5A (500 mg, 1.56 mmol) and 4-mercapto-2-methyl-phenol (237 mg, 1.72 mmol) in MeCN (15 mL) was added Cs$_2$CO$_3$ (560 mg, 1.72 mmol). The mixture was stirred at room temperature for 4 hrs. TLC showed disappearance of compound 5A. Ethyl bromoacetate (0.2 mL, 2 mmol) was added followed by addition of Cs$_2$CO$_3$ (717 mg, 2.2 mmol). The mixture was stirred for another 4 hours. The mixture was then filtered through Celite and washed with ethyl acetate. The solvent was evaporated and the residue was purified by flash chromatography on silica gel to give 610 mg of the desired ester.

To a solution of the ester in THF (5 mL) was added aqueous LiOH (4 mL, 4 mmol). The mixture was stirred at room temperature for 1 hr, acidified with 1N HCl, and then extracted with EtOAc. The organic phase was washed with brine, dried, and concentrated. The residue was recrystallized from hexanes and ethyl acetate to give 360 mg white solid. 1H NMR (400 MHz, DMSO) δ 13.0 (1H, br), 8.03 (2H, d, J=8.8 Hz), 7.87(2H, d, J=8.8 Hz), 7.2~7.14 (2H, m), 6.76 (1H, d, J=8.4 Hz), 4.67 (2H, s), 4.2 (2H, s), 2.22 (3H, s), 2.1 (3H, s).

Example 1B

2-{2-Methyl-4-[5-methyl-2-(4-trifluoromethyl-phenyl)-2H-[1,2,3]triazol-4-ylmethylsulfanyl]-phenoxy}-propionic acid (Compound 110)

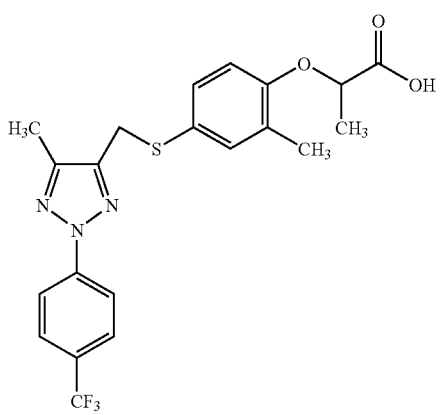

The following compound was made according to the procedure of Example 1A using compound 5A. $^1$H NMR (400 MHz, CDCl$_3$) δ 8.03 (2H, d, J=8 Hz), 7.68 (2H, J=8Hz), 7.2 (1H, d, J=1.6 Hz), 7.15 (1H, dd, J=8.8, 2 Hz), 6.61 (1H, d, J=8.4 Hz), 4.74 (1H, q, J=7.2 Hz), 4.07 (2H, s), 2.24(3H, s), 2.2 (3H, s), 1.65(3H, d, J=7.2 Hz).

Example 1C

{4-[2-(3,5-Bis-trifluoromethyl-phenyl)-5-methyl-2H-[1,2,3]triazol-4-ylmethylsulfanyl]-2-methyl-phenoxy}-acetic acid (Compound 630)

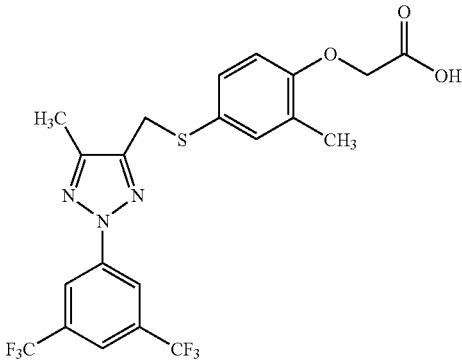

The following compound was made according to the procedure of Example 1A using compound 5D. $^1$H NMR (400 MHz, CDCl$_3$) δ 8.39 (2H, s), 7.76 (1H, s), 7.24 (1H, d, J=2 Hz), 7.17 (1H, dd, J=8.4, 2 Hz), 6.63 (1H, d, J=8.4 Hz), 4.66 (1H, s), 4.08 (2H, s), 2.24(3H, s), 2.27 (3H, s), 2.23 (3H, s).

Example 1D

{4-[2-(3,4-Dichloro-phenyl)-5-methyl-2H-[1,2,3]triazol-4-ylmethylsulfanyl]-2-methyl-phenoxy}-acetic acid (Compound 640)

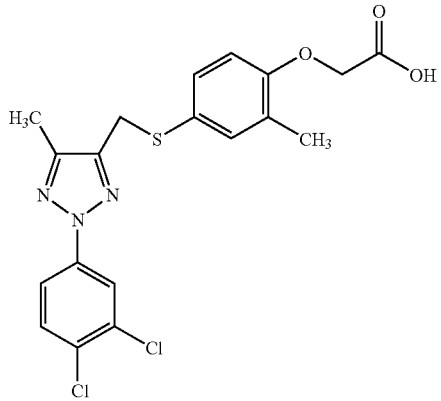

The following compound was made according to the procedure of Example 1A using compound 5E. $^1$H NMR (400 MHz, CDCl$_3$) δ 8.05 (1H, d, J=2.4 Hz), 7.77 (1H, dd, J=8.8, 2.4 Hz), 7.48 (1H, d, J=8.4 Hz), 7.21 (d, J=2 Hz), 7.17 (1H, dd, J=8.4, 2.4 Hz), 6.63 (1H, d, J=8.4 Hz), 4.67 (2H, s), 4.05 (2H, s), 2.24(3H, s), 2.23 (3H, s).

Example 1E

[4-(2-Biphenyl-4-yl-5-methyl-2H-[1,2,3]triazol-4-ylmethylsulfanyl)-2-methyl-phenoxy]-acetic acid

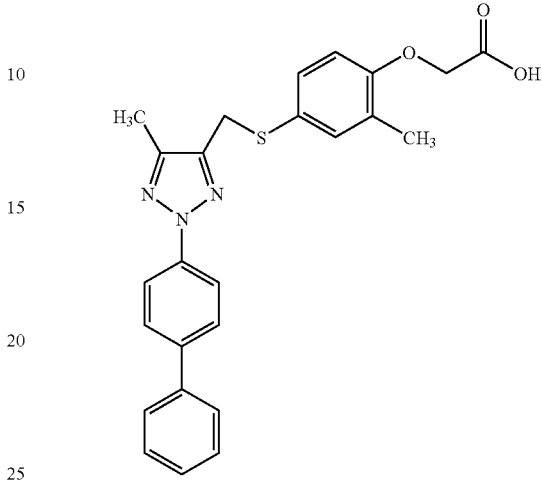

The following compound was made according to the procedure of Example 1A using compound 5F. $^1$H NMR (400 MHz, CDCl$_3$) δ 7.98 (2H, d, J=9.2 Hz), 7.66 (2H, d, J=9.2 Hz), 7.63~7.6 (3H, m), 7.45 (2H, t, J=7.2 Hz), 7.36 (1H, t, J=7.2 Hz), 7.23 (1H, d, J=1,6 Hz), 7.18 (1H, dd, J=8.4, 2 Hz), 6.63 (1H, d, J=8.8 Hz), 4.65 (2H, s), 4.09 (2H, s), 2.25 (3H, s), 2.23 (3H, s).

Example 1F

2-Methyl-2-{2-methyl-4-[5-methyl-2-(4-trifluoromethyl-phenyl)-2H-[1,2,3]triazol-4-ylmethylsulfanyl]-phenoxy}-propionic acid (Compound 210)

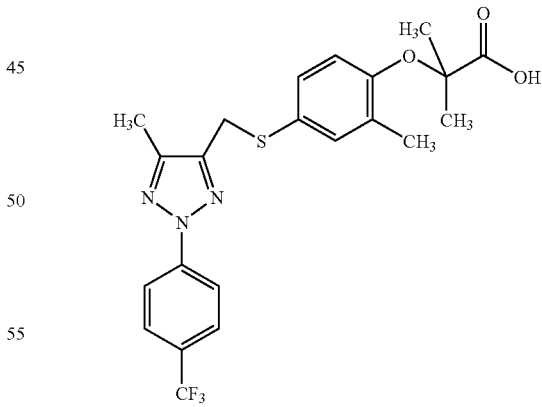

To a mixture of compound 5C (1.1 g, 4 mmol) and 4-mercapto-2-methyl-phenol (1.07 g, 4.4 mmol) in MeCN (15 mL) was added CsCO3 (1.96 g, 6 mmol), the mixture was stirred at room temperature for 4 hrs. TLC showed disappearance of compound 5C. The mixture was filtrated through celite and washed with ethyl acetate, the solvent was evaporated and the residue was purified by flash chromatography on silica gel to give 1.2 g desired product.

To a solution of above compound (0.36 g, 1 mmol) in toluene (10 mL) was added CsCO₃ (0.65 g, 2 mmol) and ethyl α-bromoisobutyrate (0.39 g, 2 mmol), the mixture was stirred at 90° C. for 4 hrs. The mixture was filtrated through celite and washed with ethyl acetate, the solvent was evaporated and the residue was purified by flash chromatography on silica gel to give 0.42 g desired ester.

To a solution of the ester (0.34 g, in THF (5 mL) was added aqueous LiOH (4 mL, 4 mmol), the mixture was stirred at room temperature for 1 hr, acidified with 1N HCl, extracted with EtOAc. The organic phase was washed with brine, dried and concentrated, the residue was recrystallized from hexanes and ethyl acetate to give 360 mg white solid. ¹H NMR (400 MHz, CDCl₃) δ 8.05~8.02 (2H, m), 7.7~7.67 (2H, m), 7.21 (1H, d, J=2.4 Hz), 7.14~7.11 (1H, m), 6.71 (1H, d, J=8.8 Hz), 4.1 (2H, s), 2.27 (3H, s), 2.18 (3H, s), 1.59 (6H, s).

Example 1G (2-Methyl-4-{1-methyl-1-[5-methyl-2-(4-trifluoromethyl-phenyl)-2H-[1,2,3]triazol-4-yl]-ethylsulfanyl}-phenoxy)-acetic acid

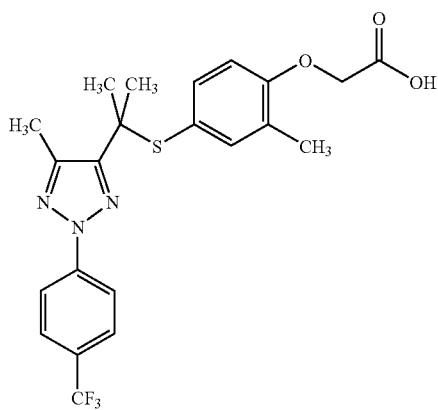

To a solution of 10C (1.15 g, 4 mmol) in CH₂Cl₂ (10 mL) was added ZnI₂ (1.28 g, 4 mmol) and solution (4-Mercapto-2-methyl-phenoxy)-acetic acid (1.08 g, 4.8 mmol) in CH₂Cl₂ (5 mL), the mixture was stirred at room temperature for 20 hrs. The reaction was quenched with small amount water, the solvent was evaporated and the residue was purified by flash chromatography on silica gel to give 0.4 g desired ester.

To a solution of the ester (0.34 g, 0.69 mmol), in THF (3 mL) was added aqueous LiOH (1.4 mL, 1.4 mmol), the mixture was stirred at room temperature for 1 hr, acidified with 1N HCl, extracted with EtOAc. The organic phase was washed with brine, dried and concentrated, the residue was recrystallized from hexanes and ethyl acetate to give 0.18 g white solid. ¹H NMR (400 MHz, CDCl₃) δ 7.98~7.96 (2H, m), 7.66~7.64 (2H, m), 6.94~6.93(1H, m), 6.9~6.87 (1H, m), 6.46 (1H, d, J=8.8 Hz), 5.13(2H, s), 4.54 (2H, s), 2.55 (3H, s) 1.72 (6H, s).

Example 1H

{4-[5-Isopropyl-2-(4-trifluoromethyl-phenyl)-2H-[1,2,3]triazol-4-ylmethylsulfanyl]-2-methyl-phenoxy}-acetic acid

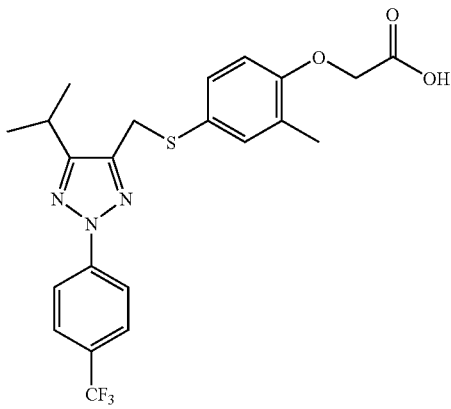

The title compound was prepared from intermediate compound 5H, 4-mercapto-2-methyl-phenol and ethyl bromoacetate using the procedure described above. ¹H NMR (400 MHz, DMSO-d₆) δ 13.02 (1H, br), 8.02 (2H, d, J=8.8 Hz), 7.87 (2H, d, J=8.8 Hz), 7.17 (2H, m), 6.76 (1H, d, J=8.8Hz), 4.66 (2H, s), 4.22 (2H, s), 3.09 (1H, m), 2.10 (3H, s), 1.25 (6H, d, J=7.2 Hz).

Example 1I

{4-[2-(4-Chloro-phenyl)-5-methyl-2H-[1,2,3]triazol-4-ylmethylsulfanyl]-2-methyl-phenoxy}-acetic acid

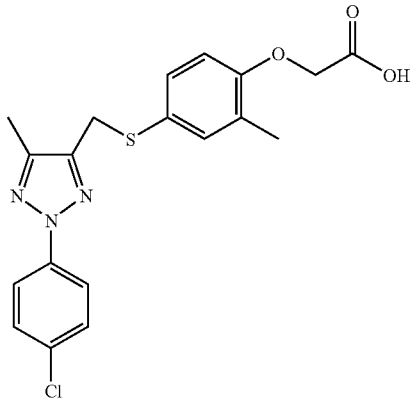

The title compound was prepared from intermediate compound 5I, 4-mercapto-2-methyl-phenol and ethyl bromoacetate using the procedure described above. ¹H NMR (400 MHz, DMSO-d₆) δ 13.00 (1H, br), 7.83 (2H, dd, J=7.2, 2.4 Hz), 7.55 (2H, dd, J=7.2, 2.4 Hz), 7.14 (2H, m), 6.75(1H, d, J=8.4 Hz), 4.66 (2H, s), 4.17 (2H, s), 2.19 (3H, s), 2.10 (3H, s).

Example 1J

{4-[2-(4-Bromo-phenyl)-5-methyl-2H-[1,2,3]triazol-4-ylmethylsulfanyl]-2-methyl-phenoxy}-acetic acid

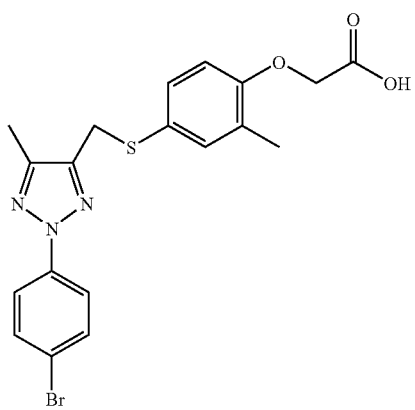

The title compound was prepared from intermediate compound 5J, 4-mercapto-2-methyl-phenol and ethyl bromoacetate using the procedure described above. $^1$H NMR (400 MHz, DMSO-d$_6$) δ 13.00 (1H, br), 7.77 (2H, dd, J=6.8, 2.4 Hz), 7.68 (2H, dd, J=7.2, 2.4 Hz), 7.15 (2H, m), 6.75(1H, d, J=8.4 Hz), 4.66 (2H, s), 4.17 (2H, s), 2.19 (3H, s), 2.10 (3H, s).

Example 1K

{2-Methyl-4-[5-methyl-2-(3-trifluoromethyl-phenyl)-2H-[1,2,3]triazol-4-ylmethysulfanyl]-phenoxy}-acetic acid

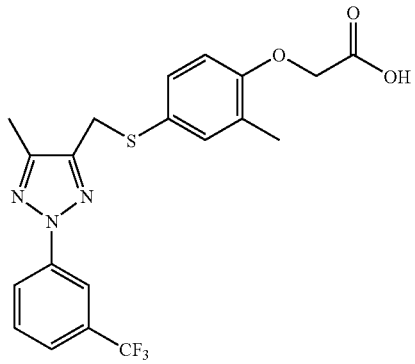

The title compound was prepared from intermediate compound 5G, 4-mercapto-2-methyl-phenol and ethyl bromoacetate using the procedure described above. $^1$H NMR (400 MHz, DMSO) δ 12.98 (1H, br), 8.12 (1H, m), 8.05 (1H, s), 7.73 (2H, m), 7.19 (1H, m), 7.14 (1H, d J=8.8 Hz), 4.65 (2H, s), 4.20 (2H, s), 2.21 (3H, s), 2.10 (3H, s).

Example 1L

2-{4-[2-(4-Chloro-phenyl)-5-methyl-2H-[1,2,3]triazol-4-yl-methylsulfanyl]-2-methyl-phenoxy}-propionic acid

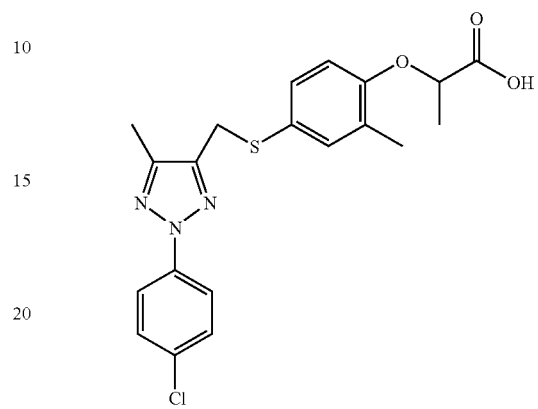

The title compound was prepared from intermediate compound 5I, 4-mercapto-2-methyl-phenol and ethyl 2-bromopropionate using the procedure described above. $^1$H NMR (400 MHz, DMSO-d$_6$) δ 7.83 (2H, m), 7.55 (2H, m), 7.15 (2H, m), 6.69 (1H, d, J=8.8 Hz), 4.77 (1H, q, J=6.4Hz), 4.17 (2H, s), 2.18 (3H, s), 2.09 (3H, s), 1.47 (3H, d, J=6.4 Hz).

Example 1M

{2-Chloro-4-[5-methyl-2-(4-trifluoromethyl-phenyl)-2H-[1,2,3]triazol-4-ylmethylsulfanyl]-phenoxy}-acetic acid

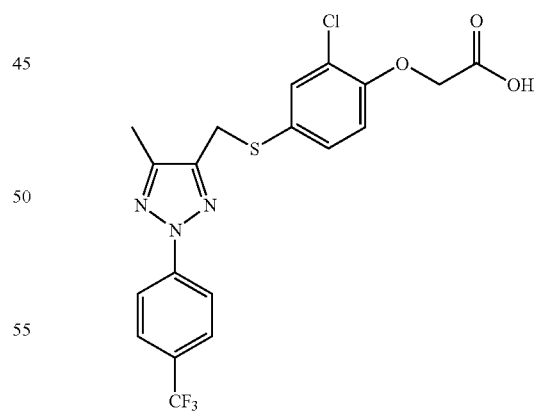

The title compound was prepared from intermediate compound 5A, 4-mercapto-2-chloro-phenol and ethyl 2-bromoacetate using the procedure described above. $^1$H NMR (400 MHz, DMSO-d$_6$) δ 13.12 (1H, br), 8.02 (2H, d, J=8.8 Hz), 7.86 (2H, d, J=8.8 Hz), 7.48(1H, d, J=2.4 Hz), 7.28 (1H, dd, J=8.4, 2.4 Hz), 6.96 (1H, d, J=8.4 Hz), 4.78 (2H, s), 4.29 (2H, s), 2.26 (3H, s).

Example 1N (2-Methyl-4-{1-[5-methyl-2-(4-trifluoromethyl-phenyl)-2H-[1,2,3]triazol-4-yl]-ethylsulfanyl}-phenoxy)-acetic acid

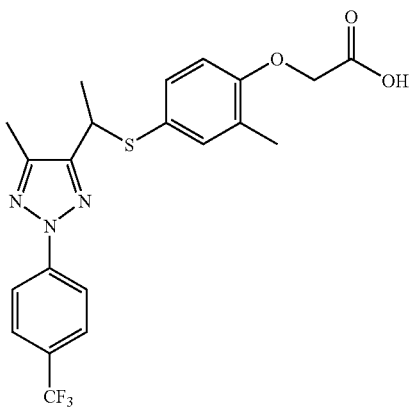

The title compound was prepared from intermediate compound 11, (4-Mercapto-2-methyl-phenoxy)-acetic acid using the procedure described above. $^1$H NMR (400 MHz, CDCl$_3$) δ 8.05(2H, d, J=8.4 Hz), 7.68(2H, d, J=8.4 Hz), 7.17~7.12(2H,m), 6.61 (1H, d,J=8 Hz), 4.64 (2H, s), 4.33 (1H, q, J=6.8 Hz), 2.31(3H,s), 2.2(3H, s), 1.71 (3H, d, J=6.8 Hz).

Example 2

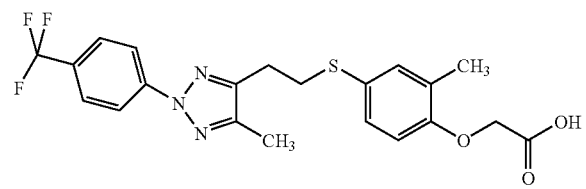

(2-Methyl-4-{2-[5-methyl-2-(4-trifluoromethyl-phenyl)-2H-[1,2,3]triazol-4-yl]-ethylsulfanyl}-phenoxy)-acetic acid (Compound 580)

To a mixture of compound 9B (114 mg, 0.3 mmol) and 4-mercapto-2-methyl-phenol (50 mg, 0.36 mmol) in MeCN (5 mL) was added Cs$_2$CO$_3$ (98 mg, 0.3 mmol). The mixture was stirred at room temperature for 4 hrs. TLC showed disappearance of compound 9B. Ethyl bromoacetate (67 mg, 0.4 mmol) was added followed by addition of Cs$_2$CO$_3$ (130 mg, 0.4 mmol). The mixture was stirred for another 4 hours. The mixture was then filtered through Celite and washed with ethyl acetate. The volatiles were evaporated and the residue was purified by flash chromatography on silica gel to give 85 mg of the desired ester.

To a solution of the ester (80 mg) in THF (3 mL) was added aqueous LiOH (1 mL, 1 mmol). The mixture was stirred at room temperature for 1 hr, acidified with 1N HCl, and extracted with EtOAc. The organic phase was washed with brine, dried and concentrated. The residue was recrystallized from hexanes and ethyl acetate to give 50 mg of a white solid. $^1$H NMR (400 MHz, CDCl$_3$) δ 13.0 (1H, br), 8.06 (2H, d, J=8.8 Hz), 7.68(2H, d, J=8.8 Hz), 7.2~7.14 (2H, m), 6.63 (1H, d, J=8.4 Hz), 4.63 (2H, s), 3.22~3.18 (2H, m), 2.98~2.93(2H, m), 2.29 (3H, s), 2.23 (3H, s).

Example 3

{2-Methyl-4-[5-phenyl-2-(4-trifluoromethyl-phenyl)-2H-[1,2,3]triazol-4-ylmethylsulfanyl]-phenoxy}-acetic acid, (Compound 340)

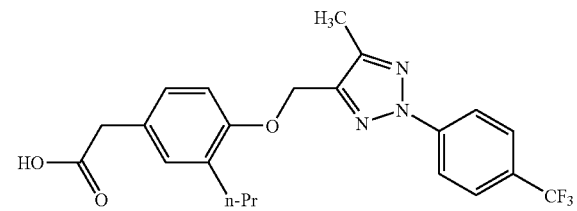

To a mixture of compound 5B (1 eq) and 4-mercapto-2-methyl-phenol (1.2 eq mmol) in MeCN (15 mL) was added Cs$_2$CO$_3$ (1.2 eq). The mixture was stirred at room temperature for 4 hrs. TLC showed disappearance of compound 5B. Ethyl bromoacetate (1.5 eq) was added followed by addition of Cs$_2$CO$_3$ (1.5 eq) and the mixture was stirred for another 4 hours. The mixture was filtered through Celite and washed with ethyl acetate. The solvent was evaporated and the residue was purified by flash chromatography on silica gel to give desired ester.

To a solution of the ester in THF was added aqueous LiOH (3 eq). The mixture was stirred at room temperature for 1 hr, acidified with 1N HCl, and extracted with EtOAc. The organic phase was washed with brine, dried and concentrated, The residue was recrystallized from hexanes and ethyl acetate to give the desired acid. $^1$H NMR (400 MHz, CDCl$_3$) δ 8.15 (2H, d, J=8.8 Hz), 7.81~7.78 (2H, m), 7.73 (2H, d, J=8.8 Hz), 7.5~7.4 (3H, m), 7.3~7.2(2H,m), 6.61 (1H, d, J=8.8 Hz), 4.65 (2H, s), 4.29 (2H, s), 2.21 (3H, s).

Example 4

{3-Propyl-4-[5-methyl-2-(4-trifluoromethyl-phenyl)-2H-[1,2,3]triazol-4-ylmethoxy]-phenyl}-acetic acid (Compound 660)

To a mixture of (4-hydroxy-3-propyl-phenyl)-acetic acid methyl ester (125 mg, 0.6 mmol) and compound 5A (192 mg, 0.6 mmol) in MeCN (5 mL) was added Cs$_2$CO$_3$ (234 mg, 0.72 mmol). The mixture was stirred at room temperature for 4 hrs. The mixture was filtered through Celite and washed with ethyl acetate. The solvent was evaporated and the residue was purified by flash chromatography on silica gel to give 150 mg of the desired ester.

To a solution of the ester in THF (2 mL) was added aqueous LiOH (1.8 mL, 1.8 mmol), the mixture was stirred at room temperature for 1 hr, acidified with 1N HCl, extracted with EtOAc. The organic phase was washed with brine, dried and concentrated. The residue was recrystallized from hexanes and ethyl acetate to give 58 mg of a white solid. $^1$H NMR (400 MHz, CDCl$_3$) δ 8.14 (2H, d, J=8.8 Hz), 7.72 (2H, d, J=8.8 Hz), 7.07~7.12 (2H,m), 6.97 (1H, d, J=8.4 Hz), 5.19 (2H, s), 3.58 (2H, s), 2.57 (2H, t, J=7.6 Hz), 2.45 (3H, s), 1.52~1.64 (2H, m), 0.92 (3H, t, J=7.2 Hz).

Example 5

{4-[2-(4-trifluoromethyl-phenyl)-2H-[1,2,3]triazol-4-yl-methoxy]-phenyl}-acetic acid (Compound 670)

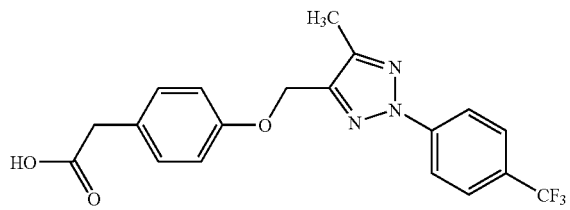

To a mixture of (4-hydroxy-phenyl)-acetic acid methyl ester (125 mg, 0.6 mmol) and compound 5A (192 mg, 0.6 mmol) in MeCN (5 mL) was added Cs$_2$CO$_3$ (234 mg, 0.72 mmol). The mixture was stirred at room temperature for 4 hrs. The mixture was filtered through Celite and washed with ethyl acetate. The solvent was evaporated and the residue was purified by flash chromatography on silica gel to give 150 mg desired ester.

To a solution of the ester in THF (2 mL) was added aqueous LiOH (1.8 mL, 1.8 mmol), the mixture was stirred at room temperature for 1 hr, acidified with 1N HCl, extracted with EtOAc. The organic phase was washed with brine, dried and concentrated. The residue was recrystallized from hexanes and ethyl acetate to give 48 mg of white solid. $^1$H NMR (400 MHz, DMSO) 612.2 (1H, br), 8.15 (2H, d, J=8.4 Hz), 7.91 (2H, d, J=8.4 Hz), 7.16~7.22 (2H, m), 6.98~7.02 (2H, m), 5.24 (2H, s), 3.48 (2H, s), 2.39 (3H, s).

Example 6A

2-Methyl-2-{2-methyl-4-[5-methyl-2-(4-trifluoromethyl-phenyl)-2H-[1,2,3]triazol-4-ylmethoxy]-phenoxy}-propionic acid (Compound 290)

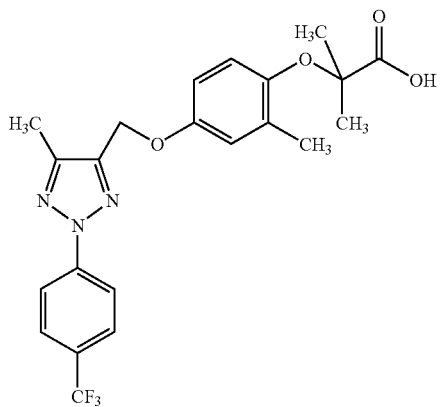

To a mixture of 2-(4-Hydroxy-2-methyl-phenoxy)-2-methyl-propionic acid ethyl ester (1 eq mmol) and compound 5C (1 eq) in MeCN (5 mL) was added Cs$_2$CO$_3$ (1.2 eg). The mixture was stirred at room temperature for 4 hrs. The mixture was filtered through Celite and washed with ethyl acetate. The solvent was evaporated and the residue was purified by flash chromatography on silica gel to give the desired ester.

To a solution of the above compound in THF and methanol was added aqueous LiOH (2 eq), the mixture was refluxed for 1 hr, acidified with 1N HCl to about pH 5, extracted with EtOAc. The organic phase was washed with brine, dried, and concentrated. The residue was recrystallized from hexanes and ethyl acetate to give desired acid. $^1$H NMR (400 MHz, CDCl$_3$) δ 7.97 (2H, d, J=8.4 Hz), 7.65 (2H, d, J=8.4 HZ), 6.96~6.92 (2H, m), 6.51 (1H, d, J=8.4 Hz), 4.6 (2H, s), 2.55 (3H, s), 2.18 (3H, s), 1.73 (6H, s).

Example 6B

2-[4-(2-Biphenyl-4-yl-5-methyl-2H-[1,2,3]triazol-4-yl-methoxy)-2-methyl-phenoxy ]2-methyl-propionic acid

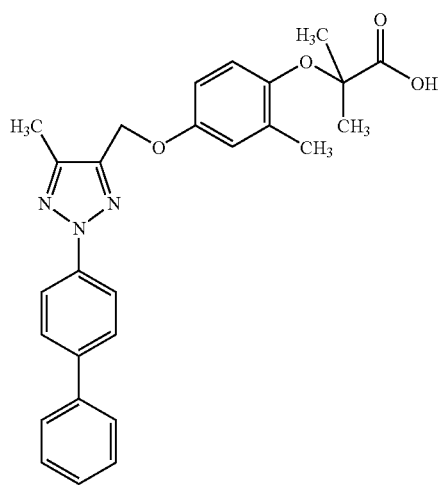

The following compound was made according to the procedure of Example 6B using compound 5F. $^1$H NMR (400 MHz, CDCl$_3$) δ 8.08~8.05 (2H, m7.7~7.66 (2H, m), 7.64~7.6 (2H, m), 7.48~7.44 (2Hm), 7.39~7.34 (1H, m), 6.87~6.83 (2H, m), 6.77 (1H, dd, J=8.8, 3.2 Hz), 5.15(2H, s), 4.09 (2H, s), 2.44 (3H, s), 2.24 (3H, s), 1.57 (6H , s).

Example 6C

2-Methyl-2-(2-methyl-4-{1-[5-methyl-2-(4-trifluoromethyl-phenyl)-2H-[1,2,3]triazol-4-yl]-ethoxy}-phenoxy)-propionic acid

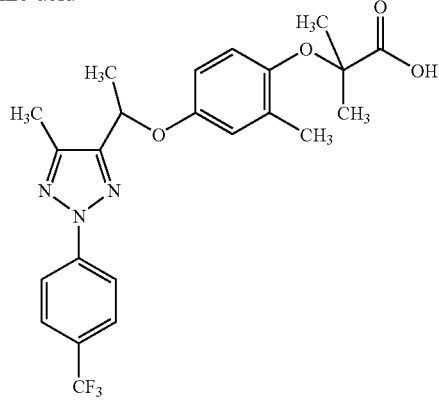

To a solution of 10B (0.27 g, 1 mmol) and 2-(4-Hydroxy-2-methyl-phenoxy)-2-methyl-propionic acid ethyl ester (0.24 g, 1 mmol) in THF (10 mL) was added PBu3 (0.3 g, 1.5 mmol) and DIAMIDE (0.25 g, 1.5 mmol), the mixture was stirred at room temperature for 20 hrs and the solvent was evaporated and the residue was purified by flash chromatography on silica gel to give 0.35 g desired ester.

To a solution of the ester (0.35 g,), in THF (3 mL) and methanol (3 mL) was added aqueous LiOH (2 mL, 2 mmol), the mixture was refluxed for 2 hr, acidified with 1N HCl, extracted with EtOAc. The organic phase was washed with brine, dried and concentrated, the residue was recrystallized from hexanes and ethyl acetate to give 0.25 g white solid $^1$H NMR MHz, CDCl$_3$) δ 8.13~8.1 (2H, m), 7.72~7.69 (2H, m), 6.78 (1H, d, J=3.2 Hz), 6.75(1H, d, J=8.8 Hz), 6.66 (1H, dd, J=8.8, 3.2 Hz), 5.55 (1H, q, J=6.8 Hz), 2.39 (3H, s), 2.18(3H, s), 1.73 (3H, d, J=6.8 Hz).

Example 6D (2-Methyl-4-{1-[5-methyl-2-(4-trifluoromethyl-phenyl)-2H-[1,2,3]triazol-4-yl]-ethoxy}-phenoxy)-acetic acid

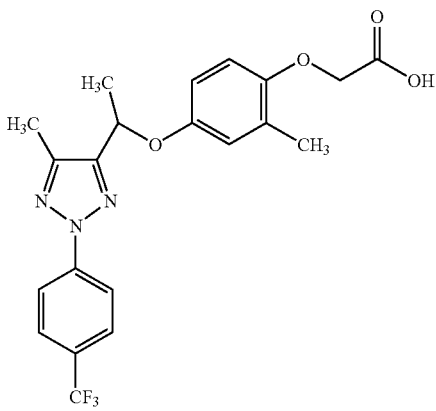

To a solution of 10B (0.39 g, 1.4 mmol) and (4-Hydroxy-2-methyl-phenoxy)-acetic acid ethyl ester (0.35 g, 1.68 mmol) in CH$_2$Cl$_2$ (10 mL) was added PPh$_3$ (0.73 g, 2.8 mmol) and DEAD (0.48 g, 2.8 mmol), the mixture was stirred at room temperature for 20 hrs and the solvent was evaporated and the residue was purified by flash chromatography on silica gel to give 0.3 g desired ester.

To a solution of the ester (0.3 g,), in THF (3 mL) was added aqueous LiOH (2 mL, 2 mmol), the mixture was stirred at room temperature for 1 hr, acidified with 1N HCl, extracted with EtOAc. The organic phase was washed with brine, dried and concentrated, the residue was recrystallized from hexanes and ethyl acetate to give 0.2 g white solid. $^1$H NMR (400 MHz, CDCl$_3$) δ 8.13 (2H, d, J=8 Hz), 7.71 (2H, d, J=8 Hz), 6.86 (1H, d, J=2.4 Hz), 6.78 (1H, dd, J=8.8, 3.2 Hz), 6.7 (1H, d, J=8.8), 5.13(2H, s), 4.63 (2H, s), 2.43 (3H, s), 2.18 (3H, s).

Example 6E

2-{4-[2-(4-Chloro-phenyl)-5-methyl-2H-[1,2,3]triazol-4-yl-methoxy]-2-methyl-phenoxy}-2methyl-propionic acid

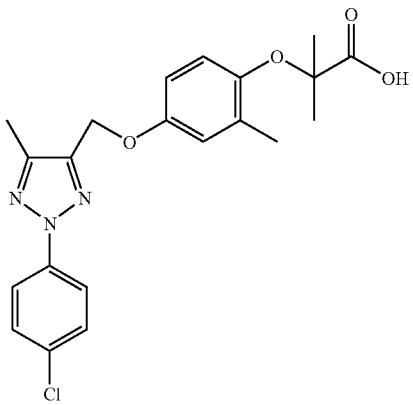

The title compound was prepared from intermediate compound 5I and 2-(4-Hydroxy-2-methyl-phenoxy)-2-methyl-propionic acid ethyl ester using the procedure described above. $^1$H NMR (400 MHz, DMSO-d$_6$) δ 7.93 (2H, dd, J=7.2, 2.0 Hz), 7.57 (2H, dd, J=7.2, 2.0 Hz), 6.87 (1H, d, 3.2 Hz), 6.77 (1H, dd, J=8.8, 3.2 Hz), 6.69 (1H, d, J=8.8 Hz), 5.12 (2H, s), 2.34 (3H, s), 2.12 (3H, s), 1.42 (6H, s).

Example 6F

{2-Methyl-4-[5-methyl-2-(4-trifluoromethyl-phenyl)-2H-[1,2,3]triazol-4-ylmethoxy]-phenoxy}-acetic acid

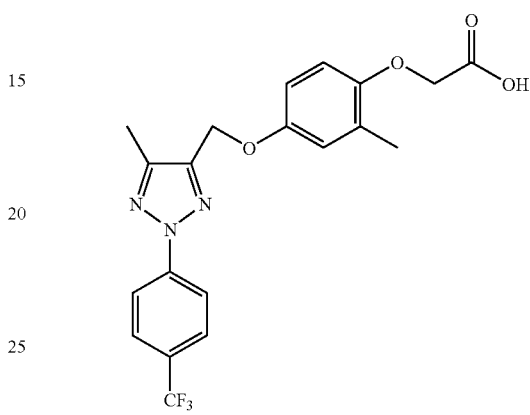

The title compound was prepared from intermediate compound 5A and 2-(4-Hydroxy-2-methyl-phenoxy)-acetic acid ethyl ester using the procedure described above. $^1$H NMR (400 MHz, DMSO-d$_6$) δ 8.14 (2H, d, J=8.8 Hz), 7.90 (2H, d, J=8.8 Hz), 6.89 (1H, d, J=2.8 Hz), 6.80 (1H, dd, J=8.8, 2.8 Hz), 6.74 (1H, d, J=8.8 Hz), 5.16 (2H, s), 4.60 (2H, s), 2.38 (3H, s), 2.16 (3H, s).

Example 6G

[4-(2-Biphenyl-4-yl-5-methyl-2H-[1,2,3]triazol-4-yl-methoxy)-2-methyl-phenoxy]-acetic acid

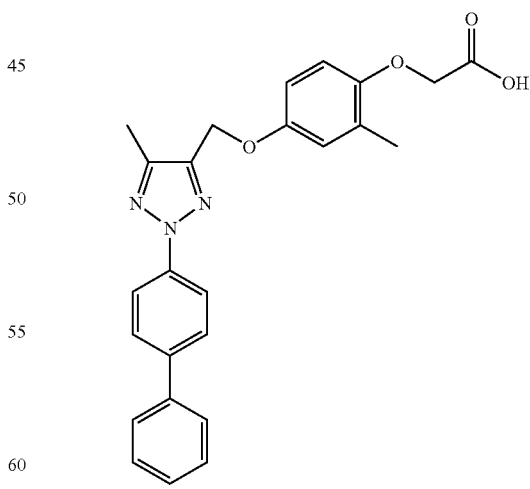

The title compound was prepared from intermediate compound 5F and 2-(4-Hydroxy-2-methyl-phenoxy)-acetic acid ethyl ester using the procedure described above. $^1$H NMR (400 MHz, CDCl$_3$) δ 8.07(2H, d, J=8.8 Hz), 7.68 (, d, J=8.8 Hz), 7.62 (2H, d, J=7.6 Hz), 7.46 (2H, d, J=7.6 Hz), 7.36

(1H, t, J=7.6 Hz), 6.88 (1H, d, J=2.4 Hz), 6.8 (1H, dd, J=8.8, 2.8 Hz), 6.71 (1h, d, J=9.2 Hz), 5.15(2H, s), 4.63 (2H, s), 2.44 (3H, s), 2.28 (3H, s).

Example 6H

2-{2-Chloro-4-[2-(4-chloro-phenyl)-5-methyl-2H-[1,2,3]triazol-4-ylmethoxy]-phenoxy}-2-methyl-propionic acid

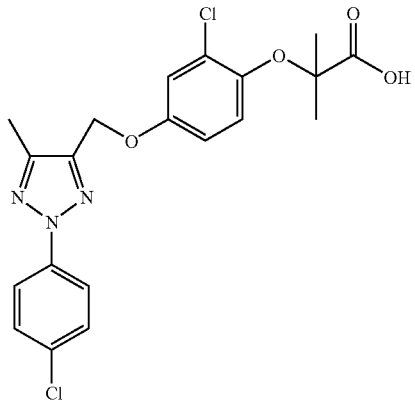

The title compound was prepared from intermediate compound 51 and 2-(4-Hydroxy-2-chloro-phenoxy)-2-methyl-propionic acid ethyl ester using the procedure described above. $^1$H NMR (400 MHz, CDCl$_3$) δ 7.95 (2H, dd, J=7.2, 2.0 Hz), 7.43 (2H, dd, J=7.2, 2.0 Hz), 7.10 (1H, d, J=3.2 Hz), 7.07 (1H, d, J=8.8 Hz), 6.87 (1H, dd, J=8.8, 3.2 Hz), 5.14 (2H, s), 2.43 (3H, s), 1.59 (6H, s).

Example 7A

2-{4-[5-[4-(4-Methoxy-phenyl)-piperazin-1-ylmethyl]-2-(4-trifluoromethyl-phenyl)-2H-[1,2,3]triazol-4-ylmethylsulfanyl]-2-methyl-phenoxy}-2-methyl-propionic acid (Compound 700)

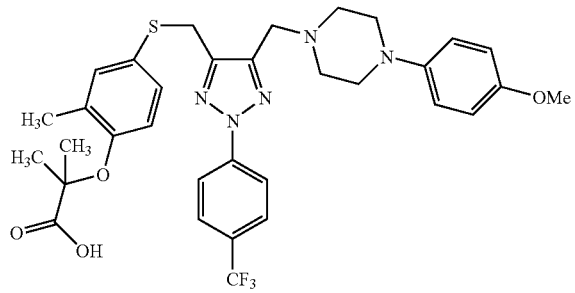

To a solution of compound 29 (0.43 g, 0.84 mmol) CH$_2$Cl$_2$(5 mL) was added methanesulfonyl chloride (0.11 g, 1 mmol) and triethyl amine (0.13 g, 1.26 mmol) at 0° C. the mixture was stirred at 0° C. for 1 hour. The mixture was diluted with EtOAc and washed with H$_2$O and brine. The organic phase was dried over Na$_2$SO$_4$ and evaporated to yield a crude mesylate. To the crude mesylate in THF (10 mL) was added 4-methoxyphenyl piperazine (0.32 g, 1.68 mmol) and the mixture was refluxed for 5 hours. After cooling to room temperature, the solvent was evaporated and the residue was purified by chromatography to produce 0.41 g desired product. $^1$H NMR (400 MHz, CDCl$_3$) δ 8.08(2H, d, J=8.8 Hz), 7.69(2H, d, J=8.8 Hz), 7.21(1H, d, J=2 Hz), 7.09~7.06(1H, m), 6.91~6.87(2H, m), 6.85~6.82 (2H, m), 6.53(1H, d, J=8.8 Hz), 4.24(2H, s), 4.2(2H, q, J=7.2 Hz), 3.76(3H, s), 3.65(2H, s), 3.1~3.07 (4H, m), 2.65~2.62 (4H, m), 2.16(3H, s), 1.56(6H, s), 1.21(3H, t, J=7.2Hz).

To a solution of the above compound in THF (4 mL) and methanol (4 mL) was added aqueous LiOH (1.8 mL, 1.8 mmol), the mixture was refluxed for 1 hr, acidified with 1N HCl to about pH 5, extracted with EtOAc. The organic phase was washed with brine, dried, and concentrated. The residue was recrystallized from hexanes and ethyl acetate to give 360 mg of a white solid. $^1$H NMR (400 MHz, CDCl$_3$) δ 8.1(2H, d, J=8.8 Hz), 7.69(2H, d, J=8.8 Hz), 7.24(1H, d, J=2 Hz), 7.02~6.98(3H, m), 6.86~6.83(2H, m), 6.72 (1H, d, J=8.4 Hz), 4.08(2H, s), 3.76(3H, s), 3.38(2H, s), 3.2~3.1(4H, m), 2.76~2.68(4H, m), 2.19(3H, s), 1.62(6H, s).

Example 7B

{4-[5-[4-(4-Methoxy-phenyl)-piperazin-1-ylmethyl]-2-(4-trifluoromethyl-phenyl)-2H-[1,2,3]triazol-4-ylmethylsulfanyl]-2-methyl-phenoxy}-acetic acid

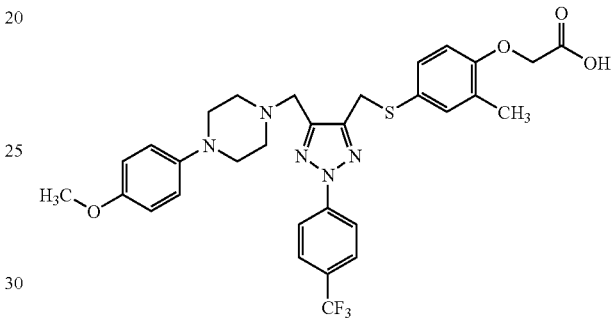

The following compound was made from intermediate 29B according to the procedure of Example 7A. $^1$H NMR (400 MHz, CDCl$_3$) δ 8.1 (2H, d, J=8.8 Hz), 7.7 (2H, J=8.8 Hz), 7.22 (1H, d, J=12 Hz), 7.15 (1H, dd, J=8, 2 Hz), 7.03~7.0 (2H, m), 6.86~6.83(2H, m), 6.68 (1H, d, J=8.4 Hz), 4.58 (2H, s), 4.11 (2H, s), 3.76 (3H, s), 3.5 (2H, s), 3.24~3.16 (4H, m), 2.84~2.76 (4H, m), 2.22 (3H, s).

Example 7C

2-{4-[5-[4-(4-Methoxy-phenyl)-piperazin-1-ylmethyl]-2-(4-trifluoromethyl-phenyl)-2H-[1,2,3]triazol-4-ylmethylsulfanyl]-phenoxy}-2-methyl-propionic acid

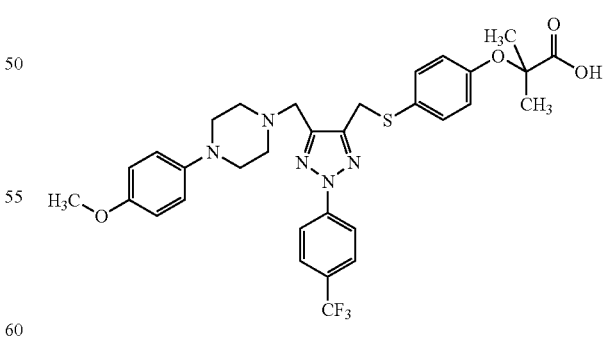

The following compound was made from intermediate 29C according to the procedure of Example 7A. $^1$H NMR (400 MHz, DMSO) δ 8.06 (2H, d, J=8.8 Hz), 7.88 (2H, J=8.8 Hz), 7.34~7.28 (2H, m), 6.86~6.82 (2H, m), 6.8~6.72 (4H, m), 4.3 (2H, s), 3.65 (3H, s), 3.58 (2H, s), 3.0~2.9 (4H, m), 2.55~2.45 (4H, m), 1.44 (6H, s).

Example 8

(2-Methyl-4-{2-[5-methyl-2-(4-trifluoromethyl-phenyl)-2H-[1,2,3]triazol-4-yl]-ethyl}-phenoxy)-acetic acid

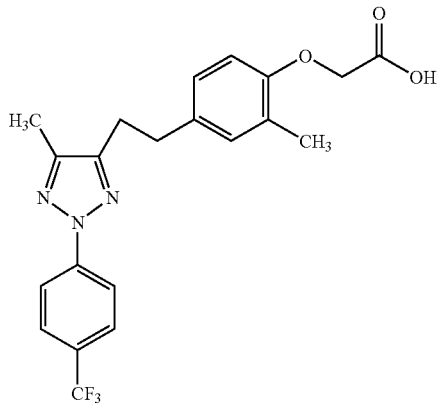

To a solution of [5-Methyl-2-(4-trifluoromethyl-phenyl)-2H-[1,2,3]triazol-4-ylmethyl]-triphenyl-phosphonium chloride (2.5 mmol) in THF (10 mL) was added BuLi (2 mmol) at 0C. the solution was stirred at 0C for 30 min and cooled to −78C. A solution of (4-Formyl-phenoxy)-acetic acid tert-butyl ester (0.24 g, 1 mmol) in THF (5 mL) was added, the reaction was allowed to warm to room temperature after 1 hr, quenched with EtOH, evaporated, chromatography on silica gel to give 0.5 g desired trans olefin.

The olefin (0.5 g) and 10% Pd/c in EtOAc (10 mL), was stirred under H2 at room temperature overnight. The mixture was filtrated through celite and washed with ethyl acetate, evaporated. The residue was dissolved in $CH_2Cl_2$ (5 mL), and TFA (0.3 mL) was added at 0C. the mixture was allowed to warm to room temperature and evaporated. The residue was recrystallized from EtOAc/Hexane to afford 0.28 g desired product. $^1$H NMR (400 MHz, $CDCl_3$) δ 8.1 (2H, d, J=8.8 Hz), 7.7 (2H, d, J=8.8 Hz), 7.04 (1H, d, J=1.2 Hz), 6.96~6.97 (1H, dd, J=8.4, 2 Hz), 6.67 (1H, d, J=8 Hz), 4.67 (2H, s), 2.94 (4H, s), 2.27 (3H, s), 2.2 (3H, s).

Example 9A

{2-Methyl-4-[5-methyl-2-(4-trifluoromethyl-phenyl)-2H-[1,2,3]triazol-4-ylmethanesulfinyl]-phenoxy}-acetic acid

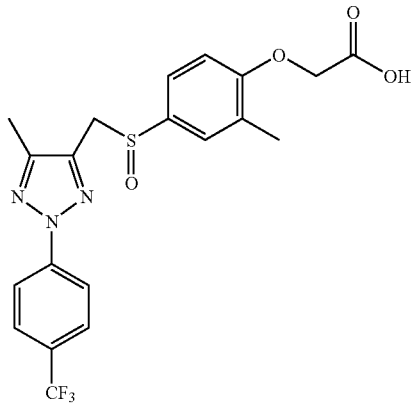

To a solution of Compound 100 (1 eq) in $CH_2Cl_2$ was added MCPBA (1.2 eg) at room temperature, the resulting mixture was stirred for 2 hrs, evaporated and chromatography on silica gel to give desired compound as a white solid. $^1$H NMR (400 MHz, DMSO) δ 8.01 (2H, d, J=8.4 Hz), 7.88(2H, d, J=8.4 Hz), 7.34~7.28 (2H, m), 6.97 (1H, d, J=9.2 Hz), 4.77(2H, s), 4.42 (1H, d, J=13.6 Hz), 4.27 (1H, d, J=13.6 Hz), 2.14 (3H, s), 2.09 (3H, s).

Example 9B

{2-Methyl-4-[5-methyl-2-(4-trifluoromethyl-phenyl)-2H-[1,2,3]triazol-4-ylmethanesulfonyl]-phenoxy}-acetic acid

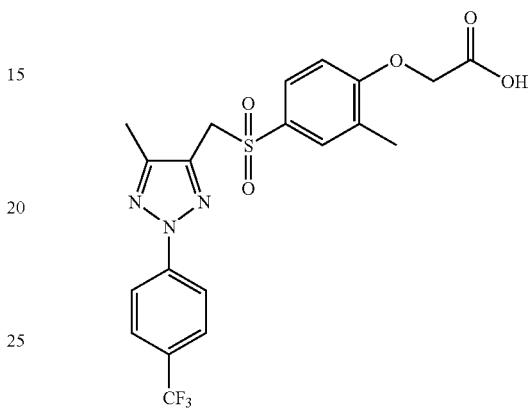

To a solution of Compound 100 (1 eq) in $CH_2Cl_2$ was added MCPBA (3 eg) at room temperature, the resulting mixture was stirred for 6 hrs, evaporated and chromatography on silica gel to give desired compound as a white solid. $^1$H NMR (400 MHz, DMSO) δ 7.99 (2H, d, J=8.8 Hz), 7.89(2H, d, J=8.4 Hz), 7.56~7.5 (2H, m), 7.03 (1H, d, J=8.4 Hz), 4.85(2H, s), 4.83 (2H, s), 2.18 (3H, s), 2.16 (3H, s).

Example 10

Measurement of PPARγ, δ, and α Transactivation Activity

Chimeric receptors were constructed in which the yeast transcription factor GAL4 DNA binding domain was fused to the ligand binding domain of either mouse PPARγ, mouse PPAR δ or mouse PPAR α in order to assess the ability of the compounds of the present invention to activate gene expression in a PPAR-dependent manner. The chimeric receptor expression plasmids (GAL4-nPPARγ, GAL4-mPPAR δ and GAL4-PPAR α) and the reporter plasmid containing 5×GAL4 binding site (pFR-Luc, obtained from Stratagene) were transfected into HEK293T cells using the Lipofectamine 2000 reagent (Invitrogen), according to the manufacturers instructions. Six hours after transfection, the culture medium was renewed and the cells were incubated for 20 hours in presence of either 1) DMSO (vehicle), 2) a compound of the invention or 3) a reference compound for comparison. Rosiglitazone (obtained from WDF Pharma) was used as a reference compound for the PPARγ assay; GW501516 (prepared as described in Sznaidman et al. Bioorg. Med. Chem. Lett. (2003) 13:1517-1521) was used as a reference compound for the PPAR δ assay and GW7647 (obtained from Sigma) was used as a reference compound for the PPAR α assay. Luciferase activity was measured as a reporter of gene expression. Luciferase activity on the cell lysates using the Steady-Glo reagent was measured according to the manufacturers instructions.

TABLE 1

Results of the PPARs transactivation assay for selected compounds from FIG. 1.

| Compounds | Gene Activation Assay: EC$_{50}$($\leq$10 μM) | | |
|---|---|---|---|
| | PPAR alpha | PPAR delta | PPAR gamma |
| 100 | − | + | ND |
| 660 | ND | + | ND |
| 670 | − | + | ND |
| 480 | + | + | − |
| 440 | − | + | − |
| 320 | − | + | ND |
| 110 | + | + | + |
| 210 | + | + | 10 |
| 360 | − | + | ND |
| 340 | + | + | ND |
| 640 | − | + | ND |
| 580 | + | + | ND |

ND: no activity detected @ 30 μM

As apparent from the test results above, the compounds of the invention are excellent modulators of PPAR.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having the formula:

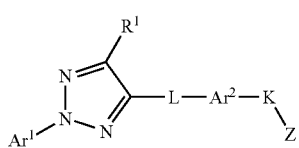

(I)

wherein
Ar$^1$ is phenyl, which is optionally substituted with from one to five R$^7$ substituents independently selected from the group consisting of halogen, (C$_1$-C$_8$)alkyl, halo(C$_1$-C$_8$)alkyl, and —OR$^2$;
Ar$^2$ is phenyl, which is optionally substituted with from one to four R$^8$ substituents independently selected from the group consisting of halogen, (C$_1$-C$_8$)alkyl, halo(C$_1$-C$_8$)alkyl, and —OR$^2$;
L is a member selected from the group consisting of —CH$_2$S— and —CH$_2$O—;
K is a member selected from the group consisting of a covalent bond and —OCH$_2$—
Z is CO$_2$R$^6$;
R$^1$ is selected from the group consisting of H and (C$_1$-C$_8$)alkyl;
each R$^2$ and R$^3$ is a member independently selected from the group consisting of H, (C$_1$-C$_8$)alkyl, halo(C$_1$-C$_8$)alkyl, —X$^3$OR$^9$, aryl, aryl(C$_1$-C$_4$)alkyl, and heteroaryl, or optionally, if both present on the same substituent, may be joined together to form a three- to eight-membered ring system;
R$^6$ is a member selected from the group consisting of H, (C$_1$-C$_8$)alkyl, halo(C$_1$-C$_8$)alkyl, —X$^4$OR$^2$, —X$^4$NR$^2$R$^3$, (C$_2$-C$_8$)alkenyl, (C$_3$-C$_7$)cycloalkyl, heterocyclyl, aryl (C$_1$-C$_4$)alkyl; and aryl(C$_2$-C$_8$)alkenyl;
R$^9$ is a member selected from the group consisting of H, (C$_1$-C$_8$)alkyl, halo(C$_1$-C$_8$)alkyl, aryl, aryl(C$_1$-C$_4$)alkyl, and heteroaryl;
each X$^3$ and X$^4$ is a member independently selected from the group consisting of (C$_1$-C$_4$) alkylene, (C$_2$-C$_4$)alkenylene, and (C$_2$-C$_4$)alkynylene; and pharmaceutically acceptable salts, solvates, hydrates and prodrugs thereof.

2. A compound of claim 1, wherein Ar$^1$ is phenyl optionally substituted with from one to three R$^7$ substituents independently selected from the group consisting of halogen, halo(C$_1$-C$_8$)alkyl, and —OR$^2$.

3. A compound of claim 1, wherein Ar$^1$ is
a member selected for the group consisting of:

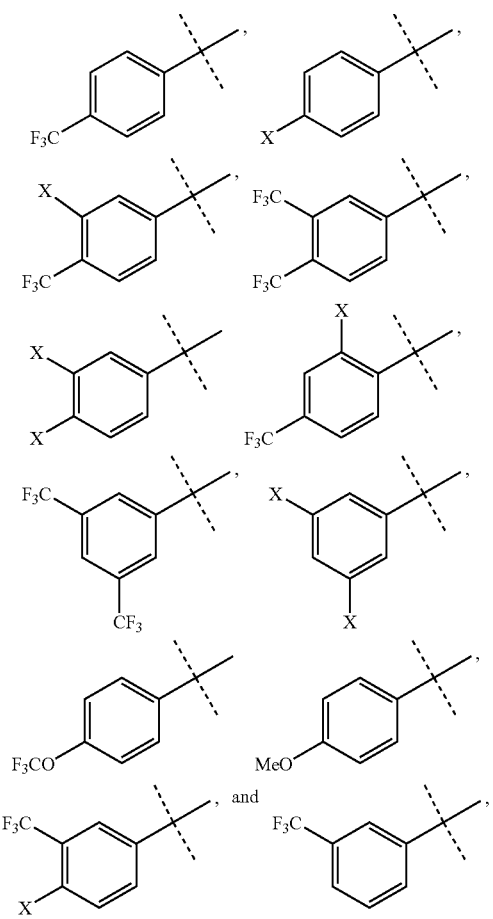

wherein X is a halogen; and
the dashed line indicates the point of attachment to the remainder of the molecule.

4. A compound of claim 3, wherein Ar$^1$ is

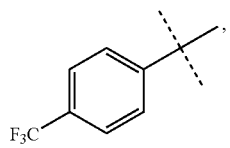

wherein the dashed line indicates the point of attachment to the remainder of the molecule.

5. A compound of claim 1, wherein R¹ is (C₁-C₈)alkyl.

6. A compound of claim 5, wherein R¹ is selected from the group consisting of CH₃ and CH(CH₃)₂.

7. A compound of claim 5, wherein R¹ is CH₃.

8. A compound of claim 1, wherein L is CH₂S.

9. A compound of claim 1, wherein K is OCH₂.

10. A compound of claim 1, wherein Z is CO₂R⁶.

11. A compound of claim 10, wherein R⁶ is H.

12. A compound of claim 1, wherein Ar² is phenyl optionally substituted with from one to three R⁸ substituents each independently selected from the group consisting of halogen, (C₁-C₈)alkyl, halo(C₁-C₈)alkyl, and —OR².

13. A compound of claim 12, wherein Ar² is phenyl optionally substituted with from one to two R⁸ substituents each independently selected from the group consisting of halogen, (C₁-C₈)atkyl, halo(C₁-C₈)alkyl, and —OR².

14. A compound of claim 12, wherein L is (CH₂)S.

15. A compound of claim 12, wherein K is OCH₂.

16. A compound of claim 12, wherein each R⁸ substituent is independently selected from the group consisting of halogen, (C₁-C₈)alkyl, and halo(C₁-C₈)alkyl.

17. A compound of claim 12, wherein Ar² has the formula:

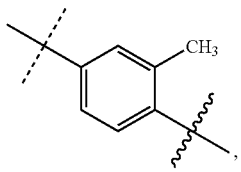

wherein the dashed line indicates the point of attachment to L and the wavy line indicates the point of attachment to K.

18. A compound of claim 17, wherein the compound is

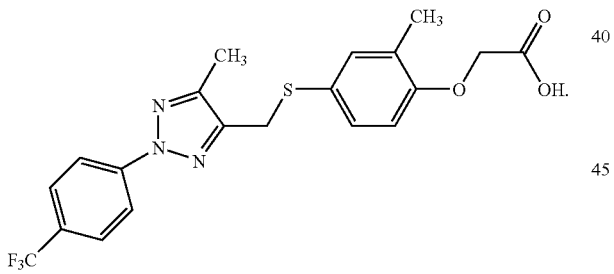

19. A compound selected from the group consisting of:
{2-Methyl-4-[5-methyl-2-(4-trifluoromethyl-phenyl)-2H-[1,2,3]triazol-4-ylmethylsulfanyl]-phenoxy}-acetic acid; {4-[5-Methyl-2-(4-trifluoromethyl-phenyl)-2H-[1,2,3 ]triazol-4-ylmethylsulfanyl]-phenoxy}-acetic acid; {2-Chloro-4-[5-methyl-2-(4-trifluoromethyl-phenyl)-2H-[1,2,3 ]triazol-4-ylmethylsulfanyl]-phenoxy}-acetic acid; {4-[5-Methyl-2-(4-trifluoromethyl-phenyl)-2H-[1,2,3]triazol-4-ylmethylsulfanyl]-2-trifluoromethyl -phenoxy}-acetic acid; {4-[5-Methyl-2-(4-trifluoromethyl-phenyl)-2H-[1,2,3]triazol-4-ylmethylsulfanyl]-2-trifluoromethoxy-phenoxy}-acetic acid; 5- {2-Methyl-4-[5-methyl-2-(4-trifluoromethyl-phenyl)-2H-[1,2,3]triazol-4-ylmethylsulfanyl]-phenoxymethyl}-1 H-tetrazole; {2-Bromo-4-[5-methyl-2-(4-trifluoromethyl-phenyl)-2H-[1,2,3 ]triazol-4-ylmethylsulfanyl]-phenoxy}-acetic acid; {2-Methoxy-4-[5-methyl-2-(4-trifluoromethyl-phenyl)-2H-[1,2,3] triazol-4-ylmethylsulfanyl]-phenoxy}-acetic acid; {2,6-Dimethyl-4-[5-methyl-2-(4-trifluoromethyl-phenyl)-2H-[1,2,3]triazol-4-ylmethylsulfanyl]-phenoxy}-acetic acid; {2-Methyl-4-[5-methyl -2-(4-trifluoromethyl-phenyl)-2H-[1,2,3]triazol-4-ylmethylsulfanyl]-phenyl}-acetic acid; {4-[5-Isopropyl-2-(4-trifluoromethyl-phenyl)-2H-[1,2,3]triazol-4-ylmethylsulfanyl]-2-methyl-phenoxy}-acetic acid; {2-Methyl-4-[5-propyl-2-(4-trifluoromethyl-phenyl)-2H-[1,2,3]triazol-4-ylmethylsulfanyl]-phenoxy}-acetic acid; {2-Methyl-4-[5-phenyl-2-(4-trifluoromethyl-phenyl)-2H-[1,2,3]triazol-4-ylmethylsulfanyl]-phenoxy}-acetic acid; {2-Methyl-4-[5-(2,2,2trifluoro-ethyl) -2-(4-trifluoromethyl-phenyl)-2H-[1,2,3]triazol-4-ylmethylsulfanyl]-phenoxy}-acetic acid; {2-Methyl-4-[5-trifluoromethyl-2-(4-trifluoromethyl-phenyl)-2H-[1,2,3]triazol-4-ylmethylsulfanyl[-phenoxy}-acetic acid; {4-[2-(4-Chloro-phenyl)-5-methyl-2H-[1,2,3 ]triazol -4-ylmethylsulfanyl]-2-methyl-phenoxy}-acetic acid; {4-[2-(4-Bromo-phenyl)-5-methyl-2H-[1,2,3] triazol-4-ylmethylsulfanyl]-2-methyl-phenoxy}-acetic acid; {4-[2-(3-Chloro-4-trifluoromethyl-phenyl)-5-methyl-2H-[1,2,3 ]triazol-4-ylmethylsulfanyl]-2-methyl-phenoxy}-acetic acid; {4-[2-(3,4-Bis-trifluoromethyl-phenyl)-5-methyl-2H-[1,2,3]triazol-4-ylmethylsulfanyl]-2-methyl-phenoxy}-acetic acid; {4-[2-(4-Methoxy-phenyl)-5-methyl-2H-[1,2,3]triazol-4-ylmethylsulfanyl[-2-methyl-phenoxy}-acetic acid; {2-Methyl-4-[5-methyl--2-(4trifluoromethoxy-phenyl)-2H-[1,2,3]triazol-4-ylmethylsulfanyl[-phenoxy}-acetic acid; {4-[2-(4-Chloro-3-trifluoromethyl-phenyl)-5-methyl-2H-[1,2,3]triazol-4-ylmethylsulfanyl]-2-methyl-phenoxy}-acetic acid; [4-(2-Benzo[1,3]dioxol-5-yl-5-methyl-2H-[1,2,3]triazol-4-ylmethylsulfanyl)-2-methyl-phenoxy]-acetic acid; {2-Methyl-4-[5-methyl-2-(3-trifluoromethyl-phenyl)-2H-[1,2,3]triazol-4-ylmethylsulfanyl]-phenoxy}-acetic acid; {4-[2-(3-Chloro-phenyl)-5-methyl-2H-[1,2,3] triazol-4-ylmethylsulfanyl]-2-methyl-phenoxy}-acetic acid; {4-[2-(3-Bromo-phenyl)-5-methyl-2H-[1,2,3] triazol-4-ylmethylsulfanyl]-2-methyl-phenoxy}-acetic acid; {2-Ethyl-4-[5-methyl-2-(4-trifluoromethyl-phenyl)-2H-[1,2,3]triazol-4-ylmethylsulfanyl]-phenoxy}-acetic acid; {2-Isopropyl-4-[5-methyl-2-(4-trifluoromethyl-phenyl)-2H-[1,2,3]triazol-4-ylmethylsulfanyl]-phenoxy}-acetic acid; {4-[2-(3-Fluoro-4-trifluoromethyl-phenyl)-5-methyl-2H-[1,2,3]triazol-4-ylmethylsulfanyl]-2-methyl-phenoxy}-acetic acid; {4-[2-(4-Fluoro-phenyl)-5-methyl-2H-[1,2,3]triazol-4-ylmethylsulfanyl]-2-methyl-phenoxy}-acetic acid; {4-[2-(2-Flouro-4-trifluoromethyl-phenyl)-5-methyl-2H-[1,2,3]triazol-4-ylmethylsulfanyl]-2-methyl-phenoxy}-acetic acid; {4-[2-(3,5-Bis-trifluoromethyl-phenyl)-5-methyl-2H-[1,2,3]triazol-4-ylmethylsulfanyl]-2-methyl-phenoxy}-acetic acid; {4-[2-(3,4-Dichloro-phenyl)-5-methyl-2H-[1,2,3]triazol-4-ylmethylsulfanyl]-2-methyl-phenoxy}-acetic acid; and {4-[2-(3,4-Difluoro-phenyl)-5-methyl-2H-[1,2,3] triazol-4-ylmethylsulfanyl]-2-methyl-phenoxy}-acetic acid.

20. A compound selected from the group consisting of:
{4-[2-(3,5-Bis-trifluoromethyl-phenyl)-5-methyl-2H-[1,2,3]triazol-4-ylmethylsulfanyl]-2-methyl-phenoxy}-acetic acid; {4-[2-(3,4-Dichloro-phenyl)-5-methyl-2H-[1,2,3]triazol-4-ylmethylsulfanyl]-2-methyl-phenoxy}-acetic acid; [4-(2-Biphenyl-4-yl-5-methyl- 2H-[1,2,3]triazol-4-ylmethylsulfanyl)-2-methyl-phenoxy]-acetic acid; {2-Methyl-4-[5-methyl-2-(4-trifluoromethyl-phenyl)-2H-[1,2,3]triazol-4-ylmethoxy]-phenoxy}-acetic acid and [4-(2-Biphenyl-4-yl-5-methyl-2H-[1,2,3]triazol-4-ylmethoxy)-2-methyl-phenoxy]-acetic acid.

21. A composition comprising one or more pharmaceutically acceptable caters, diluents, or excipients and a compound of claim 1.

* * * * *